US008937170B2

(12) United States Patent
Juntunen et al.

(10) Patent No.: US 8,937,170 B2
(45) Date of Patent: Jan. 20, 2015

(54) NUCLEIC ACIDS ENCODING FUNGAL PROTEASE

(71) Applicant: AB Enzymes Oy, Rajamaki (FI)

(72) Inventors: Kari Juntunen, Espoo (FI); Leena Valtakari, Rajamaki (FI); Susanna Makinen, Layliainen (FI); Jarno Kallio, Jarvenpaa (FI); Jari Vehmaanpera, Klaukkala (FI); Pentti Ojapalo, Tuusula (FI); Marja Paloheimo, Vantaa (FI)

(73) Assignee: AB Enzymes Oy, Rajamäki (FI)

( * ) Notice: Subject to any disclaimer, the term of this patent is extended or adjusted under 35 U.S.C. 154(b) by 60 days.

(21) Appl. No.: 14/066,110

(22) Filed: Oct. 29, 2013

(65) Prior Publication Data

US 2014/0134706 A1  May 15, 2014

Related U.S. Application Data

(62) Division of application No. 12/799,639, filed on Apr. 28, 2010, now Pat. No. 8,603,795.

(60) Provisional application No. 61/214,975, filed on Apr. 30, 2009.

(30) Foreign Application Priority Data

Apr. 30, 2009 (FI) ..................... 20095497

(51) Int. Cl.
*C07H 21/04* (2006.01)
*C12N 9/58* (2006.01)
*C11D 3/386* (2006.01)

(52) U.S. Cl.
CPC ..... *C12N 9/58* (2013.01); *C11D 3/386* (2013.01); *C11D 3/38681* (2013.01)
USPC ........................................ 536/23.2

(58) Field of Classification Search
CPC combination set(s) only.
See application file for complete search history.

(56) References Cited

U.S. PATENT DOCUMENTS

| 3,652,399 | A | 3/1972 | Isono et al. |
| 5,288,627 | A | 2/1994 | Nielsen et al. |
| 5,770,418 | A | 6/1998 | Yaver et al. |
| 5,843,745 | A | 12/1998 | Berka et al. |
| 5,962,765 | A | 10/1999 | St. Leger et al. |
| 6,300,116 | B1 | 10/2001 | Von der Osten et al. |
| 6,573,086 | B1 | 6/2003 | Emalfrab et al. |
| 6,682,924 | B1 | 1/2004 | Sierkstra et al. |
| 2004/0023355 | A1 | 2/2004 | Sierkstra et al. |
| 2010/0120649 | A1 | 5/2010 | Andersen |
| 2011/0003729 | A1 | 1/2011 | Juntunen et al. |
| 2011/0008870 | A1 | 1/2011 | Makinen et al. |
| 2011/0028375 | A1 | 2/2011 | Juntunen et al. |
| 2012/0107905 | A1 | 5/2012 | Juntunen et al. |

FOREIGN PATENT DOCUMENTS

| EP | 0244234 | 11/1987 |
| EP | 0352244 A2 | 1/1990 |
| EP | 0290567 | 6/1992 |
| EP | 0290569 | 6/1992 |
| EP | 0519229 | 12/1992 |
| EP | 1870453 | 2/1994 |
| EP | 0479870 | 10/2000 |
| EP | 1347045 | 9/2003 |
| EP | 1464626 A2 | 10/2004 |
| EP | 1009815 B1 | 1/2008 |
| EP | 1464626 | 11/2009 |
| EP | 1464626 B1 | 11/2009 |
| WO | 88/03946 | 6/1988 |
| WO | 88/07581 | 10/1988 |
| WO | 89/04361 | 5/1989 |
| WO | 89/06270 | 7/1989 |
| WO | 92/03529 | 3/1992 |
| WO | 92/05239 | 4/1992 |
| WO | 92/18599 | 10/1992 |
| WO | 94/25583 | 11/1994 |
| WO | 96/18722 | 6/1996 |
| WO | 97/02753 | 1/1997 |
| WO | 97/08325 | 3/1997 |

(Continued)

OTHER PUBLICATIONS

McDonagh et al, Production of caseinophosphopeptides (CPPs) from sodium caseinate using a range of commercial protease preparations. International Dairy Journal (1998), 8(1), 39-45.*
Saeki et al., "Detergent Alkaline Proteases: Enzymatic Properties, Genes, and Crystal Structures," Journal of Bioscience and Bioengineering, 103(6):501-508 (2007).
Venalainen et al., "Evolutionary relationships of the prolyl oligopeptidase family enzymes," Eur. J. Biochem., 271:2705-2715 (2004).
Abu-Shady, M. R. et al., "Production, Partial Purification and Some Properties of Thermostable Alkaline Protease from Malbranchea sulfurea and its Compatibility with Commercial Detergents", Afr. J. Mycol. and Biotech., vol. 9, No. 3, (2001), pp. 17-26.

(Continued)

*Primary Examiner* — Sheridan Swope
(74) *Attorney, Agent, or Firm* — Fish & Richardson P.C.

(57) ABSTRACT

The present invention is related to a fungal serine protease enzyme, which comprises an amino acid sequence of the mature Fe_RF6318 enzyme having an amino acid sequence of SEQ ID NO: 15. The serine protease is obtainable from *Fusarium equiseti*, more preferably from the deposited strain CBS 119568. Also disclosed are nucleic acid sequences encoding said protease, such as plasmid pALK2521 comprising the nucleotide sequence SEQ ID NO:9 deposited in *E. coli* RF7664 under accession number DSM 22171 and plasmid pALK2529 comprising the full-length gene SEQ ID NO: 10 deposited in *E. coli* RF7800 under accession number DSM 22172. Said protease is useful as an enzyme preparation applicable in detergent compositions and for treating fibers, for treating wool, for treating hair, for treating leather, for treating food or feed, or for any applications involving modification, degradation or removal of proteinaceous material.

46 Claims, 25 Drawing Sheets

(56) References Cited

FOREIGN PATENT DOCUMENTS

| WO | 97/28243 | 8/1997 |
|---|---|---|
| WO | 98/20116 | 5/1998 |
| WO | 02/08398 | 1/2002 |
| WO | 2006/073839 | 7/2006 |
| WO | 2007/145963 | 12/2007 |
| WO | 2008/045148 | 4/2008 |
| WO | 2009/096916 | 8/2009 |
| WO | 2010/039840 | 4/2010 |
| WO | 2010/125174 | 11/2010 |
| WO | 2010/125175 | 11/2010 |
| WO | 2011/003968 | 1/2011 |
| WO | 2012/107905 | 5/2012 |

OTHER PUBLICATIONS

Altschul S.F. et al. 1990 Basic Local Alignment Search Tool J. Mol Biol. 215:403-410.
AMFEP list of commercial enzymes. www. amfep.org updated Nov. 30, 2007.
Antal, Z. S. et al., "Colony growth, in vitro antagonism and secretion of extracellular enzymes in cold-tolerant strains of Trichoderma species", Mycol. Res., vol. 5, (2000), pp. 545-549.
Anwar, A. and Saleemuddin, M. 1998 Alkaline proteases: a review. Bioresource Technology 64: 175-183.
Banerjee, U. C. et al., "Thermostable alkaline protease from *Bacillus brevis* and its characterization as a laundry detergent additive", Process Biochemistry, vol. 35, (1999), pp. 213-219.
Beg et al., "Purification and characterization of an oxidation-stable, thiol-dependent serine alkaline protease from *Bacillus mojavensis*," Enzyme and Microbial Technology, 32:394-304 (2003).
Bolton, ET. and Mccarthy B.J. 1962. A general method for the isolation of RNA . . . Proc Nat. A. S. 48: 1390-1397.
Chen, Y-J and Inoye, M. 2008. The intramolecular chaperone mediated protein folding. Curr. Opinion in Structural Biology. 18:765-770.
Cherry, J.R. and Fidantsef, A. L. 2003. Directed evolution of industrial enzymes . . . Curr. Opinion in biotechnol. 14: 438-443.
D'Acunzo, F. et al., "Oxidation of phenols by laccase and laccase-mediator systems", Eur. J. Biochem., vol. 269, (2002), pp. 5330-5335.
Database EMBL (online) Sep. 27, 2001 Accession No. BI750343.
Database EMBL (online) Apr. 20, 2007 "*Hypocrea lixii* mRNA for serin endopeptidase (p10261 gene)" CP002594316 EMBL:AM294980.
Database EMBL (online), Jun. 15, 2004. Fg02_08b01_RFg02_AAFC_ECORC_Fusarium_gramine arum-mycelium Gibberella zeae cDNA clone Fg02_08b01, mRNA sequence.: Expressed sequence tags from Fusarium gramineum mycelium. Database accession No. BI750343.
Database EPO Proteins (online) May 10, 2010 Accession No. HC687299.
Database UniProt (online) May 29, 2007, "subName: Full=serin endopeptidase;" XP00259425 EB1 accession No. UNIPROT:A4V8W7.
Database Uniprot (online), Feb. 2, 2009. "Full=Serin endopeptidase" *Trichoderma harzianum* (*Hypocrea lixii*). ID A4V8W7_TRIHA. Database accession No. A4V8W7.
Dienes, D. et al., "Identification of a trypsin-like serine protease from *Trichoderma reesei* GM9414", Enzyme and Microbial Technology, vol. 40, (2007), pp. 1087-1094.p-.
Edman P. and Begg, G. 1967. Eur. J. Biochem. 1: 80-91.
EMBL database (online), Database Accession No. DR657362, Jul. 14, 2005, from Brown, D. W., et al., "Analysis of 87,000 expressed sequence tags reveals alternatively spliced introns in multiple genes of the fumonisin gene cluster", (Unpublished) (1 page).
EPO database (online) Nov. 2, 2008. Sequence 313 from Patent WO2008045148. *Hypocrea lixii*. ID GM007507.
European Patent Office Database (online), Nov. 20, 2008. Sequence 313 from patent WO2008045148:, *Hypoxrea lixii* proteinn, ID GM007507, Database accession No. GM007507.
European Patent Office database (online), Database Accession No. GM007507, Nov. 20, 2008, from Madison, E.L., "Protease screening methods and proteases identified thereby"; Sequence 313 from Patent No. WO2008045148-A1, Apr. 17, 2008 (1 page).
Fabbrini, M. et al., "Comparing the catalytic efficiency of some medicators of lacasse", Journal of Molecular Catalysis B: Enzymatic, vol. 16, (2002), pp. 231-240.
Galye et al., Identification of regions in interleukin-1 alpha important for activity. J. Biol. Chem. Oct. 15, 1993; 268(29):22105-11.
Gasteiger, E. et al. 2003 ExPASy: the proteomics server for in-depth . . . Nucleic Acid Res. 31 (13): 3784-3788.
Gaucher, G. M. et al. "567. Thermomycolin", Handbook of Proteolytic Enzymes, (2004), pp. 1834-1835.
Gayle, R. B. et al., "Identification of Regions in Interleukin-la Important for Activity", The Journal of Biological Chemistry, vol. 268, No. 29, (1993), pp. 22105-22111.
Genbank Acc#AAA34209 from Geremia et al., Mol Microbiol May 1993; 8(3):603-613. Alignment with SEQ ID No. 10 of U.S. Appl. No. 12/803,456 (3 pages).
Genbank database, Database Accession No. AAA34209.1, May 28, 1993, from Geremia, R.A. et al., "Molecular Characterization of the proteinase-encoding gene, prbl, related to mycoparasitism by *Trichoderma harzianum*", Molecular Microbiology, vol. 8, No. 3, (1993), pp. 603-613 (3 pages).
Germia, R.A. et al 1993. Molecular characterization of the proteinase-encoding . . . Molec. Microbiol. 8(3):603-613.
Guo et al., Protein tolerance to random amino acid change. Proc. Natl. Acad. Sci. USA, Jun. 22, 2004; 101(25):9205-9210. Epub Jun. 14, 2004.
Gupta, R. et al. 2002. An overview on fermentation, downstream processing . . . Appl. Microbiol Biotechnol. 60:381-395.
Gurr, S. J. et al.1987 The structure and organization of nuclear genes . . . pp. 93-139. In (JR Kinghorn, ed.) Gene Structure in Eukaryotic Microbes.
International Search Report from corresponding PCT Application No. PCT/EP2011/068837 dated Dec. 15, 2011, (6 pages).
Joutsjoki, V. V. et al. 1993. Transformation of *Trichoderma reesei* with the Hormoconis . . . Curr Genet 24: 223-228.
Kalisz, H. M. 1988. Microbial proteases. Advances in Biochemical engineering / Biotechnology. vol. 36 pp. 1-65.
Karhunen, T. et al. 1993. High frequency one-step gene replacement in Trichoderma . . . Mol Gen Genet 241 :515-522.
Kelly, J. M. et al., "Transformation of *Aspergillus niger* by the amdS gene of *Aspergillus nidulans*", The EMBO Journal, vol. 4, No. 2, (1985), pp. 475-479.
Kredics, L. et al., "Extracellular Proteases of *Trichoderma* Species", Acta Microbiologica et Immunologica Hungarica, vol. 52, No. 2, (2005), pp. 169-184.
Laemmli, U.K. 1970 Cleavage of structural proteins during the assembly . . . Nature 227915): 680-685.
Maladier L. et al.1989 Cloning of the nitrate reductase gene (niaD) of *Aspergillus nidulans* . . . Gene 78: 147-157.
Manonmani, H.K. et al. "Purification and properties of an extracellular proteinase of *Trichoderma koningii*", Enzyme Microb. Technol., vol. 15, (1993), pp. 624-628.
Martinez, D. et al., "Gene sequencing and analysis of the biomass-degrading fungus *Trichoderma reesei* (syn. *Hypocrea jecorina*)", Nature Biotechnology, vol. 26., No. 5, (2008), pp. 553-560.
Mauer K-H. 2004. Detergent proteases. Current opinion in Biotechnology. 15: 330-334.
Maurer, K. H. et al. "Enzymes, Detergent", Encyclopedia of Industrial Biotechnology: Bioprocess, Bioseparation, and Cell Technology (Michael C. Flickinger, ed.), John Wiley & Sons, Inc., (2010), pp. 1-17.
Mcdonagh et al., Production of caseinophosphopeptides (CPPs) from sodium caseinate using a range of commercial protease preparations. International Dairy Journal (1998), 8(1), 39-45.
NCBI REFSEQ Database (online Nov. 3, 2009) Hypothetical protein FG03325.2 (*Gibberella zeae* PH-1). Accession XP_383491.
NCBI REFSEQ Database, Sep. 4, 2008 "Hypothetical protein FG03315.1 (*Gibberella zease* PH-1)", version XP_383491.1., Database accession No. XP-383491.

(56) References Cited

OTHER PUBLICATIONS

Nielsen, H. et al. 1997. Identification of procaryotic and eucaryotic signal peptides and . . . Protein Engineering 10(1): 1-6.
Nielsen, H. et al. 1998. Prediction of signal peptides and signal anchors by a hidden . . . Proc. 6th Intl. Cont. of Intelligent systems. pp. 122-130.
Ong, P. S. et al., "Production, purification and characterization of thermomycolase, the extracellular serine protease of the thermophilic fungus Malbranchea pulchella var. sulfurea", Can. J. Microbiol., vol. 22, (1975), pp. 165-175.
Paloheimo, M. et al. 2003. High-Yield Production of a Bacterial Xylanase in the Filamentous Fungus . . . Appl. Env. Microbiol. p. 7073-3082.
Penttila, M. et al. 1987 A versatile transformation system for the cellulolytic filamentous fungus . . . Gene 61: 155-164.
Poutanen, P. et al. 2001. Use of matrix-assisted laser desorption/ionization . . . Rapid Comm. Mass Spectrom. 15:1685-1962.
Pozo, M. J., "Functional analysis of tvsp1, a serine protease-encoding gene in the biocontrol agent *Trichoderma virens*", Fungal Genetics and Biology, vol. 41, (2004), pp. 336-348.
Raeder, U. et al. 1985. Rapid Preparation of DNA from filamentous fungi. Lett. Appl. Microbiol. 1: 17-20.
Rao, M.B et al. 1998. Molecular and Biotechnological aspects of microbial proteases. Microbiol. and Mol. Biol. Rev. 62(3): 597-635.
Sambrook, J. and Russell, D. W., Molecular Cloning, a Laboratory Manual, Cold Spring Harbor Laboratory, New York, US, (2001), pp. 6.51, 6.52, 11.27.
Search Report issued in the corresponding Finnish Patent Application No. 20106135 dated May 13, 2011, 1 page.
Shevchenko, A. et al. 1996. Mass spectrometric sequencing of proteins from silver-stained . . . Anal.Chem 68:850-858.
Shimogaki, H. 1991. Purification and properties of a novel Surface-active agent . . . Agric. Biol. Chem 55(9): 2251-2258.
Siezen, R. J. et al., "Subtilases: The superfamily of subtilisin-like serine proteases", Protein Science, vol. 6, (1997), pp. 501-523 (total pages 30).
Steyaert, J. M. et al., "Co-expression of two genes, a chitinase (chit42) and proteinase (prb1) implicated in mycoparasitism by *Trichoderma hamatum*", Mycologia, vol. 96, No. 6, (2004), pp. 1245-1252.
Suarez, M. B. et al. 2007. Characterization of genes encoding novel peptidases in the biocontrol fungus . . . Curr. Genet. 51 :331-342.
UNIPROT 201110 database Acc# A4V8W7_TRIHA from Suarez et al., Curr Genet. May 2007; 51(5):331-42, Epub Apr. 6, 2007, Alignment with SEQ ID No. 18.
UNIPROT database (online), Database Accession No. A5JS74, Jun. 26, 2007, from Gao, L. et al., "Gene cloning of serine protease from Hirsutella minnesotania", Submitted (Apr. 2007) to the EMBL/GenBank/DDBJ databases, (1 page).
UNIPROT database (online), Database Accession No. C7YXB3, Oct. 13, 2009, from Coleman, J. J. et al., "The genome of *Nectria haematococca*: contribution of supernumerary chromosomes to gene expansion", PLoS Genet. 5: E1000618-E1000618, (2009), (1 page).
UNIPROT database (online), Database Accession No. C7ZKJ9, Oct. 13, 2009, from Coleman, J.J. et al, "The genome of *Nectria haematococca*: contribution of supernumerary chromosomes to gene expansion", PLoS Genet. 5: E1000618-E1000618, (2009), (1 page).
UNIPROT database (online), Database Accession No. C9SL49, Nov. 24, 2009, from Ma, L.—J.J., et al, "Annotation of *Verticillium albo-atrum* VaMs. 102.", Submitted (May 2008) to the EMBL/GenBank/DDBJ databases, (1 page).
UNIPROT database (online), Database Accession No. E3Q3S5, Jan. 11, 2011, from Vaillancourt, L. et al., "The genome sequence of *Glomerella graminicola* strain M1.001.", Submitted (Jun. 2009) to the EMBL/GenBank/DDBJ databases, (1 page).
UNIPROT database (online), Database Accession No. Q69IF7, Sep. 13, 2004, from Hane, J.K. et al., "Dothideomycete-plant interactions illuminated by genome sequencing and EST analysis of the wheat pathogen *Stagonospora nodorum*.", Plant Cell, vol. 19, (2007), pp. 3347-3368, (1 page).
UNIPROT database Acc# Q86ZV3_TRIHM from Steyaert et al., Mycologia 96: 1245-1252 (2004). Alignment with SEQ ID No. 10 of U.S. Appl. No. 12/803,456 (2 pages).
UNIPROTKB database (online), Database Accession No. Q03420, Jun. 16, 2009, from Geremia, R. A. et al., "Molecular characterization of the preoteinase-encoding gene, prb1, related to mycoparasitism by *Trichoderma harzianum*", Mol. Microbiol., vol. 8, (1993), pp. 603-613 (2 pages).
UNIPROTKB database (online), Database Accession No. Q86ZV3-TRIHM, Feb. 10, 2009, from Steyaert, J. M. et al, Co-expression of two genes, a chitinase (chit42) and proteinase, Mycologia, vol. 96, No. 6, (2004), pp. 1245-1252 (1 page).
UNIPROTKB database (online), Database Accession No. Q874K4, Feb. 10, 2009, from Pozo, J. J. et al., "Functional analysis of tvsp1, a serine protease-encoding gene in the biocontrol agent *Trichoderma virens* ", Fungal Genet. Biol., vol. 41, (2004), pp. 336-348 (1 page).
USPTO in house alignment AAA34209 from Geremia et al., Mol. Microbiol. May 1993; 8(3):603-613.
USPTO in house alignment Q86ZV3_TRIHM from Steyaert et al. Mycologia 96:1245-1252 (2004).
Whisstock et al., Prediction of protein function from protein sequence and structure. Q. Rev. Biophys. Aug. 2003; 36(3):307-40. Review.
Whisstock, J. C. et al., "Prediction of protein function from protein sequence and structure", Quarterly Reviews of Biophysics, vol. 36, No. 3 (2003), pp. 307-304.

\* cited by examiner

Fig. 1A

```
  1 atgactagct tccgcgtat cttgcagctc cttgcagctc tgctgccgc agtcctcgcc gctcccaccg agaagcgaca ggagctcact
  1  m  t  s    f  r  r    i  a  l  g    l  a  a  l    l  l  p  a  v  l  a    a  p  t    e  k  r    g  e  l  t 91 gccgcgctg acaagtacat catcacctc aagcccgagg ctgctgaggc caaggtcgag gctcacatgg gctcacaccg cctggttac cgacgtcccac
 31  a  a  p    d  k  y    i  i  t  l    k  p  e    a  a  e    a  k  v  e    a  h  m    a  w  v    t  d  v  h 181 cgccgcagcc tcggcaagcc tgacacttc ggtgttgaga agaagttcaa catcagcagc tggaacgcct actctggcga gttcgacgat
 61  r  r  s    l  g  k    r  d  t  s    g  v  e    k  k  f  n    i  s  s    w  n  a    y  s  g    e  f  d  d 271 gctaccattg ctgagatcaa gaagagcccc gaggttgcct tcgtcgagcc cgactacatt gtcaccctcg actacaaggt tgagctctc
 91  a  t  i    a  e  i    k  k  s  p    e  v  a    f  v  e    p  d  y  i    v  t  l    d  y  k    v  e  p  l 361 tctgaccgtg CTCTGACCAC TCAGAGCAAC GCTCCTTGGG GTCTTGCTGC CATCTCCCGC CGAACCCCCG GTGGCAGCAC CTACACCTAC
121  s  d  r    L  T  T    Q  S  N    A  P  W    G  L  A  A    I  S  R    R  T  P    G  G  S    T  Y  T  Y 451 GACACCACTG CCGGTGCCGG TACTTACGGT TACGTCGTTG ACTCTGGTAT CAACACCGCC CACACTGACT CAACACCGCC CGCACCACCG TGCTTCTCTC
151  D  T  T    A  G  A    G  T  Y  G    Y  V  V    D  S  G    I  N  T  A    H  T  D    Q  H  R    R  A  S  L 541 GGTTACAACG CTGCTGGTGG CGCCACGGTG GATACCCTTG GCCACGGTGT CCACGGTGCT GGTACCATTG CCTCCAACAC CTACGGTGTT
181  G  Y  N    A  A  G    G  A  H  T    D  T  L    G  H  G    T  H  V  A    G  T  I    A  S 631 GCCAAGCGTg taagtacaat catacccac atgagctaca aacatgatctg aactttatac ttactattat tagGCCAACG TCATCTCTGT
211  A  K  R                                                                                   A  N    V  I  S 721 CAAGGTTTC GTCGGTAACC AAGCTTCTAC CTCTGTTATC CTTGCTGGTT TCAACTGGGC TGTCAACGAC ATCACCTCCA AGAACCGTGC
219  V  K  V  F    V  G  N    Q  A  S  T    S  V  I    L  A  G    F  N  W  A    V  N  D    I  T  S    K  N  R 811 TAGCCGCTCT GTCATCAACA TGTCTCTCGG TGGTCCCTCT TCTCAGACCT GGGCTACTGC CATCAACGCT GCCTACAGCC AAGGTGTCCT
249  A  S  R  S    V  I  N    M  S  L  G    G  P  S    S  Q  T    W  A  T    A  I  N  A    A  Y  S    Q  G  V
```

Fig. 1B

```
 901  CTCCGGTTGTT GCTGCCGGTA ACGGTGATTC CAACGGTCGT CCTCTCCCCG CCTCTGGCCA GTCTCCTGCC AACGTTCCCA ACGCTATCAC
 279   L  S  V  V   A  A  G    N  G  D    S  N  G  R    P  L  P     A  S  G    Q  S  P  A    N  V  P     N  A  I
 991  CGTTGCTGCC GCCGACTTCA GCTGGCGAAC TGCCCTCTTC ACCAACTACG GTCCTGAGGT CGATGTCTTC GGTCCTGGTG TCAACATCCA
 309   R  F  A  A    A  D  S  S    W  A  N     T  A  S  F    T  N  Y     G  P  E  V    D  V  F     G  P  G    V  N  I
1081  GTCCACCTGG TACACCTCCA ACAGGCTAC ACAACCATC AGGGGTACCT CCCTCACGTT GCTGGTCTTG CTCTCTACCT
 339   Q  S  T  W    Y  T  S     N  S  A     T  N  T  I    S  G  T     S  M  A    C  P  H  V    A  G  L    A  L  Y
1171  CCAGGCTCTC GAGAACCTCA ATACCCCTGC TGCCGTCACC AGTCTCTTGC AACCGCATCA CACTACCGGC GCAGCCCTCAG
 369   L  Q  A  L    E  N  L    N  T  P     A  A  V  T    N  R  K  S  L    H  Y  R  G    R  I  T    G  S  L
1261  CGGCAGCCCC AACGCCATGG CTTTCAACGG CGCTACTGCT TAA
 399   S  G  S  P    N  A  M     A  F  N     G  A  T  A    *
```

Performance of recombinant Fe_RF6318
Blood-milk-ink stain
30 °C, pH 9, 60 min.

Performance of recombinant Fe_RF6318
Blood-milk-ink stain
50 °C, pH 9, 60 min.

Performance of recombinant Fe_RF6318
Blood-milk-ink stain
40 °C, pH approx. 10, 60 min.
Detergent powder Performance of recombinant Fe_RF6318
Blood-milk-ink stain
40 °C, pH approx. 10, 60 min.
Detergent powder and bleaching agents Performance of recombinant Fe_RF6318
Blood-milk-ink stain
50 °C, pH approx. 10, 60 min.
Detergent powder Performance of recombinant Fe_RF6318
Blood-milk-ink stain
50 °C, pH approx. 10, 60 min.
Detergent powder and bleaching agents Performance of recombinant Fe_RF6318
Blood-milk-ink stain
Liquid detergent Ariel Sensitive
40 °C, pH approx. 7.9, 60 min.

Performance of recombinant Fe_RF6318
Blood-milk-ink stain
Liquid base detergent for coloured fabrics
30 °C, Detergent concentration 5 g/l, pH 7.5

Performance of recombinant Fe_RF6318
Blood-milk-ink stain
Liquid base detergent for coloured fabrics
30 °C, Detergent concentration 5 g/l (enzyme dosage calculated as protein)

Performance of recombinant Fe_RF6318
Blood-milk-ink stain
Liquid base detergent for coloured fabrics
30 °C, Detergent concentration 3.3 g/l, pH 7.4

Performance of recombinant Fe_RF6318
Blood-milk-ink stain
Liquid base detergent for coloured fabrics
30 °C, Detergent concentration 1 g/l, pH 7.3

Performance of recombinant Fe_RF6318
Blood-milk-ink stain
Ariel Sensitive
30 °C, Detergent concentration 5 g/l, pH 8

Performance of recombinant Fe_RF6318
Blood-milk-ink stain
Ariel Sensitive
30 °C, Detergent concentration 5 g/l (enzyme dosage calculated as protein)

Performance of recombinant Fe_RF6318
Blood-milk-ink stain
Ariel Sensitive
30 °C, Detergent concentration 3.3 g/l, pH 7.9

Performance of recombinant Fe_RF6318
Blood-milk-ink stain
Ariel Sensitive
30 °C, Detergent concentration 1 g/l, pH 7.6

Performance of recombinant Fe_RF6318
Launder Ometer test
Liquid detergent Ariel Sensitive, 30 °C
Blood-milk-ink stain Performance of recombinant Fe_RF6318
Launder Ometer test
Liquid detergent Ariel Sensitive, 30 °C
Blood-milk-ink Performance of recombinant *Fe*_RF6318
Launder Ometer test
Liquid detergent Ariel Sensitive, 30 °C
Grass Performance of recombinant Fe_RF6318
Launder Ometer test
Liquid detergent for coloured fabrics, 30 °C
Blood-milk-ink Performance of recombinant Fe_RF6318
Launder Ometer test
Liquid detergent for coloured fabrics, 30 °C
Blood-milk-ink Performance of recombinant Fe_RF6318
Launder Ometer test
Liquid detergent for coloured fabrics, 30 °C
Grass Performance of recombinant Fe_RF6318
Launder Ometer test
Liquid detergent for coloured fabrics, 30 °C
Cocoa Total stain removal efficency (delta %SR) of stains 1,2,3,4,5,6,7 and 8
Full scale Total stain removal efficency (delta %SR) of stains 1,2,3,4,5,6,7 and 8
Full scale Stain removal effecting in liquid detergent base for coloured fabrics in full scale trial at 30 °C
Blood/milk/ink (CO)

Stain removal effecting in liquid detergent base for coloured fabrics in full scale trial at 30 °C
Blood/milk/ink (PE-CO)

Stain removal effecting in liquid detergent base for coloured fabrics in full scale trial at 30 °C
Milk/pigment Stain removal effecting in liquid detergent base for coloured fabrics in full scale trial at 30 °C
Ground nut oil/milk Stain removal effecting in liquid detergent base for coloured fabrics in full scale trial at 30 °C
Egg Yolk/pigment Performance of recombinant Fe_RF6318
Blood-milk-ink stain
10 °C, pH 9, 60 min.

Performance of recombinant Fe_RF6318
Blood-milk-ink stain
20 °C, pH 9, 60 min.

Performance of recombinant Fe_RF6318
Blood-milk-ink stain
30 °C, pH 9, 60 min.

Performance of recombinant Fe_RF6318
Blood-milk-ink stain
40 °C, pH 9, 60 min.

Performance of recombinant Fe_RF6318
Blood-milk-ink stain
50 °C, pH 9, 60 min.

Performance of recombinant Fe_RF6318
Blood-milk-ink stain
60 °C, pH 9, 60 min.

Performance of recombinant Fe_RF6318
Blood-milk-ink stain
Liquid base detergent 10 °C, Detergent concentration 3.3 g/l Performance of recombinant Fe_RF6318
Blood-milk-ink stain
Liquid base detergent 20 °C, Detergent concentration 3.3 g/l

# NUCLEIC ACIDS ENCODING FUNGAL PROTEASE

PRIORITY

This application is a divisional of U.S. application Ser. No. 12/799,639, filed Apr. 28, 2010 (now U.S. Pat. No. 8,603, 795), which claims priority from the Finnish national application number FI20095497 filed on Apr. 30, 2009 and of the U.S. Provisional patent application No. 61/214,975 filed on Apr. 30, 2009. The contents of all of the above applications are incorporated herein by reference in their entireties.

FIELD OF THE INVENTION

The present invention relates to a fungal serine protease enzyme useful in various applications, particularly in laundry and dish-washing detergents. The invention relates to a nucleic acid molecule encoding said enzyme, a recombinant vector, a host cell for producing said enzyme, an enzyme composition comprising said enzyme as well as a process for preparing such composition. This invention relates also to various uses of said enzyme or compositions comprising said enzyme.

BACKGROUND

Microbial proteases are among the most important hydrolytic enzymes and find applications in various industrial sectors, such as detergents, food, leather, pharmaceuticals, diagnostics, waste management and silver recovery. Microbial extracellular proteases account for a major part, more than one third, of the total worldwide industrial enzyme sales (Chemy and Fidantsef, 2003). Approximately 90% of the commercial proteases are detergent enzymes (Gupta et al., 2002). Most commercial proteases, mainly neutral and alkaline are produced by organisms belonging to the genus *Bacillus*.

Serine proteases of the subtilisin family or subtilisins produced by *Bacillus* species form the largest subgroup of industrial proteases. These enzymes are commercially important as protein degrading component or additive of washing detergents. The commercial detergent preparations currently in use comprise the naturally occurring alkaline serine proteases originating from *Bacillus* species or are recombinant protease preparations (Maurer, 2004). Variants of the natural enzymes with improved catalytic efficiency and/or better stability towards temperature, oxidizing agents and changing washing conditions have been developed through site-directed and/or random mutagenesis. Examples of commercial proteases are such as subtilisin Carlsberg (Alcalase®, Novozymes, DK), subtilisin 309 (Savinase®, Novozymes, DK), Subtilisin 147 (Esperase®, Novozymes, DK), Kannase® (Novozymes, DK), Purafect® (Genencor Inc., USA), Purafect® Ox, Properase® (Genencor Inc., USA) and the BLAP S and X series (Henkel, Del.).

Several alkaline serine proteases (EC 3.4.21) and genes encoding these enzymes have also been isolated from eukaryotic organisms, including yeast and filamentous fungi. U.S. Pat. No. 3,652,399 and EP 519229 (Takeda Chemical Industries, Ltd., JP) disclose an alkaline protease from the genus *Fusarium* (asexual state, teleomorph) or *Gibberella*, (sexual state, anamorph) particularly from *Fusarium* sp. S-19-5 (ATCC 20192, IFO 8884), *F. oxysporum* f. sp. *lini* (IFO 5880) or *G. saubinetti* (ATCC 20193, IFO6608), useful in the formulation of detergent and other cleanser compositions. WO 88/03946 and WO 89/04361 (Novo Industri A/S, DK) disclose an enzymatic detergent additive and a detergent composition comprising a protease and a lipase, wherein the fungal protease is derived from *Fusarium*, particularly *F. oxysporum* or *F. solani*. A detergent additive comprising protease with specificity for peptide bonds adjacent to only one or two specific amino acids is disclosed in WO89/06270. WO1994025583 (NovoNordisk A/S, DK) discloses an active trypsin-like protease enzyme derivable from a *Fusarium* species, in particular a strain of *F. oxysporum* (DSM 2672), and the DNA sequence encoding the same. The amino acid sequence of a novel protease deriving from *Fusarium* sp. BLB (FERM BP-10493) is disclosed in WO 2006101140 (SODX Co. Ltd, Nakamura). Also, alkaline proteases from fungal species such as *Tritirachium* and *Conidiobolus* have been reported (reviewed in Anwar and Saleemuddin, 1998).

Use of fungal serine proteases in different applications is also known from several patent applications. For example, combination of a cellulase and a protease, particularly a trypsin-like protease from *Fusarium* sp. DSM 2672 as a detergent additive or composition is disclosed in WO 1992018599 (NovoNordisk A/S). Such detergent compositions may further comprise reversible protease inhibitors for stabilizing the enzyme(s) as disclosed in WO 1992003529 and WO 1992005239 (NovoNordisk A/S). Process for removal or bleaching of soiling or stains from cellulosic fabrics with an enzyme hybrid comprising a catalytically active amino acid sequence such protease linked to an amino acid sequence comprising a cellulose binding domain is disclosed in WO 1997028243 (NovoNordisk A/S). WO 1997002753 (NovoNordisk A/S) discloses a method for gentle cleaning of soiled process equipment using a lipase and a protease being preferably a serine protease obtainable from *Fusarium*. Use of *F. equiseti* and other fungi in reducing organic matter in waste waters is disclosed in the EP 1464626 patent application (Biovitis S.A., FR).

The socioeconomic challenges and governmental regulations have forced detergent industry to take in consideration many environmental aspects including not only the use of more lenient chemicals, which can be used in minor amounts and therefore leave less environmental waste trails, but also the need of energy saving. Detergent enzymes, particularly proteases, are important ingredient in detergent compositions. The need to save energy by decreasing the washing temperatures and the increased use of synthetic fibers which cannot tolerate high temperatures and current lifestyle have changed customer habits towards low washing temperatures and has created a demand for new enzymes, which are effective in low temperatures.

Despite the fact that numerous patent publications, reviews and articles have been published, in which serine proteases from various microorganisms, for example, the low temperature alkaline proteases from actinomycete (*Nocardiopsis dassonvillei*) and fungal (*Paecilomyces marquandii*) microorganisms are disclosed, e.g. in EP 0290567 and EP 0290569 (Novo Nordisk A/S, DK), there is still a great need for alternative serine proteases, which are suitable for and effective in modifying, degrading and removing proteinaceous materials particularly in low or moderate temperature ranges and which are stable in the presence of detergents with highly varying properties.

Detergent industry is making great advances in adapting its new products to customers' habits and needs, the properties of new textile products and new washing machines. It is evident that when developing new detergents, particularly laundry and dish wash compositions, a wide range of varying and rapidly changing demands have to be satisfied. In order to fulfill all varying demands of detergent industry and governmental regulations, new serine protease ingredients for detergent compositions should not only be able to accomplish their tasks in wide pH and temperature ranges and remain stable in variety of conditions, including mechanical and chemical interventions in combination with a variety of different detergents, it is also desirable that the serine protease can be produced in high amounts, which can be cost-effectively down-stream processed, by easy separation from fermentation broth and mycelia.

SUMMARY OF THE INVENTION

The aim of the present invention is to provide a serine protease of fungal origin which shows broad substrate specificity, is active at broad pH ranges and has a broad temperature optimum, i.e. functions both at low and moderate temperatures. The serine proteases for laundry and dish detergents have to be stable also in the presence of detergents or to be compatible with detergents. Particularly, the object of the invention is to provide a serine protease, which is capable of removing proteinaceous material, including stains in washing laundry and dishes, at lower temperatures than the present commercial enzyme preparations, thereby saving energy. The fungal serine protease can be produced in high-yielding fungal hosts and its down-stream processing, e.g. separation of fermentation broth and mycelia is easy to perform.

The present invention relates to a fungal serine protease enzyme, which has serine protease activity and comprises an amino acid sequence of the mature Fe_RF6318 enzyme as defined in SEQ ID NO:15 or an amino acid sequence having at least 86% identity to the amino acid sequence of the mature Fe_RF6318 enzyme defined in SEQ ID NO:15.

The enzyme of the invention is obtainable from *Fusarium equiseti*, more preferably from the deposited strain CBS 119568.

The enzyme has a molecular mass between 25 and 35 kDa. The enzyme has optimal temperature at the range from 30° C. to 70° C. at pH 9. Said enzyme has pH optimum at the pH range of at least pH 6 to pH 11 at 50° C. The temperature and pH optima were determined using 15 min reaction time and casein as a substrate. The serine protease of the invention is capable in degrading or removing proteinaceous stains in the presence of detergent between 10° C. and 60° C.

The fungal serine protease enzyme of the invention is encoded by an isolated polynucleotide sequence, which hybridizes under stringent conditions with a polynucleotide sequence included in plasmid pALK2521 comprising the nucleotide sequence SEQ ID NO:9 deposited in *E. coli* RF7664 under accession number DSM 22171.

Said enzyme is encoded by an isolated polynucleotide sequence, which encodes a polypeptide comprising an amino acid sequence of the mature Fe_RF6318 enzyme as defined in SEQ ID NO:15 or an amino acid sequence having at least 86% identity to the amino acid sequence of the mature Fe_RF6318 defined in SEQ ID NO:15. Preferably, said enzyme is encoded by an isolated nucleic acid molecule comprising the nucleotide sequence SEQ ID NO:14.

The full-length fungal serine protease enzyme of the invention is encoded by the polynucleotide sequence included in pALK2529 deposited in *Escherichia coli* RF7800 under accession number DSM 22172.

The fungal serine protease enzyme is produced from a recombinant expression vector comprising the nucleic acid molecule encoding a fungal serine protease of the invention operably linked to regulatory sequences capable of directing the expression of the serine protease encoding gene in a suitable host. Suitable hosts include heterologous hosts, preferably microbial hosts of the genus *Trichoderma, Aspergillus, Fusarium, Humicola, Chrysosporium, Neurospora, Rhizopus, Penicillium* and *Mortiriella*.

Preferably said enzyme is produced in *Trichoderma* or *Aspergillus*, most preferably in *T. reesei*.

The present invention relates also to an isolated nucleic acid molecule encoding a fungal serine protease enzyme selected from the group consisting of:
  (a) a nucleic acid molecule encoding a polypeptide having serine protease activity and comprising the amino acid sequence as depicted in SEQ ID NO:15;
  (b) a nucleic acid molecule encoding a polypeptide having serine protease activity and at least 86% identity to the amino acid sequence of SEQ ID NO:15;
  (c) a nucleic acid molecule comprising the coding sequence of the nucleotide sequence as depicted in SEQ ID NO: 10;
  (d) a nucleic acid molecule comprising the coding sequence of the polynucleotide sequence contained in DSM 22171 or DSM 22172;
  (e) a nucleic acid molecule the coding sequence of which differs from the coding sequence of a nucleic acid molecule of any one of (c) to (d) due to the degeneracy of the genetic code; and
  (f) a nucleic acid molecule hybridizing under stringent conditions to a nucleic acid molecule contained in DSM 22171, and encoding a polypeptide having serine protease activity and an amino acid sequence which shows at least 86% identity to the amino acid sequence as depicted in SEQ ID NO:15.

The invention further relates to a recombinant expression vector comprising the nucleotide sequence of the invention operably linked to regulatory sequences capable of directing expression of said serine protease encoding gene in a suitable host. Suitable hosts include heterologous hosts, preferably microbial hosts of the genus *Trichoderma, Aspergillus, Fusarium, Humicola, Chrysosporium, Neurospora, Rhizopus, Penicillium* and *Mortiriella*. Preferably said enzyme is produced in *Trichoderma* or *Aspergillus*, most preferably in *T. reesei*.

The invention relates also to a host cell comprising the recombinant expression vector as described above. Preferably, the host cell is a microbial host, such as a filamentous fungus. Preferred hosts are of a genus *Trichoderma, Aspergillus, Fusarium, Humicola, Chrysosporium, Neurospora, Rhizopus, Penicillium* and *Mortiriella*. More preferably the host is *Trichoderma* or *Aspergillus*, most preferably a filamentous fungus *T. reesei*.

The present invention relates to a process of producing a polypeptide having serine protease activity, said process comprising the steps of culturing the host cell of the invention and recovering the polypeptide. Also within the invention is a polypeptide having serine protease activity encoded by the nucleic acid sequence of the invention and which is obtainable by the process described above.

The invention relates to a process for obtaining an enzyme preparation comprising the steps of culturing a host cell of the invention and either recovering the polypeptide from the cells or separating the cells from the culture medium and obtaining the supernatant. Within the invention is also an enzyme preparation obtainable by the process described above.

The invention relates to an enzyme preparation, which comprises the serine protease enzyme of the invention.

The enzyme preparation of the invention may further comprise other enzymes selected from the group of protease, amylase, cellulase, lipase, xylanase, mannanase, cutinase, pectinase or oxidase with or without a mediator as well as suitable additives selected from the group of stabilizers, buffers, surfactants, bleaching agents, mediators, anti-corrosion agents, builders, antiredeposition agents, optical brighteners, dyes, pigments, caustics, abrasives and preservatives, etc.

The spent culture medium of the production host can be used as such, or the host cells may be removed, and/or it may be concentrated, filtrated or fractionated. It may also be dried. The enzyme preparation of the invention may be in the form of liquid, powder or granulate.

Also within the invention is the use of the serine protease enzyme or the enzyme preparation of the invention for detergents, for treating fibers, for treating wool, for treating hair, for treating leather, for treating food or feed, or for any applications involving modification, degradation or removal of proteinaceous material. Particularly, the enzyme or enzyme preparation is useful as a detergent additive in detergent liquids and detergent powders.

BRIEF DESCRIPTION OF DRAWINGS

FIG. 1 shows the nucleotide sequence of the *Fusarium equiseti* RF6318 Fe prtS8A gene (SEQ ID NO: 10) and the deduced amino acid sequence (SEQ ID NO: 11). The putative signal peptide (amino acid residues 1-20 of SEQ ID NO:11; nucleic acid residues 1-60 of SEQ ID NO:10), analyzed by SignalP V3.0 program is in lower case letters and underlined. The pro sequence (nucleic acid residues 61-369 of SEQ ID NO:10) and the deduced amino acids of the pro sequence (amino acid residues 21-123 of SEQ ID NO:11) are in lower case letters. The mature nucleotide (nucleic acid residues 370-1303 of SEQ ID NO:10) and peptide sequences (amino acid residues 124-412 of SEQ ID NO:11) are in capital letters (N-terminal sequence determined from the purified wild type Fe_RF6318 protein). The location of the putative intron sequence (nucleic acid residues 640-703 of SEQ ID NO:10) is in lower case, italic letters and marked by a dotted line below the nucleotide sequence. The stop codon is shown by an asterisk below the sequence. The N-terminal sequence and peptide sequences obtained from the wild type Fe_RF6318 protein are highlighted with gray background.

FIG. 1A shows the nucleotide sequence of Fe prt8A gene from the ATG start codon to the CCT codon (nucleotides 898 to 900), the sequence region encoding the amino acid sequence from Met 1 to Val278 of the Fe_RF6318 protein.

FIG. 1B shows the nucleotide sequence of Fe prt8A gene from CTC codon (nucleotides 901 to 903) to the TAA stop codon, the sequence region encoding the amino acid sequence from Leu279 to Ala412 of the Fe_RF6318 protein.

FIG. 10A shows performance with detergent concentration of 5 g/l and pH 7.5.

FIG. 10B shows performance with detergent concentration of 5 g/l (enzyme dosage calculated as protein).

FIG. 10C shows performance with detergent concentration of 3.3 g/l and pH 7.4.

FIG. 10D shows performance with detergent concentration of 1 g/l and pH 7.3.

FIG. 11A shows performance with detergent concentration of 5 g/l and pH 8.

FIG. 11B shows performance with detergent concentration of 5 g/l (enzyme dosage calculated as protein).

FIG. 11C shows performance with detergent concentration of 3.3 g/l and pH 7.9

FIG. 11D shows performance with detergent concentration of 1 g/l and pH 7.6.

FIG. 12A shows performance on blood/milk/ink/PE-cotton (Art. 117, EMPA).

FIG. 12B shows performance on blood/milk/ink/Cotton (Art. 116, EMPA)

FIG. 12C shows performance on grass (Art. 164, EMPA).

FIG. 13A shows performance on blood/milk/ink/PE-cotton (Art. 117, EMPA).

FIG. 13B shows performance on blood/milk/ink/Cotton (Art. 116, EMPA).

FIG. 13C shows performance on grass (Art. 164, EMPA).

FIG. 13D shows performance on Cocoa (Art. 112, EMPA).

FIG. 14A describes total stain removal efficiency when protease preparations were dosed according to the activity.

FIG. 14B describes total stain removal efficiency when protease preparations were dosed according to the amount of protein.

FIG. 15A describes stain removal on blood/milk/ink/Cotton (C-05-014/CFT).

FIG. 15B describes stain removal on blood/milk/ink/PE-Cotton (C-05-014/CFT).

FIG. 15C describes stain removal on chocolate milk/pigment/Cotton (C-03-030/CFT).

FIG. 15D describes stain removal on groundnut oil/milk/Cotton (C-05-014/CFT).

FIG. 15E describes stain removal on egg yolk/pigment/Cotton (CS-38-010/CFT).

FIG. 16A shows the performance of recombinant protein Fe_RF6318 and commercial protease preparations at 10° C.

FIG. 16B shows the performance of recombinant protein Fe_RF6318 and commercial protease preparations at 20° C.

FIG. 16C shows the performance of recombinant protein Fe_RF6318 and commercial protease preparations at 30° C.

FIG. 16D shows the performance of recombinant protein Fe_RF6318 and commercial protease preparations at 40° C.

FIG. 16E shows the performance of recombinant protein Fe_RF6318 and commercial protease preparations at 50° C.

FIG. 16F shows the performance of recombinant protein Fe_RF6318 and commercial protease preparations at 60° C.

FIG. 17A shows performance at 10° C.

FIG. 17B shows performance at 20° C.

SEQUENCE LISTING

Figure 2:
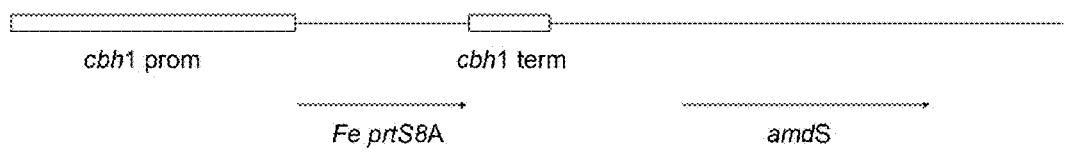
FIG. 2 schematically shows the cassette used for expressing the Fe prtS8A gene in *Trichoderma reesei*.

SEQ ID NO:1 Sequence of an aminoterminal peptide #3792 from *Fusarium equiseti* RF6318 protease.

SEQ ID NO:2 Sequence of a tryptic peptide 1246.673 from *Fusarium equiseti* RF6318 protease.

SEQ ID NO:3 Sequence of a tryptic peptide 3341.633 from *Fusarium equiseti* RF6318 protease.

SEQ ID NO:4 Sequence of a tryptic peptide 1503.799 from *Fusarium equiseti* RF6318 protease.

SEQ ID NO:5 The sequence of the oligonucleotide primer PRO87 derived from the aminoterminal peptide SEQ ID NO:1.

SEQ ID NO:6 The sequence of the oligonucleotide primer PRO88 derived from the aminoterminal peptide SEQ ID NO:1.

SEQ ID NO:7 The sequence of the oligonucleotide primer PRO89 derived from peptide SEQ ID NO:4.

SEQ ID NO:8 The sequence of the oligonucleotide primer PRO90 derived from peptide SEQ ID NO:4.

SEQ ID NO:9 The sequence of the PCR fragment obtained using the primers PRO88 (SEQ ID NO:6) and PRO89 (SEQ ID NO:7) and *Fusarium equiseti* RF6318 genomic DNA as a template.

SEQ ID NO:10 The nucleotide sequence of the full-length *Fusarium equiseti* RF6318 protease gene (Fe prtS8A).

SEQ ID NO:11 The deduced amino acid sequence of the full-length *Fusarium equiseti* RF6318 protease (Fe_RF6318) including amino acids from Met1 to Ala412.

SEQ ID NO:12 The nucleotide sequence encoding the amino acid sequence of the proenzyme form of *Fusarium equiseti* RF6318 protease.

SEQ ID NO:13 The amino acid sequence of the proenzyme form of *Fusarium equiseti* RF6318 protease including amino acids Ala21 to Ala 412 of the full length protease.

SEQ ID NO: 14 The nucleotide sequence encoding the amino acid sequence of the mature form of *Fusarium equiseti* RF6318 protease.

SEQ ID NO:15 The amino acid sequence of the mature form of *Fusarium equiseti* RF6318 protease including amino acids Ala124 to Ala412 of the full length enzyme.

Depositions

*Fusarium equiseti* RF6318 was deposited at the Centraalbureau Voor Schimmelcultures at Uppsalalaan 8, 3508 AD, Utrecht, the Netherlands on 7 Apr. 2006 and assigned accession number CBS 119568.

The *E. coli* strain RF7664 including the plasmid pALK2521 was deposited at the Deutsche Sammlung von Mikroorganismen und Zellkulturen GmbH (DSMZ), Inhoffenstrasse 7 b, D-38124 Braunschweig, Germany on 14 Jan. 2009 and assigned accession number DSM 22171.

The *E. coli* strain RF7800 including the plasmid pALK2529 was deposited at the Deutsche Sammlung von Mikroorganismen und Zellkulturen GmbH (DSMZ), Inhoffenstrasse 7 b, D-38124 Braunschweig, Germany on 14 Jan. 2009 and assigned accession number DSM 22172.

DETAILED DESCRIPTION

The present invention provides a serine protease of fungal origin, which protease shows broad substrate specificity, is stable at high pH ranges and has a broad temperature optimum, i.e. good performance both at low and moderate temperatures. The enzyme is ideal for detergent applications, withstanding oxidizing and chelating agents and being effective at low enzyme levels in detergent solutions. Particularly, the serine protease is active at temperatures as low as 10° C., the preferred range being from 10° C. to 60° C. Thus, the present invention provides an alternative serine protease for use in detergent and other applications. The fungal serine protease can be produced in high-yielding fungal hosts and its down-stream processing, e.g. separation of fermentation broth and mycelia is easy to perform.

By "serine protease" or "serine endopeptidase" or "serine endoproteinase" is in connection to this invention meant an enzyme classified as EC 3.4.21 by the Nomenclature of the International Union of Biochemistry and Molecular Biology. Serine proteases are found in both single-cell and complex organisms. Based on their structural similarities, serine proteases have been grouped into at least six clans (SA, SB, SC, SE, SF and SG; S denoting serine protease), which have been further subgrouped into families with similar amino acid sequences and three-dimensional structures (see, for example the Serine protease home page at biochem.wusthedu/~protease/, Department of Biochemistry and Molecular Biophysics, Washington University of Medicine, St. Louis, Mo., USA). These protein hydrolyzing or degrading enzymes are characterized by the presence of a nucleophilic serine group in their active site, and the proteases of clan SA and clan SB are also distinguished by having essential aspartate and histidine residues, which along with the serine, form a catalytic triad.

The major clans include the "chymotrypsin-like", including chymotrypsin, trypsin and elastase (clan SA) and "subtilisins-like" (clan SB) serine proteases. The enzymes target different regions of the polypeptide chain, based upon the side chains of the amino acid residues surrounding the site of cleavage. The serine protease of the present invention belongs to clan SB.

The characterized "subtilisin-like serine proteases" or "subtilases" are generally bacterial in origin. This class of proteases, represented by various *Bacillus*, like *B. amyloliquifaciens, B. licheniformis* and *B. subtilis* (Rao et al., 1998), is specific for aromatic or hydrophobic residues, such as tyrosine, phenylalanine and leucine.

By the term "serine protease activity" as used in the invention is meant hydrolytic activity on protein containing substrates, e.g. casein, haemoglobin, keratin and BSA. The methods for analysing proteolytic activity are well-known in the literature and are referred e.g. in Gupta et al. (2002).

Proteases can be classified using group specific inhibitors. The diverse group of "serine protease inhibitors", includes synthetic chemical inhibitors and natural proteinaceous inhibitors. One group of natural inhibitors are serpins (abbreviated from serine protease inhibitors), such as antithrombin and alpha 1-antitrypsin. Artificial synthetic inhibitors include 3,4-dichloroisocoumarin (3,4-DCI), diisopropylfluorophosphate (DFP), phenylmethylsulfonyl fluoride (PMSF) and tosyl-L-lysine chloromethyl ketone (TLCK). Some of the serine proteases are inhibited by thiol reagents such as p-chloromercuribenzoate (PCMB) due to the presence of a cysteine residue near the active site. Thus, the serine protease activity can be determined in an assay based on cleavage of a specific substrate or in an assay using any protein containing substrate with or without a specific inhibitor of serine proteases under suitable conditions.

Serine proteases are generally active at neutral or alkaline pH, with an optimum between pH 7 and 11, and have broad substrate specificity. The "alkaline serine proteases" mean enzymes that are active and stable at pH 9 to pH 11 or even at pH 10 to 12.5 (Shimogaki et al., 1991) and have isoelectric point around pH 9. Those represent the largest subgroup of commercial serine proteases. The molecular masses of alkaline serine proteases range between 15 and 35 kDa. The temperature optima of the natural serine proteases are around 60° C. (Rao et al., 1998).

Microorganism strains capable of producing protease activity can be screened and the activity on different substrates can be determined Chosen strains can be cultivated on a suitable medium. After a sufficient amount of an interesting serine protease has been produced, the enzyme can be isolated or purified and its properties can be more thoroughly characterized. Alternatively, genes encoding serine proteases in various organisms can be isolated and the amino acid sequence encoded by the genes can be compared with the amino acid sequences of the serine protease isolated and characterized in the Examples here.

The produced protease enzymes, particularly the serine proteases can be purified by using conventional methods of enzyme chemistry, such as salt preparation, ultrafiltration, ion exchange chromatography, affinity chromatography, gel filtration and hydrophobic interaction chromatography. Purification can be monitored by protein determination, enzyme activity assays and by SDS polyacrylamide gel electrophoresis. The enzyme activity and stability of the purified enzyme at various temperature and pH values as well as the molecular mass and the isoelectric point can be determined The purification of a preferred serine protease of the present invention has been demonstrated in Example 1b. The filtrated culture supernatant was applied to a Q Sepharose FF column. The flow through fraction was applied to phenyl Sepharose HP column and proteins were eluted with a linear decreasing salt gradient. Fractions showing protease activity were pooled, concentrated and applied to a Superdex 75 10/300 GL column. Purification was followed by activity assays on resorufin-labeled casein as described in Example 1b. Naturally, it is possible to separate the enzyme of the present invention by using other known purification methods instead, or in addition to the methods described herein. The recombinant serine protease was purified as described in Example 5 and used for characterization of pH and temperature profiles.

The molecular mass of the purified serine protease can be determined by mass spectrometry or on SDS-PAGE according to Laemmli (1970). The molecular mass can also be predicted from the amino acid sequence of the enzyme. The mature serine protease or mature serine protease enzyme typically has a molecular mass between 20 to 35 kDa, typically around 25 to 30 kDa (Rao et al., 1998).

The serine proteases are synthesized as inactive "zymogenic precursors" or "zymogens" in the form of a preproenzyme, which are activated by removal of the signal sequence (secretion signal peptide or prepeptide) and the prosequence (propeptide) to yield an active mature form of the enzyme (Chen and Inouye, 2008). This activation process involves action of proteases and may result from limited self-digestive or autocatalytic processing of the serine protease. The prosequence may be cleaved for example during post-translational phases of the production or in the spent culture medium or during the storage of the culture medium or enzyme preparation. Activation of the proenzyme may also be achieved by adding a proteolytic enzyme capable of converting the inactive proenzyme into active mature enzyme into the culture medium where the host organism is cultivated or adding the proteolytic enzyme to the culture supernatant after cultivation process. The shortening of the enzyme can also be achieved e.g. by truncating the gene encoding the polypeptide prior to transforming it to the production host.

The term "mature" means the form of enzyme which after removal of the signal sequence and propeptide comprises the essential amino acids for enzymatic or catalytic activity. In filamentous fungi it is the native form secreted into the culture medium.

The temperature optimum of the serine protease can be determined in a suitable buffer at different temperatures by using casein as a substrate as described in Example 1c and 5 or by using other substrates and buffer systems described in the literature (Gupta et al., 2002). Determination of the pH optimum can be carried out in a suitable buffer at different pH values by following the activity on a protein substrate.

Protease activity is generally based on degradation of soluble substrates. In detergent application proteases have to work on substances which are at least partly insoluble. Thus an important parameter for a detergent protease is the ability to adsorb to and hydrolyse these insoluble fragments.

Another important parameter for selection of detergent proteases is its isoelectric point or pI value. The detergent proteases perform best when the pH value of the detergent solution in which it works is approximately the same as the pI value for the enzyme, pI can be determined by isoelectric focusing on an immobilized pH gradient gel composed of polyacrylamide, starch or agarose or by estimating the pI from the amino acid sequence, for example by using the pI/MW tool at ExPASy server (expasy.org/tools/pi_tool.html; Gasteiger et al., 2003).

The N-terminus of the purified protease as well as internal peptides can be sequenced according to Edman degradation chemistry (Edman and Begg, 1967) as described in Example 2 or by other methods described in the literature.

The serine protease enzyme of the invention may derive from any organism including bacteria, archaea, fungi, yeasts and even higher eukaryote, such as plants. Preferably said enzyme originates from a fungus, including filamentous fungi and yeasts, for example from a genus selected from the group comprising *Fusarium*. Fungal alkaline proteases are advantageous to the bacterial proteases due to the ease of down-stream processing to produce a microbe-free enzyme or enzyme composition. Mycelium can be easily removed through filtration techniques prior to the purification of the enzyme.

The present invention relates to fungal serine protease, which has a good performance in the presence of detergents with highly varying properties, at broad, i.e. from low to moderate temperature ranges, such as 10° C. to 60° C.

In the present invention good performance in presence of detergent means that the enzyme, in this case the fungal serine protease of the invention, functions at lower temperature ranges than many commercial subtilisins presently for sale. In other words, good performance means that the enzyme is capable of degrading or removing proteinaceous stains or material at low to moderate temperature ranges, but especially at lower temperature ranges than the present commercial products, for example the commercial enzyme product Purafect® 4000L (Genencor Inc., USA).

The fungal serine protease of the invention functions at low temperature ranges. For example, by modifying pH, selecting detergents with suitable properties, including enzyme protecting agents and by controlling washing conditions the activity of the serine protease of the invention may be maintained at temperatures as low as 10° C. Therefore, the serine protease of the invention depending on the washing conditions and auxiliary ingredients and additives in detergents is useful particularly in temperatures at or below 50° C. The enzyme functions also at temperatures at or below 45° C., at or below 40° C., at or below 35° C., or at or below 30° C.

In the presence of a detergent, the fungal serine protease of the invention functions as defined above between 10° C. and 60° C. In Examples 6 to 13, comparative experiments are described, and from FIGS. 7 to 17 it is evident that the performance of the fungal serine protease Fe_RF6318 in varying conditions and exposed to varying treatments, on multitude of different stains on different textile material, measured as deltaL* or delta % SR, is by far better than the performance of the commercial products, Savinase® Ultra 16L (Novozymes A/S, DK), Purafect® 4000L (Genencor Inc, USA) and Properase® 4000E (Genencor Inc., USA). Particularly, the stain removal effect of said fungal serine protease Fe_RF6318 in low to moderate temperature ranges such as from 10° C. to 60° C. is remarkably higher than with Savinase® Ultra 16L and Purafect® 4000L. It also has higher stain removal capacity at a range from 30° C. to 60° C. when compared to Properase® 4000E.

From said experimental results it can be concluded that the fungal serine protease of the invention is capable of satisfying the greatly varying demands of detergent customers and detergent industry and industry providing washing machinery and is well suited to the requirements of future regulations and customer habits.

According to a preferred embodiment of the invention the fungal serine protease enzyme is a polypeptide having serine protease activity and comprising the mature enzyme of Fe_RF6318 having the amino acid sequence SEQ ID NO:15 or an amino acid sequence having at least 86% identity to the amino acid sequence SEQ ID NO:15 or at least 86% to the amino acid sequence SEQ ID NO:11. Preferred enzymes show at least 86%, preferably at least 87%, more preferably at least 88%, even more preferably at least 90% identity. Still more preferably the amino acid sequences show at least 92% or at least 94% or 96%, more preferably at least 98%, most preferably 99% identity to the amino acid sequence of SEQ ID NO:15. The identities of the two enzymes are compared within the corresponding sequence regions, e.g. within the mature or full-length region of the serine protease.

The serine protease of the present invention is marked Fe_RF6318, an isolated serine protease originating from *Fusarium equiseti* and is a member of clan SB, family 8 of serine endoproteinases.

By the term "identity" is here meant the identity between two amino acid sequences compared to each other within the corresponding sequence region having approximately the same amount of amino acids. For example, the identity of a full-length or a mature sequence of the two amino acid sequences may be compared. The amino acid sequences of the two molecules to be compared may differ in one or more positions, which however does not alter the biological function or structure of the molecules. Such variation may occur naturally because of different host organisms or mutations in the amino acid sequence or they may be achieved by specific mutagenesis. The variation may result from deletion, substitution, insertion, addition or combination of one or more positions in the amino acid sequence. The identity of the sequences is measured by using ClustalW alignment (e.g. in ebi.ac.uk/Tools/Clustalw). The matrix used is as follows: BLOSUM, Gap open: 10, Gap extension: 0.5.

Preferably, the fungal serine protease is obtainable from *Fusarium*, more preferably from *Fusarium equiseti*. According to the most preferred embodiment the serine protease of the invention is obtainable from the strain deposited at Centraalbureau voor Schimmelcultures under accession number CBS 119568.

One preferred embodiment of the invention is a fungal serine protease enzyme having serine protease activity and an amino acid sequence of the mature Fe_RF6318 enzyme as defined in SEQ ID NO:15. The mature enzyme lacks the signal sequence or prepeptide and the prosequence or propeptide. The mature serine protease of the invention includes amino acids Ala124 to Ala412 of the full length protease characterized in SEQ ID NO:11. Thus, within the scope of the invention is also the full-length Fe_RF6318 enzyme having SEQ ID NO:11 including the signal sequence (prepeptide) and propeptide and the mature enzyme as well as the proenzyme form lacking the signal sequence (prepeptide) thus having SEQ ID NO:13.

The present invention relates to a fungal serine protease enzyme, the mature form of which has a molecular mass or molecular weight between 20 and 35 kDa, preferably between 25 and 33 kDa, more preferably between 28 and 30 kDa. The most preferred MW is the predicted molecular mass of Fe_RF6318 being 29 kDa for the mature polypeptide obtained by using the Compute pI/MW tool at ExPASy server (Gasteiger et al., 2003).

The enzyme of the invention is effective in degrading proteinaceous material at a broad temperature range. The optimal temperature of the enzyme is from 30° C. to 70° C. (about 20% of the maximum activity), preferably from 40° C. to 60° C. (at least about 40% of the maximum activity), and more preferably between 50° C. and 60° C. (at least 70% of the maximum activity), most preferably at 60° C. (the maximum activity, Fe_RF6318) when measured at pH 9 using 15 min reaction time and casein as a substrate as described in Example 5.

According to one preferred embodiment of the invention the fungal serine protease enzyme has pH optimum at a pH range from at least pH 6 to pH 11, showing over 40% of the maximum activity at pH 10 at 50° C. using 15 min reaction time and casein as a substrate as described in Example 5. In particular, the pH optimum is between pH 6 and pH 10 (about 60% of the maximum activity), and more preferably between pH 9 and pH 10 (about 80% of the maximum activity), and most preferably at pH 10 at 50° C.

The fungal serine protease of the invention has "good performance in the presence of detergent", i.e. is capable of degrading or removing proteinaceous stains or material in the presence of detergent at low temperature ranges, specifically at lower temperature ranges than the present commercial products, for example the commercial enzyme product Purafect® 4000L (Genencor Inc., USA). In the presence of a detergent the enzyme of the invention functions between 10° C. and 60° C., preferably at or below 50° C. The Fe_RF6318 enzyme functions also in temperatures at or below 45° C., at or below 40° C., at or below 35° C., or at or below 30° C.

The serine protease enzyme of the invention has pI, which as predicted from the deduced amino acid sequence is between pI 9 and pI 9.5, preferably between pI 9.1 and pI 9.4. The predicted pI of Fe_RF6318 enzyme of the invention is pI 9.3.

Oligonucleotides synthesized on the amino acid sequence of N-terminal or tryptic peptides of the purified enzyme or a PCR product obtained by using the above oligonucleotides can be used as probes in isolation of cDNA or a genomic gene encoding the serine protease of the invention. The probe may be designed also based on the known nucleotide or amino acid sequences of homologous serine proteases. The serine protease clones may also be screened based on activity on plates containing a specific substrate for the enzyme or by using antibodies specific for a serine protease.

According to a preferred embodiment of the invention the fungal serine protease enzyme is encoded by an isolated polynucleotide sequence which hybridizes under stringent conditions with a polynucleotide or probe sequence included in plasmid pALK2521 comprising the nucleotide sequence SEQ ID NO:9 in *E. coli* RF7664, deposited at the Deutsche Sammlung von Mikroorganismen und Zellkulturen (DSMZ) under accession number DSM 22171.

In the present invention the Fe prt8A gene was isolated with a probe prepared by PCR using stringent hybridization as described in Example 3d. Standard molecular biology methods can be used in isolation of cDNA or a genomic DNA of the host organism, e.g. the methods described in the molecular biology handbooks, such as Sambrook and Russell, 2001.

Hybridization with a DNA probe, such as for example SEQ ID NO:9 consisting of more than 100-200 nucleotides, is usually performed at "high stringency" conditions, i.e. hybridization at a temperature, which is 20-25° C. below the calculated melting temperature (Tm) of a perfect hybrid, the Tm calculated according to Bolton and McCarthy (1962). Usually prehybridization and hybridization are performed at least at 65° C. in 6×SSC (or 6×SSPE), 5×Denhardt's reagent, 0.5% (w/v) SDS, 100 µg/ml denatured, fragmented salmon sperm DNA. Addition of 50% formamide lowers the prehybridization and hybridization temperatures to 42° C. Washes are performed in low salt concentration, e.g. in 2×SSC-0.5% SDS (w/v) for 15 minutes at room temperature (RT), followed in 2×SSC-0.1% SDS (w/v) at RT, and finally in 0.1×SSC-0.1% SDS (w/v) at least at 65° C.

According to one preferred embodiment the fungal serine protease enzyme of the invention is encoded by an isolated nucleic acid molecule, which encodes a polypeptide comprising the amino acid sequence characterized in SEQ ID NO:15, or a polypeptide having at least 86% to the amino acid sequence SEQ ID NO:15 or at least 86% to the amino acid sequence SEQ ID NO:11. Preferred enzymes show at least 86%, preferably at least 87%, more preferably at least 88%, even more preferably at least 90% identity. Still more preferably the amino acid sequences show at least 92% or at least 94% or 96%, more preferably at least 98%, most preferably 99% identity to the amino acid sequence of SEQ ID NO:15. The identities of the two enzymes are compared within the corresponding sequence regions, e.g. within the mature or full-length region of the serine protease.

Thus, within the scope of the invention is a polypeptide sequence, which is encoded by a nucleic acid molecule encoding the amino acid sequence of the full-length serine protease of the invention including the prepeptide (signal sequence) and the propeptide in addition to the mature form of the enzyme, and which amino acid sequence is characterized in SEQ ID NO:11.

Also, within the scope of the invention is a polypeptide sequence, which is encoded by a nucleic acid molecule encoding the propeptide of serine protease enzyme of the invention including the propeptide in addition to the mature form of the enzyme, and which amino acid sequence is characterized in SEQ ID NO:13.

One preferred embodiment of the invention is the fungal serine protease enzyme encoded by an isolated nucleic acid molecule, which comprises the nucleotide sequence encoding the mature form of the Fe_RF6318 serine protease having SEQ ID NO:15.

According to one preferred embodiment the fungal serine protease enzyme of the invention is encoded by an isolated nucleic acid molecule comprising the nucleotide sequence SEQ ID NO:14 encoding the mature form of the Fe_RF6318 enzyme (SEQ ID NO:15).

Thus, within the scope of the invention is the polypeptide encoded by the nucleic acid molecule having the nucleotide sequence SEQ ID NO:10 comprising the "coding sequence" for the enzyme. The expression "coding sequence" means the nucleotide sequence which initiates from the translation start codon (ATG) and stops at the translation stop codon (TAA, TAG or TGA). The translated full-length polypeptide starts usually with methionine and comprises intron regions.

Also, within the scope of the invention is a fungal serine protease enzyme encoded by a nucleic acid molecule comprising the nucleotide sequence SEQ ID NO:12, which encodes the FeRF6318 proenzyme form.

According to another preferred embodiment of the invention the fungal serine protease is encoded by the polynucleotide sequence included in pALK2529 deposited in *E. coli* RF7800 under accession number DSM 22172.

One embodiment of the invention is the serine protease enzyme produced from a recombinant expression vector comprising the nucleic acid molecule, which encodes the fungal serine protease enzyme as characterized above operably linked to regulatory sequences capable of directing the expression of said serine protease encoding gene in a suitable host. Construction of said recombinant expression vector and use of said vector is described in more detail in Example 4.

Suitable hosts for production of the fungal serine protease enzyme are homologous or heterologous hosts, such as the microbial hosts including bacteria, yeasts and fungi. Filamentous fungi, such as *Trichoderma, Aspergillus, Fusarium, Humicola, Chrysosporium, Neurospora, Rhizopus, Penicillium* and *Mortiriella*, are preferred production hosts due to the ease of down-stream processing and recovery of the enzyme product. Suitable hosts include species such as *T. reesei, A. niger, A. oryzae, A. sojae, A. awamori* or *A. japonicus* type of strains, *F. venenatum* or *F. oxysporum, H. insolens* or *H. lanuginosa, N. crassa* and *C. lucknowense*, some of which are listed as enzyme production host organisms in e.g. AMFEP 2007 list of commercial enzymes (amfep.org/list.html). More preferably, the enzyme is produced in a filamentous fungal host of the genus *Trichoderma* or *Aspergillus*, such as *T. reesei* or *A. niger, A. oryzae* or *A. awamori*. According the most preferred embodiment of the invention the fungal serine protease enzyme is produced in *T. reesei*.

The present invention relates also to an isolated nucleic acid molecule encoding the fungal serine protease enzyme selected from the group consisting of:

(a) a nucleic acid molecule encoding a polypeptide having serine protease activity and comprising the amino acid sequence as depicted in SEQ ID NO:15;

(b) a nucleic acid molecule encoding a polypeptide having serine protease activity and at least 86% to SEQ ID NO:15;

(c) a nucleic acid molecule comprising the coding sequence of the nucleotide sequence as depicted in SEQ ID NO: 10;

(d) a nucleic acid molecule comprising the coding sequence of the polynucleotide sequence contained in DSM 22171 or DSM 22172;

(e) a nucleic acid molecule the coding sequence of which differs from the coding sequence of a nucleic acid molecule of any one of (c) to (d) due to the degeneracy of the genetic code; and (f) a nucleic acid molecule hybridizing under stringent conditions with a nucleic acid molecule contained in DSM 22171, and encoding a polypeptide having serine protease activity and an amino acid sequence which shows at least 86% identity to the amino acid sequence as depicted in SEQ ID NO:15.

The nucleic acid molecule of the invention may be RNA or DNA, wherein the DNA may constitute of the genomic DNA or cDNA.

Standard molecular biology methods can be used in isolation and enzyme treatments of the polynucleotide sequence encoding the fungal serine protease of the invention, including isolation of genomic and plasmid DNA, digestion of DNA to produce DNA fragments, sequencing, *E. coli* transformations etc. The basic methods are described in the standard molecular biology handbooks, e.g. Sambrook and Russell, 2001.

Isolation of the Fe prtS8A gene encoding the Fe_RF6318 polypeptide is described in Example 3. Briefly, the 866 bp PCR fragment obtained by using the sequences of the degenerate oligonucleotide primers (SEQ ID NO: 6 and SEQ ID NO: 7) was used to isolate the Fe prt8A from *Fusarium equiseti* RF6318 in pBluescript II KS+ vector. The full-length *Fusarium equiseti* Fe prtS8A gene was included in the plasmid pALK2529 deposited in *E. coli* to the DSMZ culture collection under accession number DSM 22172. The deduced amino acid sequence of the serine protease was analysed from the DNA sequence.

The nucleotide sequence of *Fusarium equiseti* serine protease Fe prtS8A (SEQ ID NO: 10) and the deduced sequence (SEQ ID NO:11) are presented in FIG. 1A-B. The length of the gene is 1303 bp (including the stop codon). One putative intron was found having the length of 64 bps. The deduced protein sequence consists of 412 amino acids including a predicted signal sequence of 20 amino acids (SignalP V3.0; Nielsen et al., 1997 and Nielsen and Krogh, 1998) and a propeptide from Ala21 to Arg123. The peptides purified from the wild type Fe_RF6318 matched the deduced amino acid sequence indicating that the gene cloned encodes the protease purified from the *Fusarium equiseti* host RF6318 deposited to the CBS culture collection under accession number CBS119568. The predicted molecular mass was 29 kpa for the mature polypeptide and the predicted pI was 9.30. These predictions were made using the Compute pI/MW tool at ExPASy server (Gasteiger et al., 2003). The deduced amino acid sequence contained two possible N-glycosylation sites (Asn77 and Asn255), but according to CBS Server NetNGlyc V1.0 only one site, Asn77 (located in the pro sequence) is probable. The homologies to the published protease sequences were searched using the BLAST program, version 2.2.9 at NCBI (National Center for Biotechnology Information) (Altschul et al., 1990). The identity values of the mature Fe_RF6318 sequence to the corresponding regions of homologous sequences were obtained by using ClustalW alignment (Matrix: BLOSUM, Gap open: 10, Gap extension: 0.5 (e.g. in ebi.ac.uk/Tools/Clustalw) are shown in Table 3.

The serine protease Fe_RF6318 of the present invention showed highest homology to *Gibberella zeae* hypothetical protein PH-1, locus tag FG03315.1 (EMBL accession no. XP_383491, unpublished), to *T. harzianum* CECT 2413 serine endopeptidase (EMBL accession no. CAL25580, Suarez et al., 2007) and to *T. atroviride* alkaline proteinase precursor S08.066, ALP (EMBL accession no. M87516, Geremia et al. 1993), the latter disclosed as an amino acid sequence SEQ ID NO:313 in U.S. 60/818,910 (Catalyst Bioscience Inc.). The identity to *G. zeae* hypothetical protein was within the full-length enzyme 85%. When the mature polypeptides lacking the signal sequence and propeptide were aligned, the identity was 85%. Identity to *T. harzianum* CECT 2413 serine endopeptidase was 70% (full-length enzyme) and 75% (mature enzyme). The identity to *T. atroviride* ALP was 69% (full-length enzyme) and 74% (mature enzyme).

Thus, within the scope of the invention is an isolated polynucleotide sequence or isolated nucleic acid molecule, which encodes a fungal serine protease enzyme or polypeptide comprising the amino acid sequence of the mature form of the Fe_RF6318 enzyme characterized in SEQ ID NO: 15, i.e. amino acids Ala124 to Ala412 of the full length serine protease of SEQ ID NO:11.

Further, within the scope of the present invention are nucleic acid molecules which encode a fragment of a fungal serine protease polypeptide, wherein the fragment has serine protease activity and has at least 86% identity to the amino acid sequence SEQ ID No:15 or at least 86% to the amino acid sequence SEQ ID NO:11. Preferred enzymes show at least 86%, preferably at least 87%, more preferably at least 88%, even more preferably at least 90% identity. Still more preferably the amino acid sequences show at least 92% or at least 94% or 96%, more preferably at least 98%, most preferably 99% identity to the amino acid sequence of SEQ ID NO:15. The identities of the two enzymes are compared within the corresponding sequence regions, e.g. within the full-length or mature region of the serine protease.

The nucleic acid molecule is preferably a molecule comprising the coding sequence as depicted in SEQ ID NO:10, which encodes the full length form of the fungal serine protease enzyme of this invention.

The isolated nucleic acid molecule of the invention may be a molecule comprising the coding sequence of the polynucleotide sequence contained in DSM 22171 or DSM 22172. DSM 22171 carries the nucleotide sequence of the PCR fragment (SEQ ID NO:9) used in cloning the full length Fe prtS8A gene. DSM 22172 carries the nucleotide sequence of the full length Fe prtS8A gene (SEQ ID NO:10).

The nucleic acid molecule of the invention may also be an analogue of the nucleotide sequence characterized in above. The "degeneracy" means analogues of the nucleotide sequence, which differ in one or more nucleotides or codons, but which encode the recombinant protease of the invention.

The nucleic acid molecule may also be a nucleic acid molecule hybridizing under stringent conditions to a PCR probe contained in plasmid pALK2521 deposited in *E. coli* under the accession number DSM 22171 and encoding a polypeptide having serine protease activity and an amino acid sequence which within the corresponding sequence region shows at least 86% identity to the amino acid sequence as depicted in SEQ ID NO:15. The hybridizing DNA may originate from a fungus belonging to species *Fusarium* or it may originate from other fungal species.

Thus, within the scope of the invention is an isolated nucleic acid molecule comprising a nucleotide sequence as depicted in SEQ ID NO:10, SEQ ID NO:12 or SEQ ID NO:14 and analogues thereof.

The present invention relates also to a recombinant expression vector or recombinant expression construct, which can be used to propagate or express the nucleic acid sequence encoding the chosen serine protease in a suitable prokaryotic or eukaryotic host. The recombinant expression vector comprises DNA or nucleic acid sequences which facilitate or direct expression and secretion of the serine protease encoding sequence in a suitable host, such as promoters, enhancers, terminators (including transcription and translation termination signals) and signal sequences operably linked the polynucleotide sequence encoding said serine protease. The expression vector may further comprise marker genes for selection of the transformant strains or the selection marker may be introduced to the host in another vector construct by co-transformation. Said regulatory sequences may be homologous or heterologous to the production organism or they may originate from the organism, from which the gene encoding the serine protease is isolated.

Examples of promoters for expressing the serine protease of the invention in filamentous fungal hosts are the promoters of *A. oryzae* TAKA amylase, alkaline protease ALP and triose phosphate isomerase, *Rhizopus miehei* lipase, *Aspergillus niger* or *A. awamori* glucoamylase (glaA), *Fusarium oxysporum* trypsin-like protease, *Chrysosporium lucknowense* cellobiohydrolase 1 promoter, *Trichoderma reesei* cellobiohydrolase I (Cel7A) etc.

In yeast, for example promoters of *S. cerevisiae* enolase (ENO-1), galactokinase (GAL1), alcohol dehydrogenase (ADH2) and 3-phosphoglycerate kinase can be used to provide expression.

Examples of promoter sequences for directing the transcription of the serine protease of the invention in a bacterial host are the promoter of lac operon of *Escherichia coli*, the *Streptomyces coelicolor* agarase dagA promoter, the promoter of the *B. licheniformis* alpha-amylase gene (amyL), the promoter of the *B. stearothermophilus* maltogenic amylase gene (amyM), the promoters of the *B. sublitis* xylA and xylB genes, etc.

Suitable terminators include those of the above mentioned genes or any other characterized terminator sequences.

Suitable transformation or selection markers include those which complement a defect in the host, for example the dal genes from *B. subtilis* or *B. licheniformis* or *Aspergillus* amdS and niaD. The selection may be based also on a marker conferring antibiotic resistance, such as ampicillin, kanamycin, chloramphenicol, tetracycline, phleomycin or hygromycin resistance.

Extracellular secretion of the serine protease of the invention is preferable. Thus, the recombinant vector comprises sequences facilitating secretion in the selected host. The signal sequence of the serine protease of the invention or the presequence or prepeptide may be included in the recombinant expression vector or the natural signal sequence may be replaced with another signal sequence capable of facilitating secretion in the selected host. Thus, the chosen signal sequence may be homologous or heterologous to the expression host.

Examples of suitable signal sequences are those of the fungal or yeast organisms, e.g. signal sequences from well expressed genes. Such signal sequences are well known from the literature.

The recombinant vector may further comprise sequences facilitating integration of the vector into the host chromosomal DNA to obtain stable expression.

The Fe_RF6318 protease of the invention was expressed with its own signal sequence from the *T. reesei* cbh1 (cel7A) promoter as described in Example 4. The expression construct used to transform the *T. reesei* host included also cbh1 terminator and amdS marker for selecting the transformants from the untrasformed cells.

The present invention relates also to host cells comprising the recombinant expression vector as described above. Suitable hosts for production of the fungal serine protease enzyme are homologous or heterologous hosts, such as the microbial hosts including bacteria, yeasts and fungi. Production systems in plant or mammalian cells are also possible.

Filamentous fungi, such *Trichoderma, Aspergillus, Fusarium, Humicola, Chrysosporium, Neurospora, Rhizopus, Penicillium* and *Mortiriella*, are preferred production hosts due to the ease of down-stream processing and recovery of the enzyme product. Suitable expression and production host systems are for example the production system developed for the filamentous fungus host *Trichoderma reesei* (EP 244234), or *Aspergillus* production systems, such as *A. oryzae* or *A. niger* (WO 9708325, U.S. Pat. No. 5,843,745, U.S. Pat. No. 5,770,418), *A. awamori, A. sojae* and *A. japonicus*-type strains, or the production system developed for *Fusarium*, such as *F. oxysporum* (Malardier et al., 1989) or *F. venenatum*, and for *Neurospora crassa, Rhizopus miehei, Mortiriella alpinis, H. lanuginosa* or *H. insolens* or for *Chrysosporium lucknowense* (U.S. Pat. No. 6,573,086). Suitable production systems developed for yeasts are systems developed for *Saccharomyces, Schizosaccharomyces* or *Pichia pastoris*. Suitable production systems developed for bacteria are a production system developed for *Bacillus*, for example for *B. subtilis, B. licheniformis, B. amyloliquefaciens*, for *E. coli*, or for the actinomycete *Streptomyces*. Preferably the serine protease of the invention is produced in a filamentous fungal host of the genus *Trichoderma* or *Aspergillus*, such as *T. reesei*, or *A. niger, A. oryzae, A. sojae, A. awamori* or *A. japonicus-type* strains. According the most preferred embodiment of the invention the fungal serine protease enzyme is produced in *T. reesei*.

The production host cell may be homologous or heterologous to the serine protease of the invention. The host may be free of homogenous proteases due to removal of proteases either by inactivation or removal of one or more host proteases, e.g. by deletion of the gene(s) encoding such homogenous or homologous proteases.

The present invention relates also to a process for producing a polypeptide having serine protease activity, said process comprising the steps of culturing the natural or recombinant host cell carrying the recombinant expression vector for a serine protease of the invention under suitable conditions and optionally isolating said enzyme. The production medium may be a medium suitable for growing the host organism and containing inducers for efficient expression. Suitable media are well-known from the literature.

The invention relates to a polypeptide having serine protease activity, said polypeptide being encoded by the nucleic acid molecule of the invention and which is obtainable by the process described above. Preferably, the polypeptide is a recombinant protease enzyme obtained by culturing the host cell carrying the recombinant expression vector for a serine protease of the invention.

The invention further relates to a process for obtaining an enzyme preparation comprising a polypeptide, which has serine protease activity, said process comprising the steps of culturing a host cell carrying the expression vector of the invention and either recovering the polypeptide from the cells or separating the cells from the culture medium and obtaining the supernatant having serine protease activity.

The present invention relates also to an enzyme preparation, which comprises the serine protease enzyme characterized above. The enzyme preparation or composition has serine protease activity and is obtainable by the process according to the invention.

Within the invention is an enzyme preparation which comprises the fungal serine protease of the invention, preferably the recombinant serine protease obtained by culturing a host cell, which carries the recombinant expression vector of the invention.

Said enzyme preparation may further comprise different types of enzymes in addition to the serine protease of this invention, for example another protease, an amylase, a lipase, a cellulase, cutinase, a pectinase, a mannanase, a xylanase and/or an oxidase such as a laccase or peroxidase with or without a mediator. These enzymes are expected to enhance the performance of the serine proteases of the invention by removing the carbohydrates and oils or fats present in the material to be handled. Said enzymes may be natural or recombinant enzymes produced by the host strain or may be added to the culture supernatant after the production process.

Said enzyme preparation may further comprise a suitable additive selected from the group of surfactants or surface active agent, buffers, anti-corrosion agents, stabilizers, bleaching agents, mediators, builders, caustics, abrasives and preservatives, optical brighteners, antiredeposition agents, dyes, pigments, etc.

Surfactants are useful in emulsifying grease and wetting surfaces. The surfactant may be a non-ionic including semipolar and/or anionic and/or cationic and/or zwitterionic.

Buffers may be added to the enzyme preparation to modify pH or affect performance or stability of other ingredients.

Suitable stabilizers include polyols such as propylene glycol or glycerol, a sugar or sugar alcohol, lactic acid, boric acid, or boric acid derivatives, peptides, etc.

Bleaching agent is used to oxidize and degrade organic compounds. Examples of suitable chemical bleaching systems are $H_2O_2$ sources, such as perborate or percarbonate with or without peracid-forming bleach activators such as tetraacetylethylenediamine, or alternatively peroxyacids, e.g. amide, imide or sulfone type. Chemical oxidizers may be replaced partially or completely by using oxidizing enzymes, such as laccases or peroxidases. Many laccases do not function effectively in the absence of mediators.

Builders or complexing agents include substances, such as zeolite, diphosphate, triphosphate, carbonate, citrate, etc. The enzyme preparation may further comprise one or more polymers, such as carboxymethylcellulose, poly(ethylene glycol), poly(vinyl alcohol), poly(vinylpyrrolidone), etc. Also, softeners, caustics, preservatives for preventing spoilage of other ingredients, abrasives and substances modifying the foaming and viscosity properties can be added.

According to one preferred embodiment of the invention said enzyme preparation is in the form of liquid, powder or granulate.

The fungal serine protease of the present invention may like other proteases, particularly alkaline proteases be used in the detergent, protein, brewing, meat, photographic, leather, dairy and pharmaceutical industries (Kalisz, 1988; Rao et al., 1998). For example, it may be used as an alternative to chemicals to convert fibrous protein waste (e.g. horn, feather, nails and hair) to useful biomass, protein concentrate or amino acids (Anwar and Saleemuddin, 1998). The use of fungal serine protease of the present invention may like other enzymes prove successful in improving leather quality and in reducing environmental pollution and saving energy and it may like alkaline proteases be useful in synthesis of peptides and resolution of the mixture of D,L-amino acids. Subtilisin in combination with broad-spectrum antibiotics in the treatment of burns and wounds is an example of the use of serine proteases in pharmaceutical industry, therefore the fungal serine protease of the present invention may also find such use and may also like alkaline proteases be applicable in removal of blood on surgical equipments and cleaning contact lenses or dentures. Like alkaline protease from *Conidiobolus coronatus*, the fungal serine protease of the present invention may be used for replacing trypsin in animal cell cultures. The proteases of the invention can also be used in cleaning of membranes and destruction of biofilms. In baking the proteases can be used e.g. in destruction of the gluten network and in other food applications in hydrolysis of food proteins, e.g proteins in milk. They can also be used e.g. in treating yeast, rendering (extracting more protein from animal bones), creating new flavours, reducing bitterness, changing emulsifying properties, generating bioactive peptides and reducing allergenicity of proteins. The substrates include animal, plant and microbial proteins.

Detergent industry, particularly the laundry detergent industry, has emerged as the single major consumer of proteases active at high pH range (Anwar and Saleemuddin, 1998). The ideal detergent protease should possess broad substrate specificity to facilitate the removal of large variety of stains due to food, grass, blood and other body secretions. It has to be active in the pH and ionic strength of the detergent solution, the washing temperature and pH, and tolerate mechanical handling as well as the chelating and oxidizing agents added to detergents. The pI of the protease must be near the pH of the detergent solution. Due to present energy crisis and the awareness for energy conservation, it is currently desirable to use the protease at lower temperatures.

The present invention relates also to the use of the serine protease enzyme or the enzyme preparation for detergents, treating textile fibers, for treating wool, for treating hair, for treating leather, for treating feed or food, or for any application involving modification, degradation or removal of proteinaceous material.

One preferred embodiment of the invention is therefore the use of the serine protease enzyme as characterized above as a detergent additive useful for laundry detergent and dish wash compositions, including automatic dish washing compositions.

The expression "detergent" is used to mean substance or material intended to assist cleaning or having cleaning properties. The term "detergency" indicates presence or degree of cleaning property. The degree of cleaning property can be tested on different proteinaceous or protein containing substrate materials or stains or stain mixtures bound to solid, water-insoluble carrier, such as textile fibers or glass. Typical proteinaceous material includes blood, milk, ink, egg, grass and sauces. For testing purposes mixtures of proteinaceous stains are commercially available. The function of the detergent enzyme is to degrade and remove the protein-containing stains. Test results depend on the type of stain, the composition of the detergent and the nature and status of textiles used in the washing test (Maurer, 2004).

Typically, the protease or wash performance is measured as "stain removal efficiency" or "stain removal effect" or "degree of cleaning property", meaning a visible and measurable increase of lightness or change in colour of the stained material, e.g. in artificially soiled swatches or test cloths. Lightness or change in colour values can be measured, for example by measuring the colour as reflectance values with a spectrophotometer using L*a*b* colour space coordinates as described in Examples 6 to 10. Fading or removal of proteinaceous stain indicating of the protease performance (stain removal efficiency) is calculated for example as ΔL*, which means lightness value L* of enzyme treated fabric minus lightness value L* of fabric treated with buffer or washing liquor without enzyme (enzyme blank or control). The presence of detergent may improve the performance of the enzyme in removing the stains.

The serine protease of the present invention degrades various kinds of proteinaceous stains under conditions of neutral and alkaline pH and even in the presence of detergents with different compositions (as shown in Examples 6 to 13).

Figure 5:
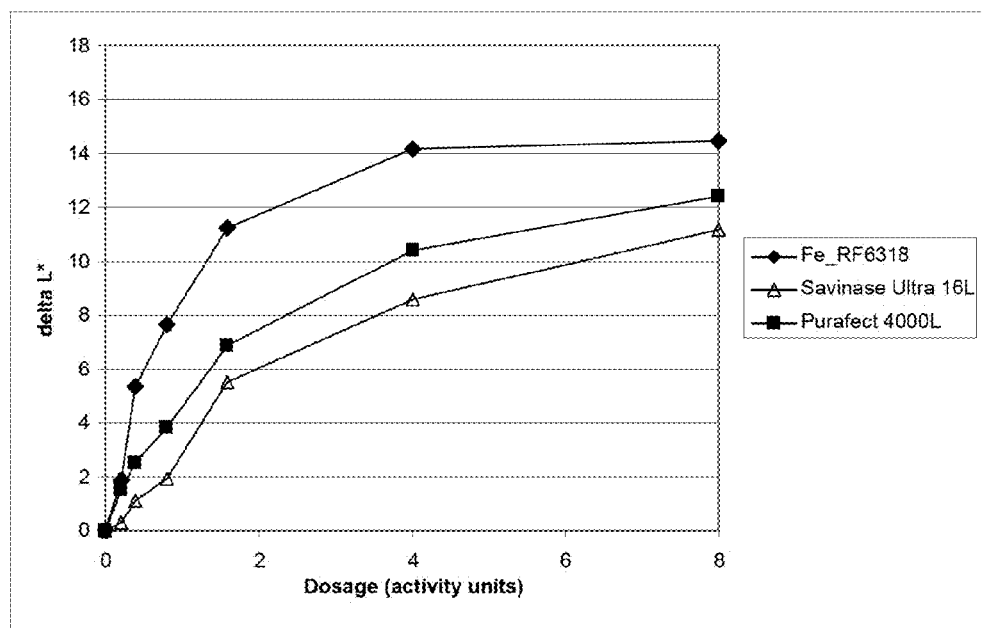
FIG. 5 describes the performance of recombinant Fe_RF6318 protein with blood/milk/ink stain (Art. 116, EMPA) at 30° C., pH 9, 60 min. Commercial preparations Savinase Ultra® 16L (Novozymes A/S, DK) and Purafect® 4000L (Genencor Inc., USA) were used for comparison. ΔL* (deltaL*)=lightness value L* of enzyme treated fabric–lightness value L* of fabric treated with buffer only (enzyme blank).
Figure 6:
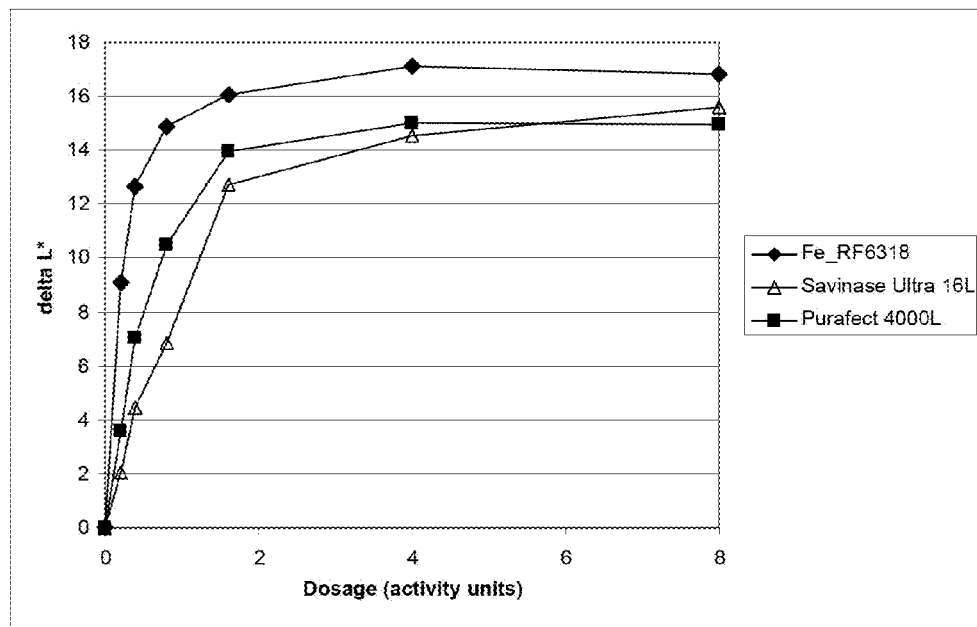
FIG. 6 describes the performance of recombinant Fe_RF6318 protein with blood/milk/ink stain (Art. 116, EMPA) at 50° C., pH 9, 60 min. Commercial preparations Savinase® Ultra 16L and Purafect® 4000L were used for comparison. ΔL* (deltaL*)=lightness value L* of enzyme treated fabric–lightness value L* of fabric treated with buffer only (enzyme blank).
Figure 7A:
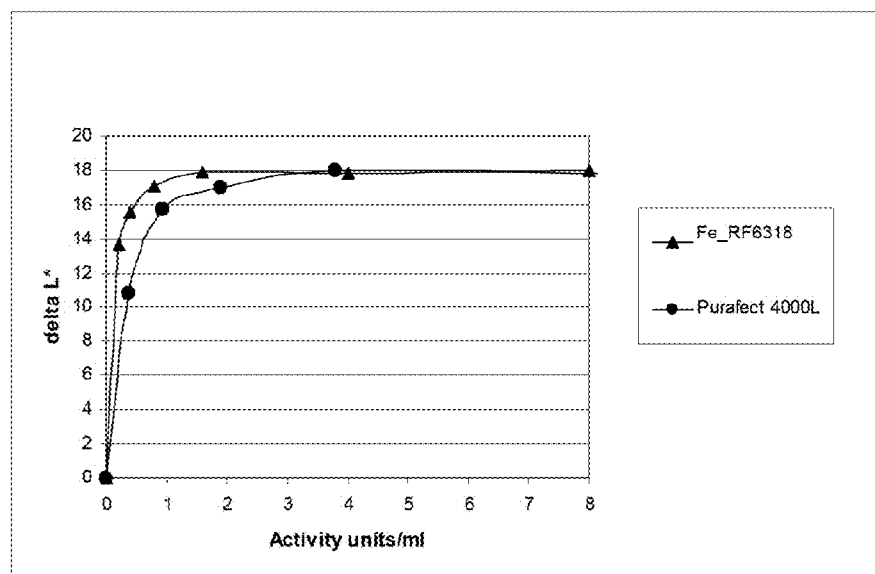
FIG. 7A describes the performance of recombinant Fe_RF6318 protein with blood/milk/ink stain (Art 117, EMPA) at 40° C., approximately at pH 10, 60 min in the presence of detergent powder (Art. 601, EMPA). Commercial preparation Purafect® 4000L was used for comparison. ΔL* (deltaL*)=lightness value L* of enzyme treated fabric–lightness value L* of fabric treated with buffer only (enzyme blank).
Figure 7B:
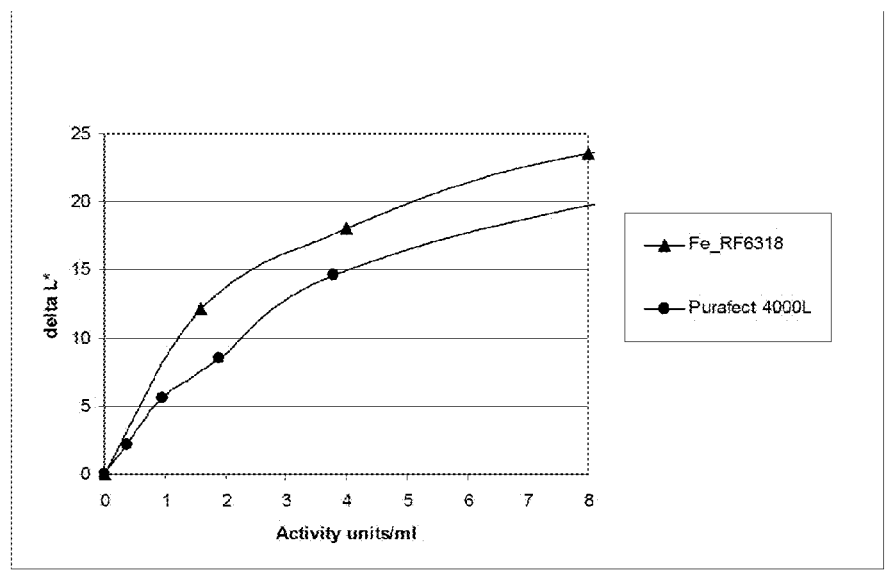
FIG. 7B describes the performance of recombinant Fe_RF6318 protein with blood/milk/ink stain (Art 117, EMPA) at 40° C., approx. at pH 10, 60 min in the presence of detergent powder and bleaching agents (Art. 604 and 606, EMPA). Commercial preparation Purafect® 4000L was used for comparison. ΔL* (deltaL*)=lightness value L* of enzyme treated fabric–lightness value L* of fabric treated with buffer only (enzyme blank).
Figure 8A:
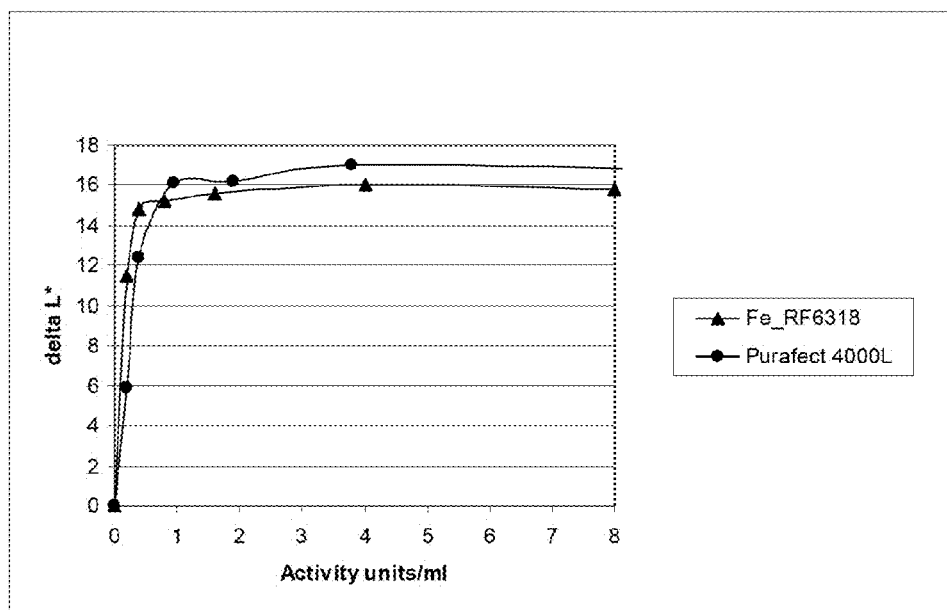
FIG. 8A describes the performance of recombinant Fe_RF6318 protein with blood/milk/ink stain (Art 117, EMPA) at 50° C., approx. at pH 10, 60 min in the presence of detergent powder (Art. 601, EMPA). Commercial preparation Purafect® 4000L was used for comparison. ΔL* (deltaL*)=lightness value L* of enzyme treated fabric–lightness value L* of fabric treated with buffer only (enzyme blank).
Figure 8B:
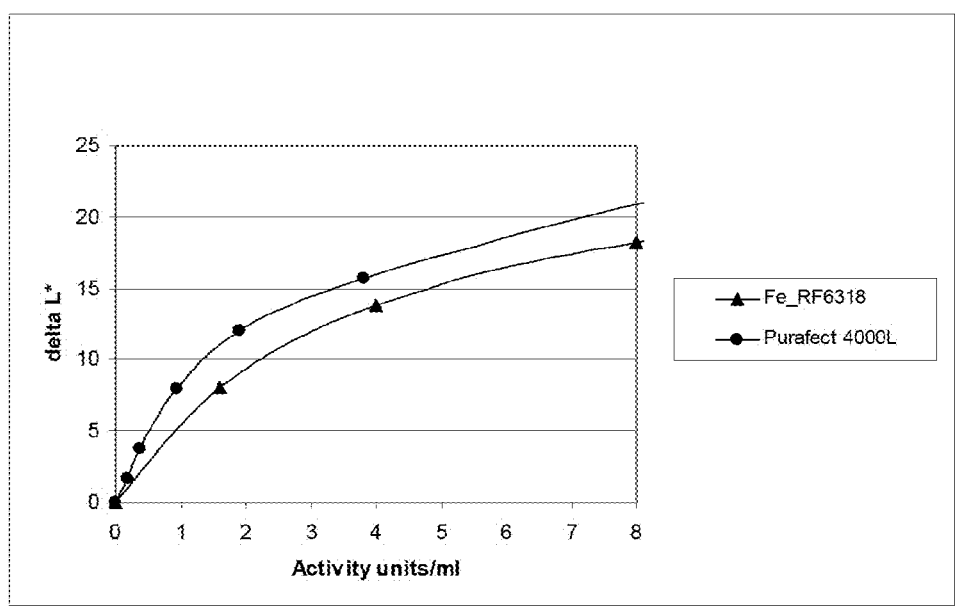
FIG. 8B describes the performance of recombinant Fe_RF6318 protein with blood/milk/ink stain (Art 117, EMPA) at 50° C., approx. at pH 10, 60 min in the presence of detergent powder and bleaching agents (Art. 604 and 606, EMPA). Commercial preparation Purafect® 4000L was used for comparison. ΔL* (deltaL*)=lightness value L* of enzyme treated fabric–lightness value L* of fabric treated with buffer only (enzyme blank).

As shown in Example 6 the serine protease of the invention removed the blood/milk/ink stain at 50° C. and especially at 30° C. in pH 9 buffer better than the commercial protease preparations Savinase® Ultra 16L and Purafect® 4000L (FIGS. 5 and 6). The enzyme preparations were dosed as activity units. The stain removal effect on blood/milk/ink stain was tested also at the whole temperature range from 10° C. to 60° C. as described in Example 12. Fe_RF6318 protease preparation showed higher stain removal capacity compared to the commercial protease preparation Savinase® Ultra 16L and Purafect® 4000L. It also showed higher stain removal capacity at a range from 30° C. to 60° C. compared to Properase® 4000E (FIG. 16).

The performance of the Fe_RF6318 protease was tested also in detergent powder at 40° C./50° C. at pH 10 as described in Example 7. The ability of the enzyme in removing blood/milk/ink stain on polyester-cotton material was assayed. Each enzyme preparation was dosed as activity units (μmol tyrosine/minute). As shown in FIGS. 7 and 8 the protease of the invention is suitable also for powder detergents at very alkaline conditions and its resistance for bleaching agents was slightly higher than with commercial protease Purafect® 4000L.

Figure 10A:
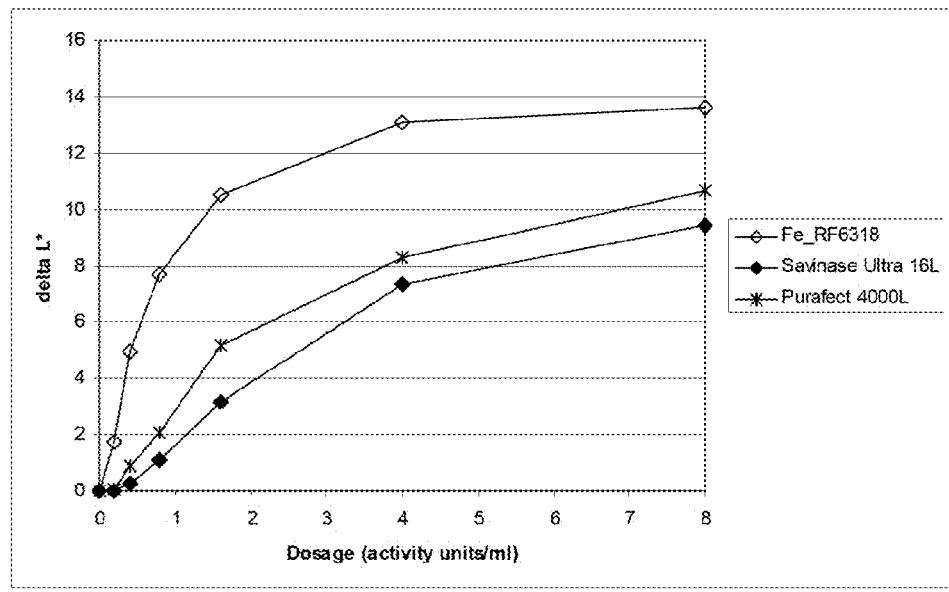
FIGS. 10A-D show the performance of recombinant Fe_RF6318 protein with blood/milk/ink stain (Art 117, EMPA) with different concentrations of liquid base detergent for coloured fabrics at 30° C. Commercial preparations Purafect® 4000L and Savinase® Ultra 16L were used for comparison. ΔL* (deltaL*)=lightness value L* of enzyme treated fabric–lightness value L* of fabric treated with buffer only (enzyme blank).
Figure 10B:
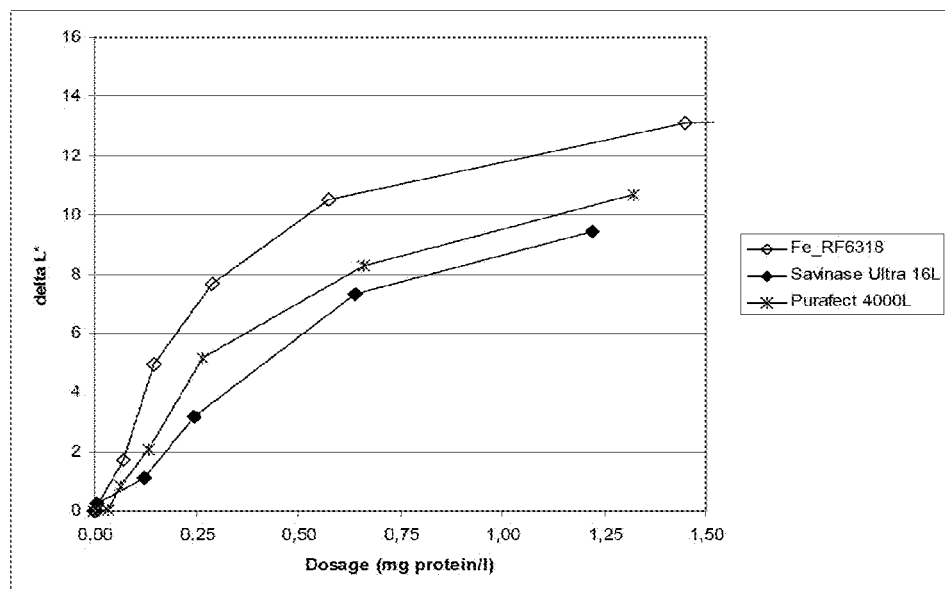
Figure 10C:
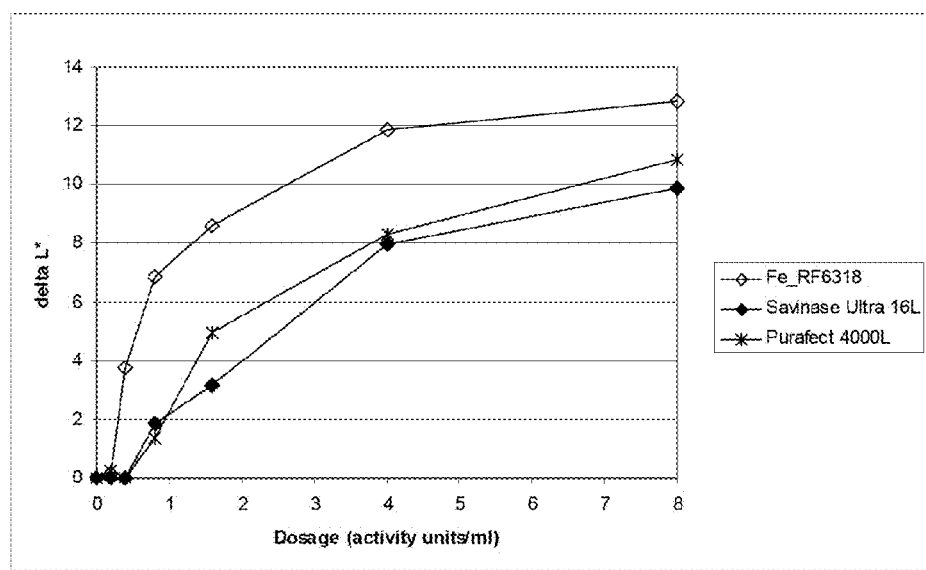
Figure 10D:
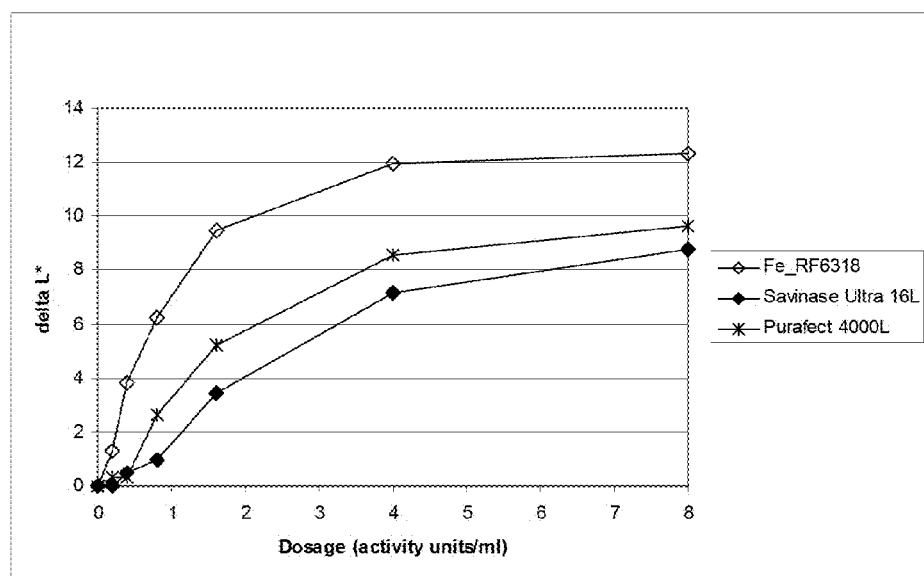
Figure 11A:
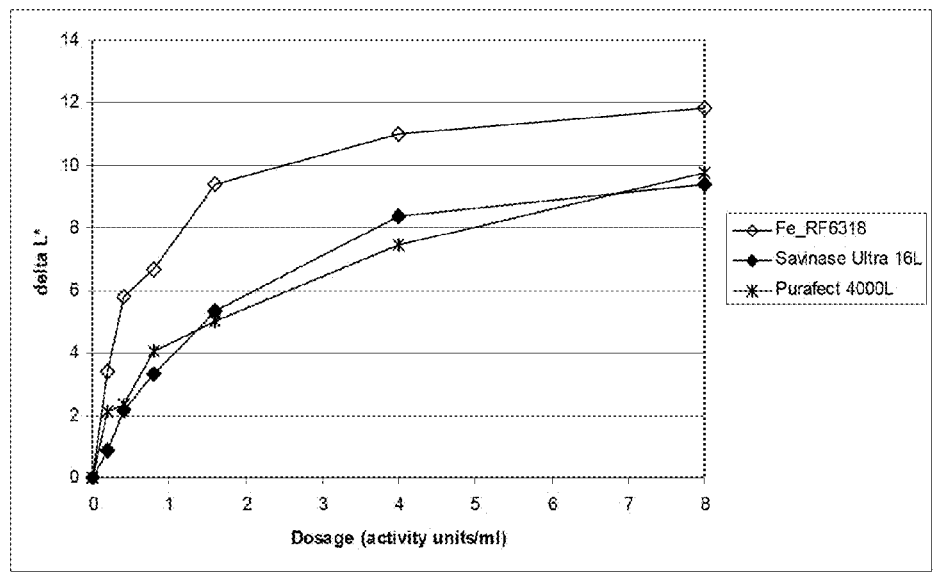
FIGS. 11A-D show the performance of recombinant protein Fe_RF6318 with blood/milk/ink stain (Art 117, EMPA) with different concentrations of Ariel Sensitive (without enzymes) on fabrics at 30° C. Commercial preparations Purafect® 4000L and Savinase® Ultra 16L were used for comparison. ΔL* (deltaL*)=lightness value L* of enzyme treated fabric–lightness value L* of fabric treated with buffer only (enzyme blank).
Figure 11B:
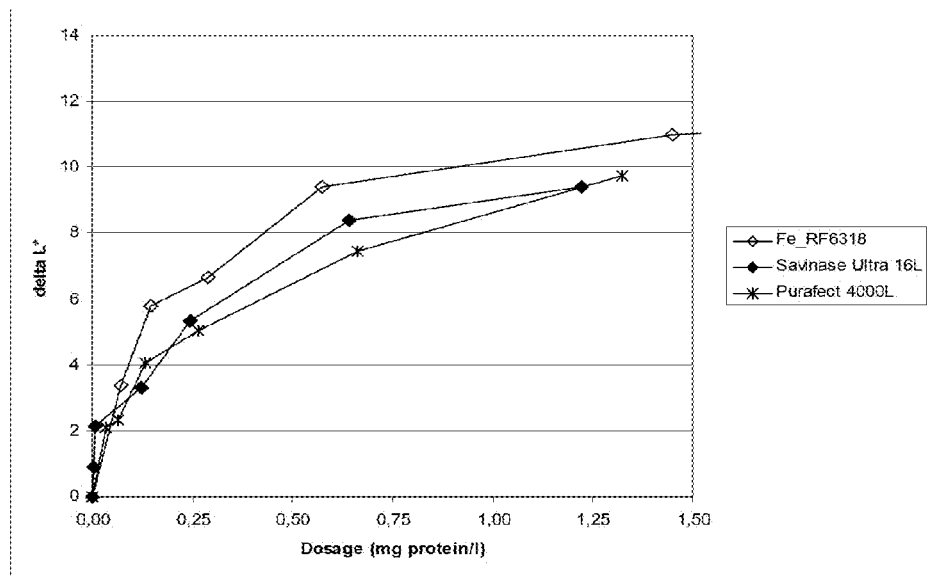
Figure 11C:
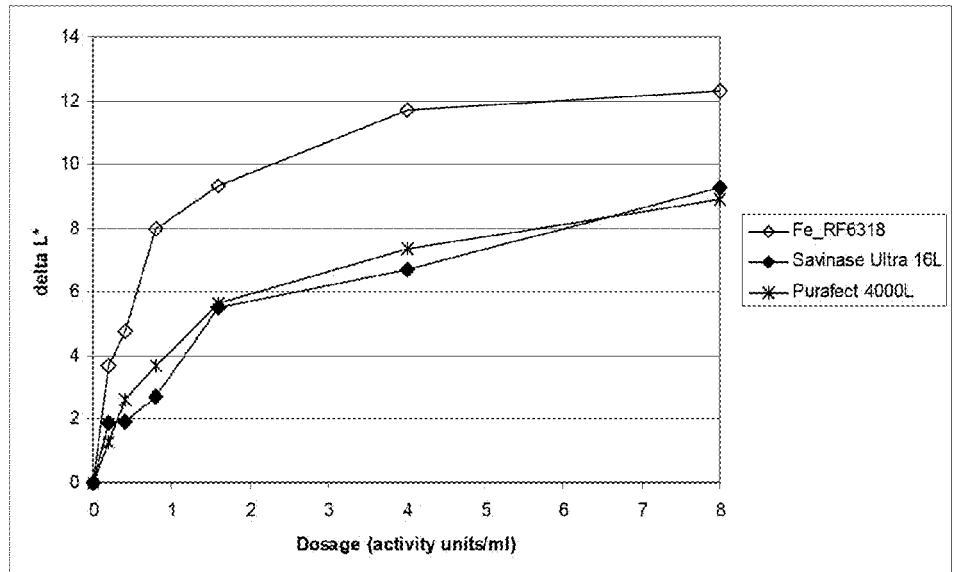
Figure 11D:
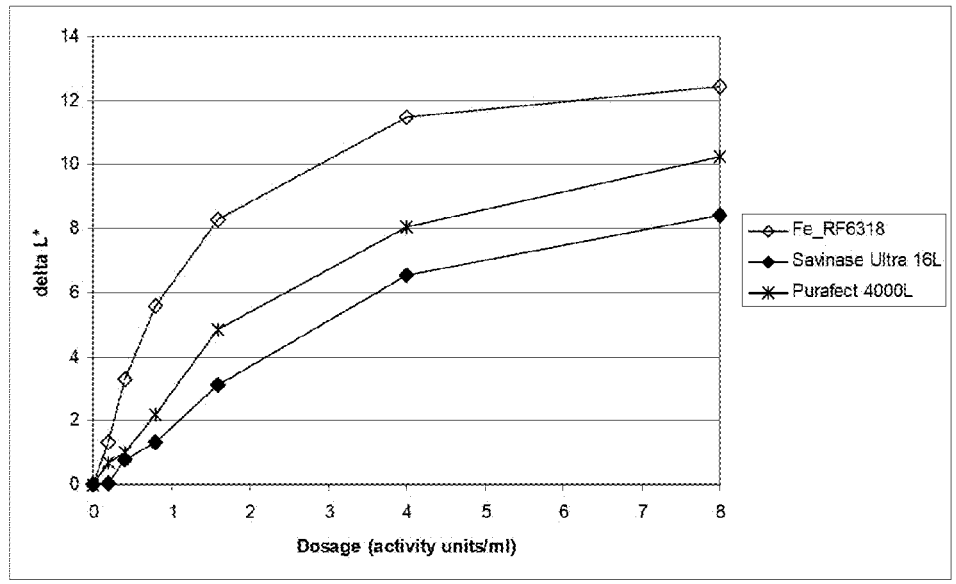
Figure 12A:
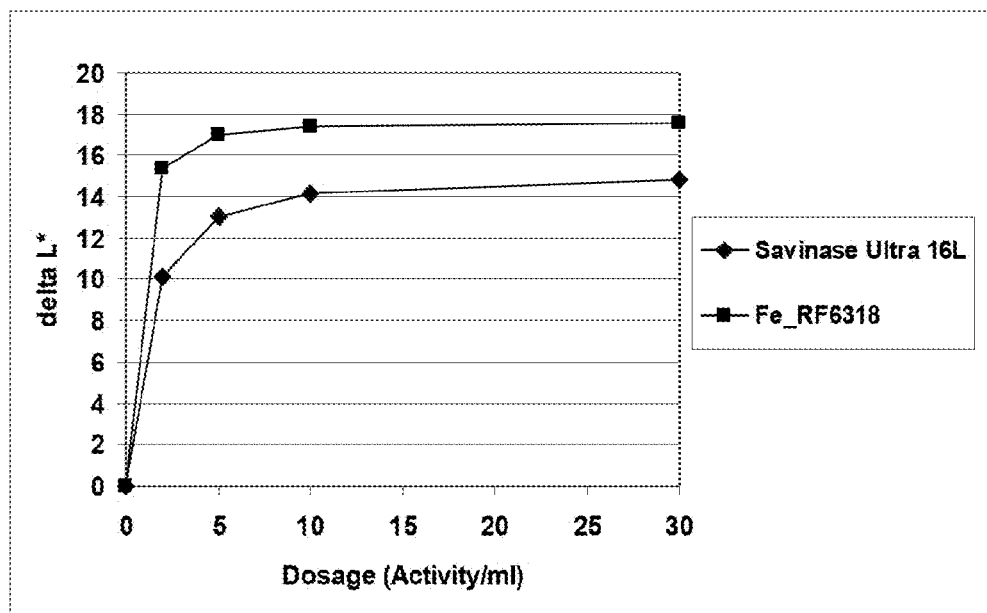
FIGS. 12A-C show the performance of recombinant protein Fe_RF6318 on different stains in Launder Ometer tests with liquid detergent Ariel Sensitive (without enzymes) at 30° C. Commercial preparation Savinase Ultra 16L was used for comparison. ΔL* (deltaL*)=lightness value L* of enzyme treated fabric–lightness value L* of fabric treated with buffer only (enzyme blank).
Figure 12B:
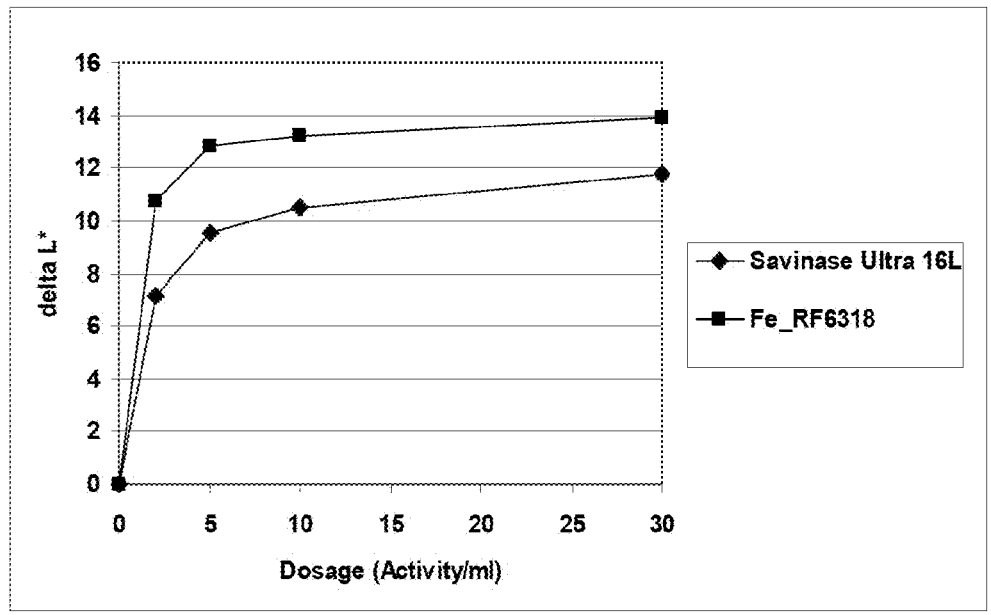
Figure 12C:
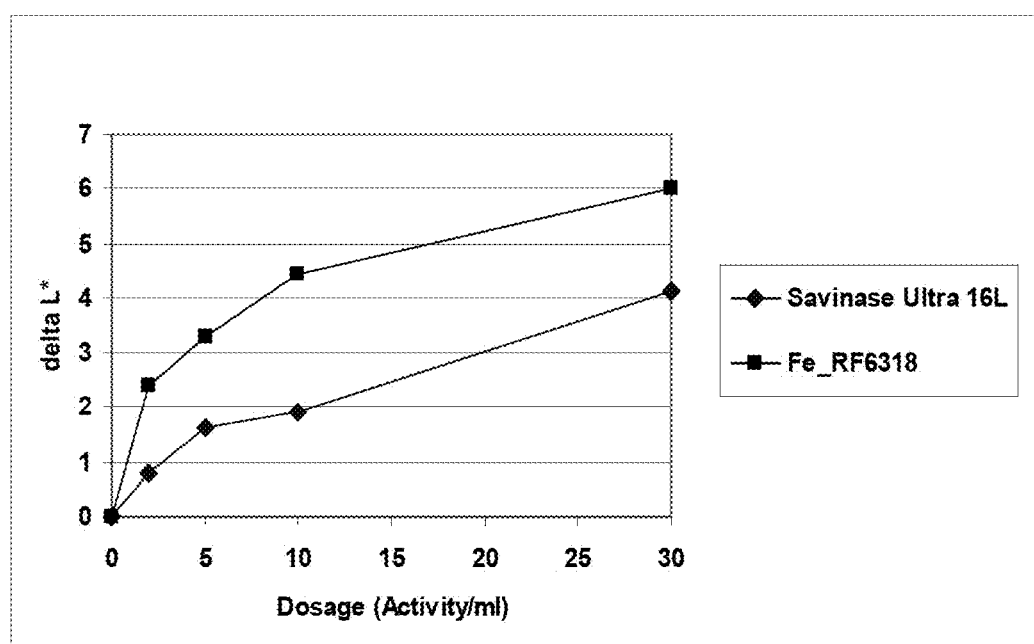
Figure 13A:
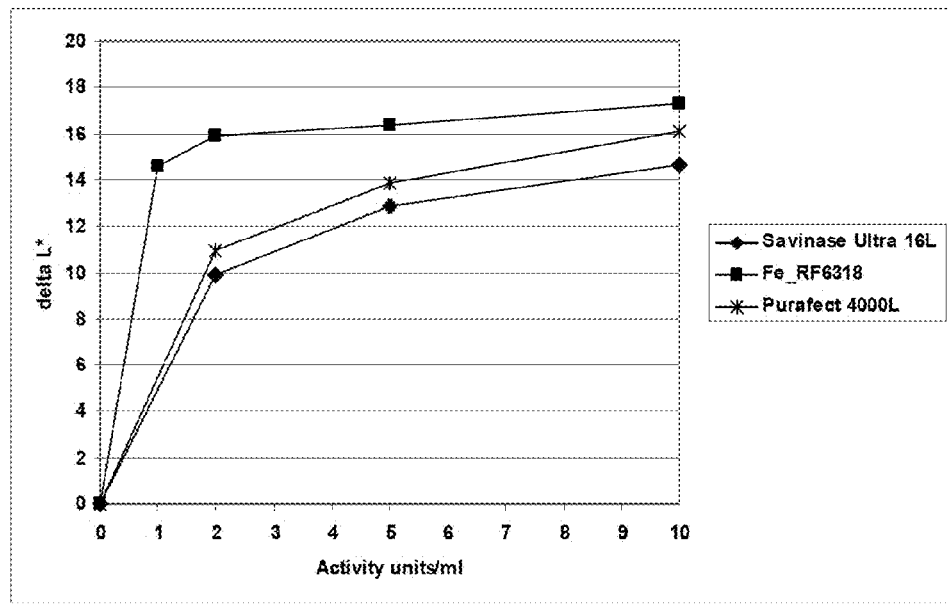
FIGS. 13A-D show the performance of recombinant protein Fe_RF6318 on different stains in Launder Ometer tests with liquid Base detergent for coloured fabrics at 30° C. Commercial preparations Savinase® Ultra 16L and Purafect® 4000 L were used for comparison. ΔL* (deltaL*)=lightness value L* of enzyme treated fabric–lightness value L* of fabric treated with buffer only (enzyme blank).
Figure 13B:
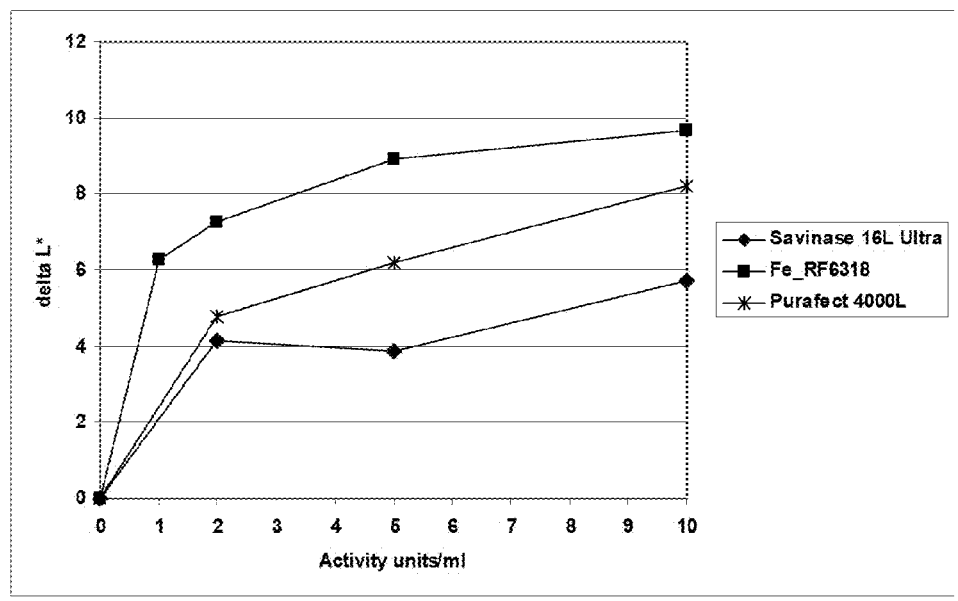
Figure 13C:
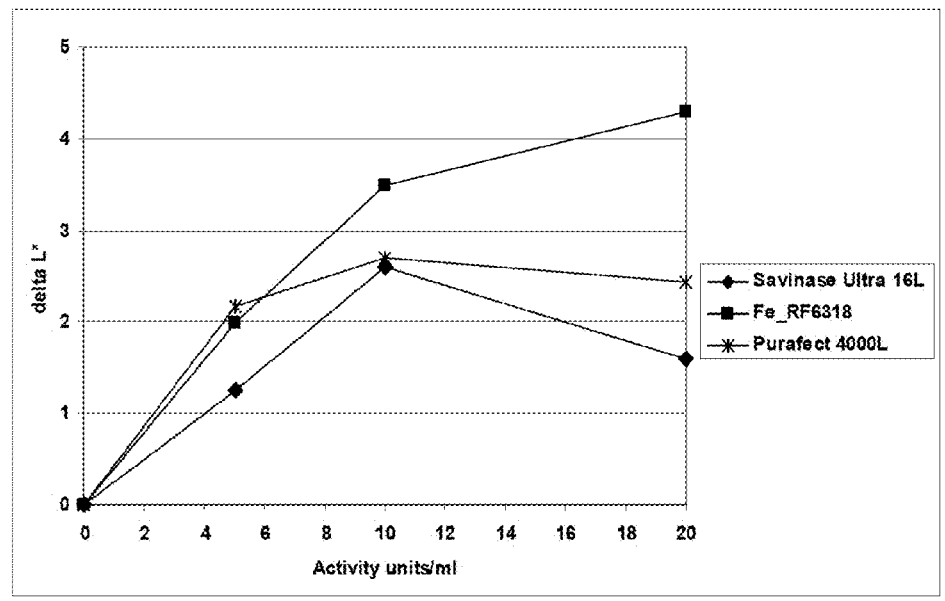
Figure 13D:
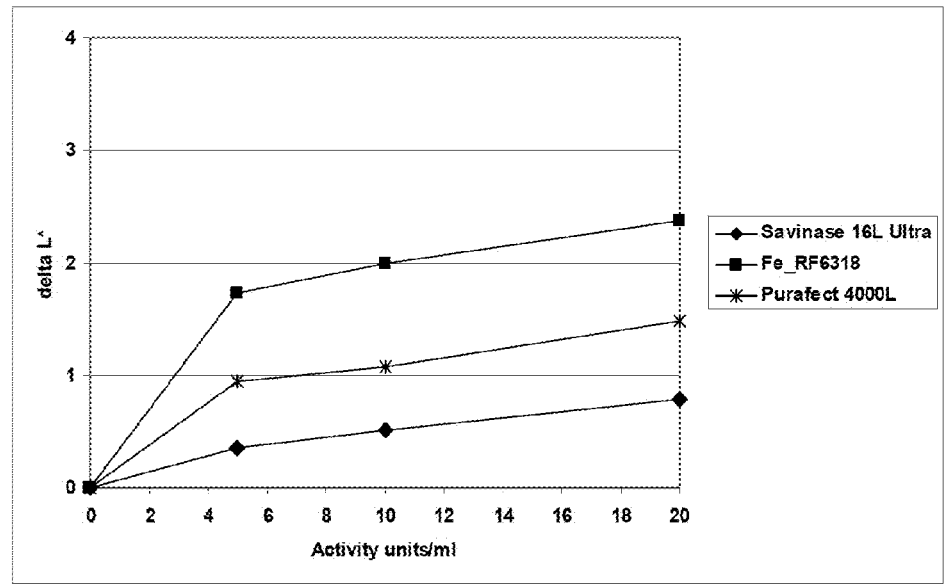
Figure 17A:
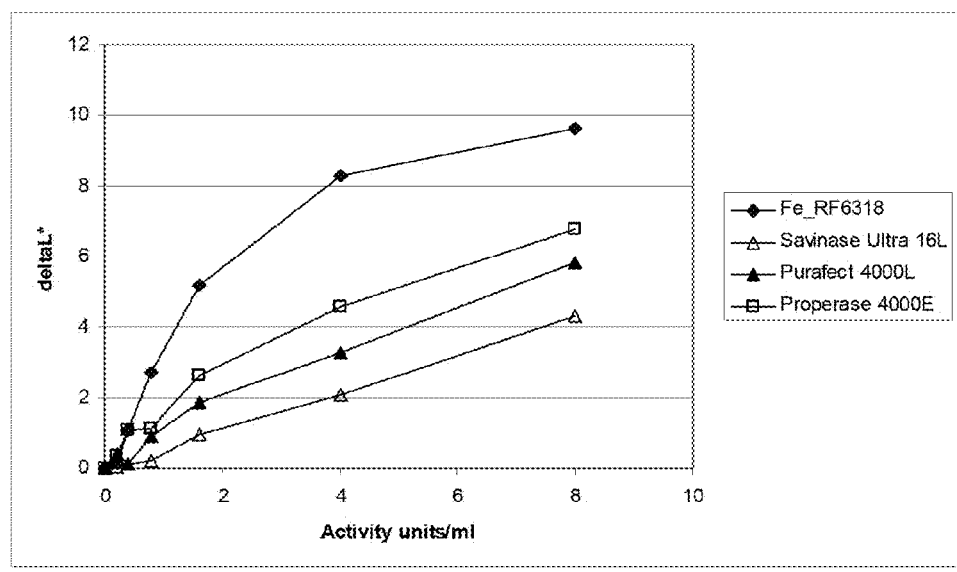
FIGS. 17A and 17B show the performance of recombinant Fe_RF6318 protein with blood/milk/ink stain (Art 117, EMPA) and Liquid Base concentration of 3.3 g/l at 10° C. and 20° C. Commercial preparations Savinase® Ultra 16L, Purafect® 4000L and Properase® 4000 E were used for comparison. ΔL* (deltaL*)=lightness value L* of enzyme treated fabric–lightness value L* of fabric treated with buffer only (enzyme blank).
Figure 17B:
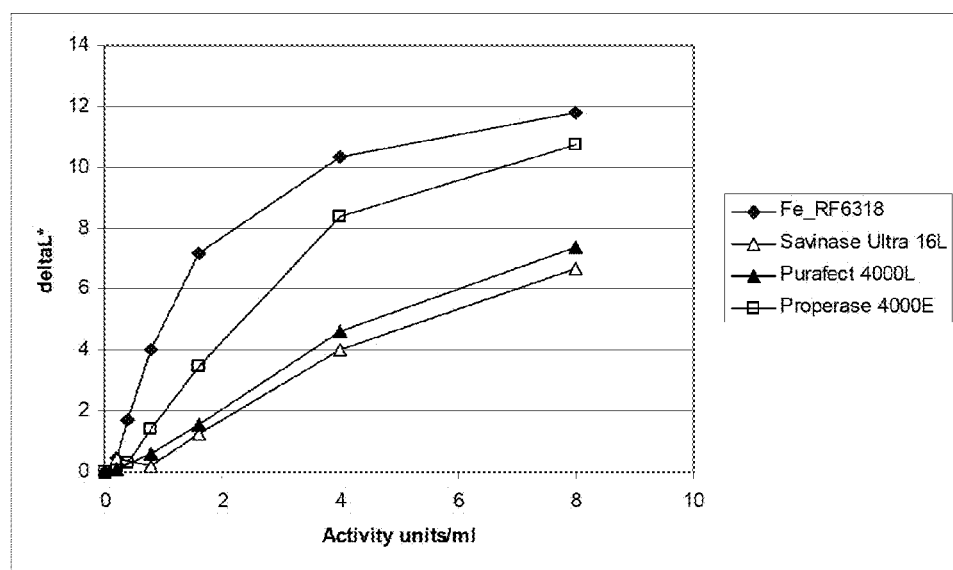

The Fe_RF6318 protease removed blood/milk/ink standard stain also in liquid base detergent and in Ariel Sensitive (Procter & Gamble, UK) in the presence of the liquid base detergent and at 30° C. (Example 9). The efficiency on blood/milk/ink stain was considerably higher than with the commercial preparations Savinase® Ultra 14L and Purafect® 4000L (FIGS. 10 and 11). The enzyme preparations were dosed as activity units. The same effect was observed also when the dosing was calculated as amount of added protein (FIGS. 10B and 11B). Washings performed with liquid detergent concentration of 3.3. g/l and at 10° C. and 20° C. again showed superior performance over commercial preparations Savinase® Ultra 14L, Purafect® 4000L and Properase® 4000E (Example 13; FIG. 17).

In addition to the blood/milk/ink stains the Fe_RF6318 protease was effective in removing stains, such as grass and cocoa when tested in liquid detergents at 30° C. Treatments were performed in ATLAS LP-2 Launder-Ometer. Results (FIGS. 12 and 13) show that the Fe_RF6318 was effective on several stains at low temperatures like 30° C.

Figure 14A:
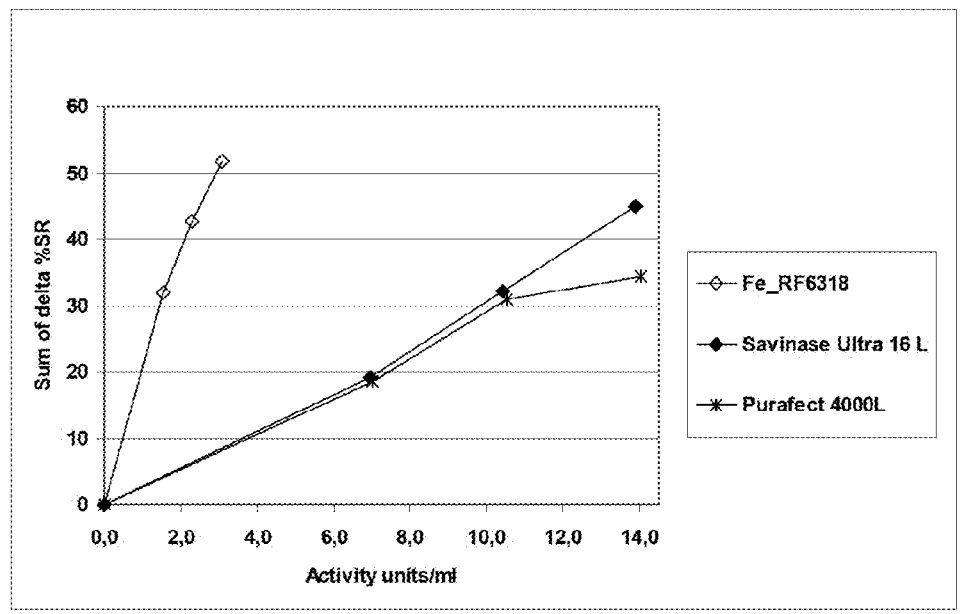
FIGS. 14A and 14B describe total stain removal efficiency (delta % SR) of Fe_RF6318 enzyme preparation on eight different protease sensitive stains (Table 5) in full-scale washing trials. Commercial preparations Savinase® Ultra 16L and Purafect® 4000L were used for comparison.
Figure 14B:
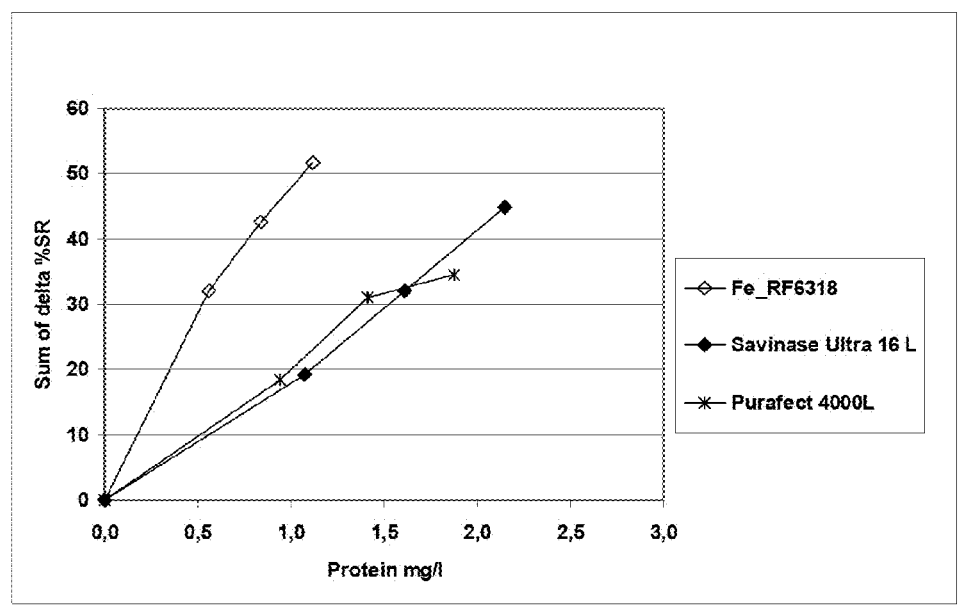
Figure 15A:
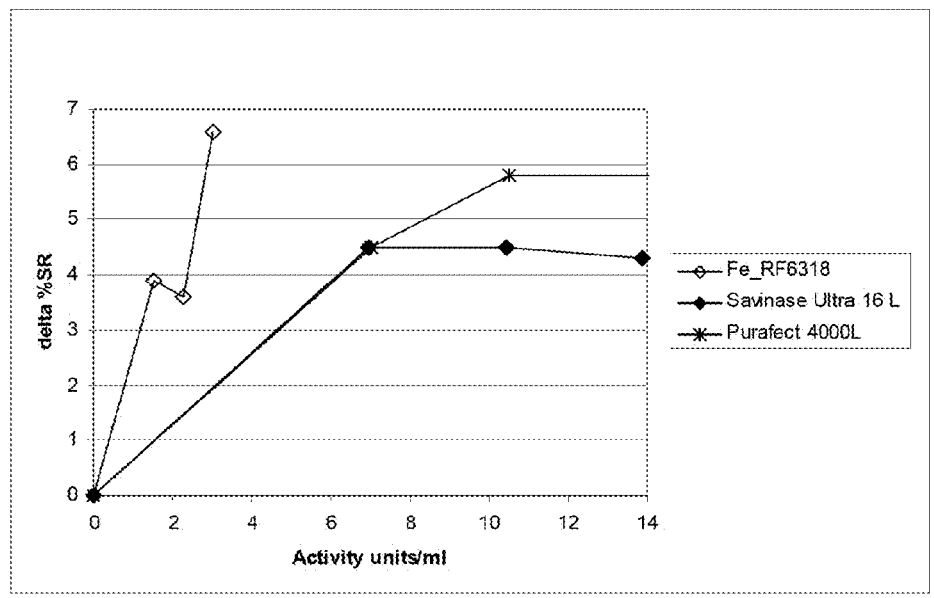
FIGS. 15A-E describe the stain removal effect with liquid detergent base for coloured fabrics in full scale trial at 30° C.
Figure 15B:
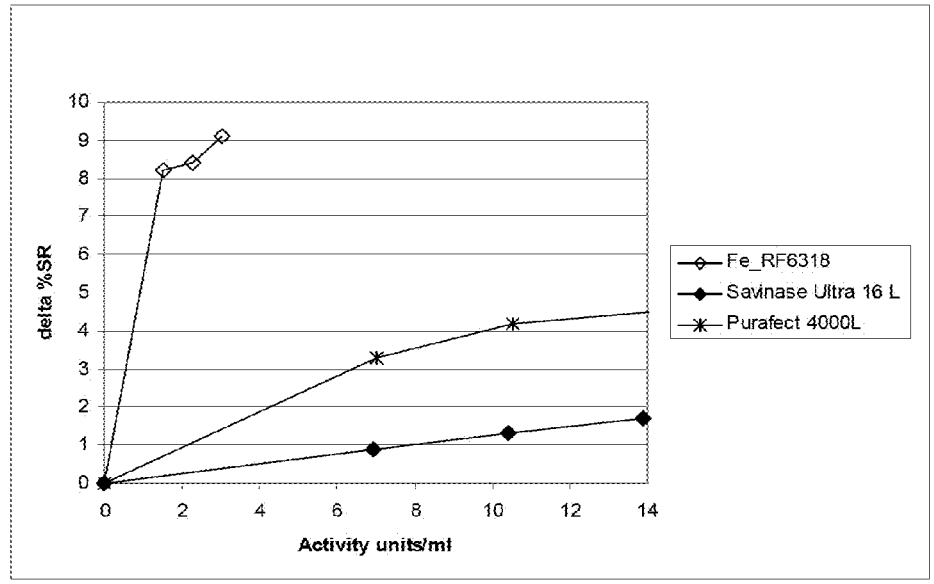
Figure 15C:
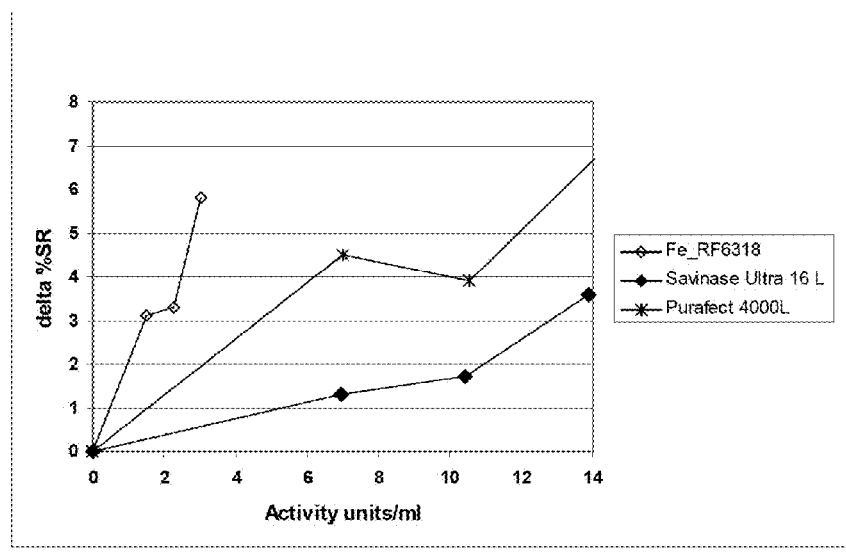
Figure 15D:
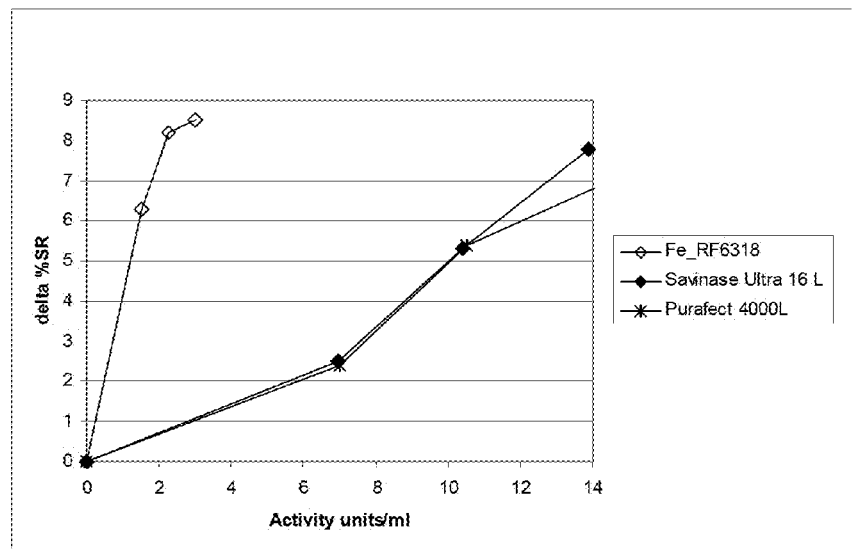
Figure 15E:
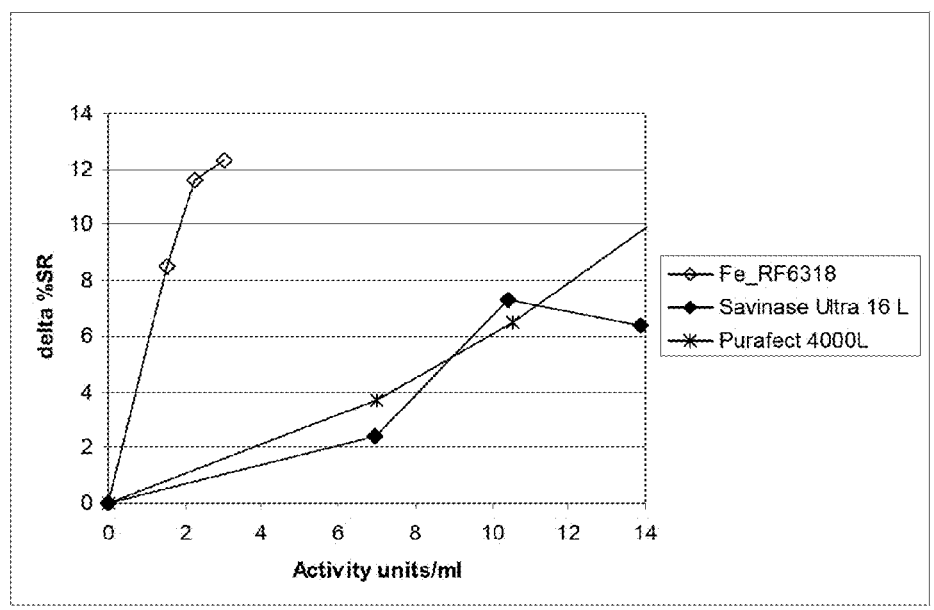
Figure 16A:
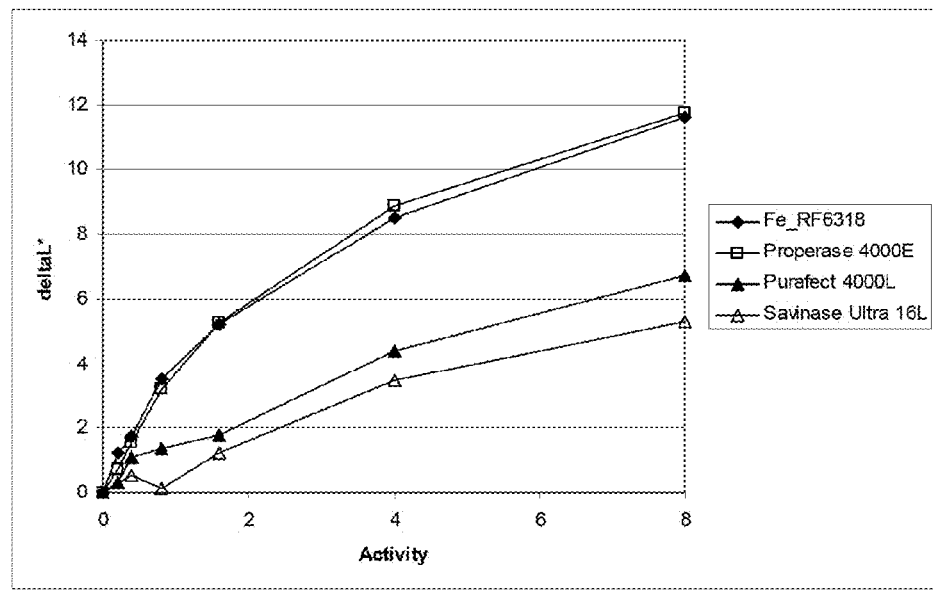
FIGS. 16A-F describe the performance of recombinant Fe_RF6318 protein with blood/milk/ink stain (Art 117, EMPA) at temperatures from 10° C. to 60° C., pH 9, 60 min. Commercial preparations Savinase Ultra® 16L (Novozymes A/S, DK), Purafect® 4000L (Genencor Inc., USA) and Properase® 4000E (Genencor Inc., USA) were used for comparison. ΔL* (deltaL*)=lightness value L* of enzyme treated fabric–lightness value L* of fabric treated with buffer only (enzyme blank).
Figure 16B:
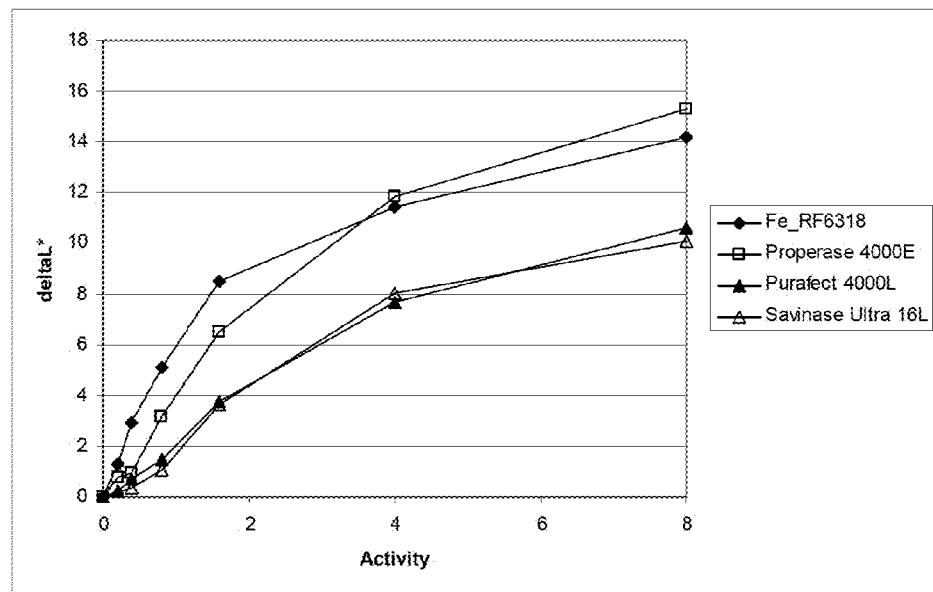
Figure 16C:
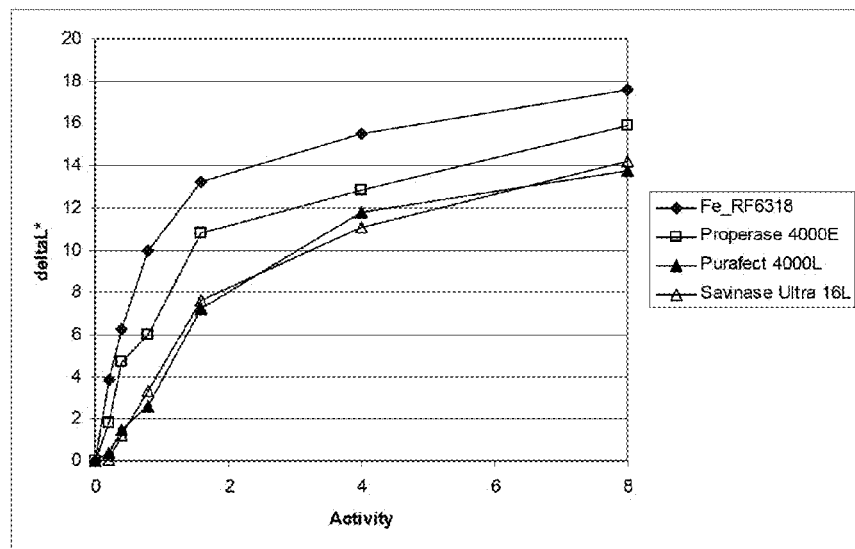
Figure 16D:
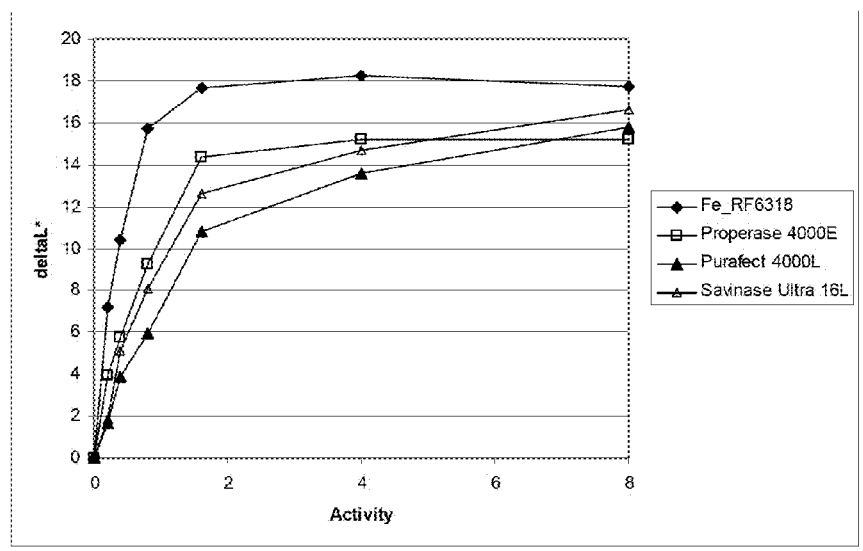
Figure 16E:
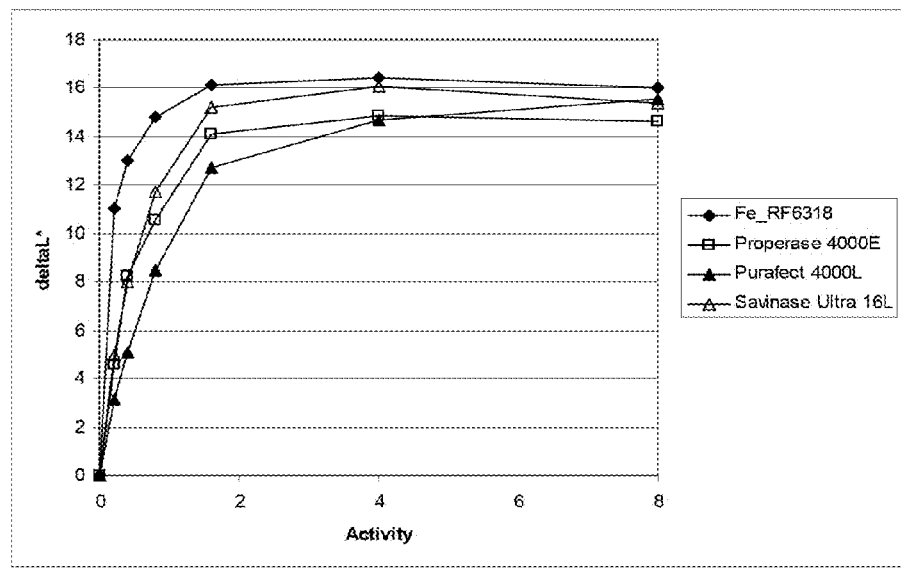
Figure 16F:
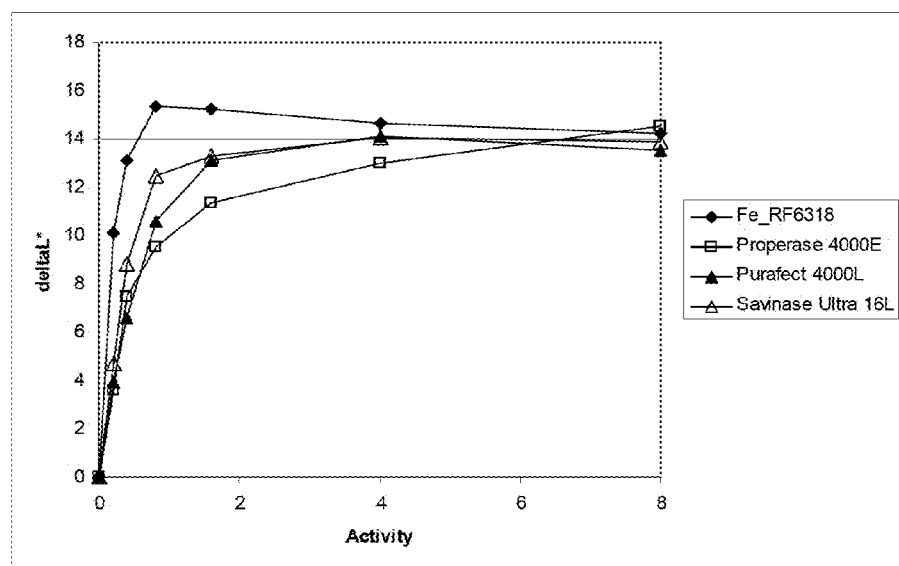

The performance of recombinant Fe_RF6318 enzyme preparation produced in *T. reesei* was tested in the presence of liquid base detergent in full scale in a washing machine at 30° C. (Example 11). Eight different protease sensitive tracers for testing side effects are presented in Table 5 and the process conditions in Table 6. Enzyme dosages used in the test trials were calculated both as enzyme activities and as amount of enzyme protein. Results presented in FIGS. 14A-B show that the sum of the results obtained with the different stains was higher with the Fe_RF6318 was higher than with the commercial protease preparations Savinase® Ultra 16L and Purafect® 4000L when the enzyme was dosed as amount of activity or as protein. The Fe_RF6318 was most efficient on blood/milk/ink, chocolate/milk, groundnut oil/milk and egg yolk stains (FIGS. 15A-E).

According to a preferred embodiment of the invention the fungal serine protease of the invention is useful in detergent liquids and detergent powders as shown in Examples 6 to 13. The enzyme of enzyme preparation of the invention may be formulated for use in a hand or machine laundry or may be formulated for use in household hard surface cleaning or preferably in hand or machine dishwashing operations.

Example 1

Production and Purification of the *Fusarium equiseti* RF6318 Protease (a) Cultivation of *Fusarium equiseti* RF6318

Fungal strain RF6318 was previously isolated as a filamentous fungus producing cellulases. It was identified as *Fusarium* cf. equiseti (Libert) Desmazières (by Arthur de Cock, Identification Services, Centralbureau Voor Schimmelcultures, P.O. Box 85167, 3508 AD Utrecht, The Netherlands). *F. equiseti* RF6318 was shown to produce protease activity on agar plate assay containing haemoglobin as a substrate. As the plate cultivations were performed at about 10° C. this result suggested that RF6318 produces a protease or proteases acting at cold temperatures. The *F. equiseti* RF6318 was grown, maintained and sporulated on Potato Dextrose (PD) agar (Difco) at +4° C. For enzyme production spores from RF6318 slant were inoculated into a culture medium which contained: 30 g/l Corn meal (finely ground), 5 g/l Corn steep powder, 4 g/l Soybean meal (de-fatted), 2 g/l $KH_2PO_4$, 1 g/l NaCl and 1 g/l Paraffin oil. The pH of the medium was adjusted before sterilization with NaOH to 8.5 and the medium was autoclaved for 30 minutes at 121° C. The microbe was cultivated in 50 ml volume on a shaker (200 rpm) at 28° C. for 7 days. The spent culture supernatant was shown to contain alkaline protease activity, when activity measurements were performed (according to Example 1c) at different pH values (pH 7-10). Because of this alkaline activity, the RF6318 strain was chosen as putative protease gene donor strain.

(b) Purification of Protease from the *F. equiseti* RF6318 Culture Medium

Cells and solids were removed from the spent culture medium by centrifugation for 30 min, 50000 g at +4° C. (Sorvall RC6 plus). 50 ml of the supernatant was used for purification of the protease. After centrifugation, pH of supernatant was adjusted to 8.0 with addition of HCl. The supernatant was then filtered through 0.44 μm filter (MILLEX HV Millipore) and applied to a 5 mL Q Sepharose FF column (GE Healthcare) equilibrated in 20 mM Tris-HCl, pH 8. Flow through fraction was collected and its pH was lowered to 7.5 by adding HCl. Solid ammonium sulfate was added to the flow through fraction to obtain a final salt concentration of 1 M. The flow through fraction was then filtered through 0.44 μm filter before applying to phenyl Sepharose HP (1 mL) column (GE Healthcare) equilibrated in 20 mM Tris-HCl-1 M ammonium sulfate pH 7.5. The proteins were eluted with a linear decreasing ammonium sulfate gradient (from 1 to 0 M). Fractions of 1 ml were collected and analyzed for protease activity on resorufin-labeled casein (Boehringer Mannheim Biochemica) at pH 8.0 as instructed by the manufacturer. Fractions with protease activity were pooled and ultra filtrated with 10 k membrane (Amicon). The concentrated filtrate was applied to a Superdex 75 10/300 GL column (GE Healthcare) equilibrated with 20 mM Tris-HCl-200 mM NaCl, pH 7.5. Proteins were eluted with the same buffer and 0.5 ml fractions were collected. The protease activity from these fractions was analyzed. The fractions with protease activity were analyzed on sodium dodecyl sulfate polyacrylamide gel electrophoresis (SDS-PAGE). The fractions were shown to contain one major protein band having a molecular mass of about 29 kDa. The chosen fractions were pooled. The pooled fractions were used for preparation of peptides (Example 2). According to activity assay measurements, the purified protein had its pH optimum at pH 10. This purified *F. equiseti* RF6318 protease is named as FeRF6318.

(c) Protease Activity Assay

Protease activity was assayed by the casein Folin-Ciocalteau method using casein as a substrate. Rate of casein degradation by a protease was measured by spectrophotometrical monitoring of the release of acid-soluble fragments as a function of time. Casein substrate used in the assay was prepared as follows: 6 g of Casein Hammerstein Grade MP Biomedicals, LLC (101289) was dissolved in 500 ml of 30 mM Tris, 2.0 mM $CaCl_2$, 0.7 mM $MgCl_2$, 2.5 mM $NaHCO_3$. The pH of the substrate solution was adjusted to 8.5. The enzyme reactions were stopped using 0.11 M TCA solution. The Folin reagent used in the assay was prepared by diluting 25 ml of 2 N Folin-Ciocalteu's phenol reagent (SIGMA, F 9252) to 100 ml by distilled water. The reaction was started by first incubating 2.5 ml of substrate solution for 5 min at 50° C. after which 0.5 ml of enzyme solution was added and reaction was conducted for 30 min. After 30 min reaction 2.5 ml of reaction stop solution was added, the contents were mixed and allowed to stand for 30 minutes at room temperature. Tubes were centrifuged 4000 rpm for 10 minutes (Hettich Rotanta 460). One ml of clear supernatant was mixed with 2.5 ml 0.5 M $Na_2CO_3$ and 0.5 ml diluted Folin reagent. After waiting for at least 5 min (color development) the absorbance of the mixture (colour) was measured at 660 nm against an enzyme blank. The enzyme blank was prepared as follows: 0.5 ml enzyme solution was mixed with 2.5 ml stopping solution and 2.5 ml substrate, and the mixture was incubated for 30 min at 50° C. One unit of enzyme activity was defined as the enzyme quantity that liberates the acid soluble protein hydrolysis product corresponding to 1 μg of tyrosine per ml (or g) of the reaction mixture per min.

Example 2

N-Terminal and Internal Amino Acid Sequencing of the Purified *F. equiseti* Protease Fe_RF6318

For determination of internal sequences, the Coomassie Brilliant Blue stained band was cut out of the polyacrylamide gel and "in-gel" digested essentially as described by Shevchenko et al. (1996). Proteins were reduced with dithiothreitol and alkylated with iodoacetamide before digestion with trypsin (Sequencing Grade Modified Trypsin, V5111, Promega).

Electrospray ionization quadrupole time-of-flight tandem mass spectra for de novo sequencing were generated using a Q-TOF instrument (Micromass, Manchester, UK) connected to an Ultimate nano liquid chromatograph (LC-Packings, The Netherlands) essentially as described previously (Poutanen et al., 2001) but using a 150 μm×1.0 mm trapping column (3 μm, 120 Å, #222403, SGE Ltd UK) for peptide preconcentration.

For N-terminal sequence analysis SDS-PAGE/separated proteins were transferred by electroblotting into a polyvinylidine difluororide membrane (ProBlott; Perkin Elmer Applied Biosystems Division, Foster City, Calif.). After being stained with Coomassie brilliant blue, the protein bands of interest were removed and subjected to N-terminal sequence analysis by Edman degradation on a Procise 494A protein sequencer (Perkin Elmer Applied Biosystems Division, Foster City, Calif.)

The N-terminal and internal peptide sequences determined from the purified Fe_RF6318 protease are shown in Table 1. The peptide sequences showed homology to published protease sequences from *Fusarium oxysporum* serine proteases with EMBL Accession numbers Q5R2N9 and O74236.

TABLE 1

N-terminal and internal peptide sequences determined
from Fe_RF6318 protease

| Peptide | Sequence | SEQ ID | Comments |
|---|---|---|---|
| #3792 | ALTTQSNAPWGLAAISRXTP | NO: 1 | N-terminal sequence X may be C, S, T or R |
| 1246.673 | TVAAADSSWR | NO: 2 | |
| 3341.633 | XTYGVAK | NO: 3 | |
| 1503.799 | EA(L/I)TVGATTSADAK | NO: 4 | Third amino acid is not conclusive, can be L or I |

Example 3

Cloning of the *F. equiseti* RF6318 Gene Encoding Fe_RF6318 Protease (a) Isolation of DNA and Molecular Biology Methods Used Standard molecular biology methods were used in the isolation and enzyme treatments of DNA (e.g. isolation of plasmid DNA, digestion of DNA to produce DNA fragments), in *E. coli* transformations, sequencing etc. The basic methods used were either as described by the enzyme, reagent or kit manufacturer or as described in the standard molecular biology handbooks, e.g. Sambrook and Russell (2001). Isolation of genomic DNA from *F. equiseti* RF6318 was done as described in detail by Raeder and Broda (1985).

(b) Primers for Probe Preparation

The probe for cloning the gene encoding the Fe_RF6318 protein was synthesised by PCR. Degenerate oligos were planned basing on the amino acid sequences of the peptides obtained from the purified Fe_RF6318 (Table 1). The sequences of the primers are shown in Table 2 (SEQ ID NOs: 5-8).

extension at 72° C. and a final extension at 72° C. for 5 min. Primer combination PRO88 (SEQ ID NO:6) and PRO89 (SEQ ID NO:7) produced a specific DNA product having the expected size (according to calculations basing on published fungal protease sequences). The DNA product was isolated and purified from the PCR reaction mixture and cloned to pCR®2.1-TOPO® vector according to the manufacturers instructions (Invitrogen, USA). The 866 bp DNA fragment was sequenced from this plasmid (SEQ ID NO:9). The pCR®2.1-TOPO® plasmid containing this PCR amplified DNA fragment was named pALK2521. The *E. coli* strain RF7664 including the plasmid pALK2521 was deposited to the DSM collection under the accession number DSM 22171.

The deduced amino acid sequence of the PCR fragment included the sequences of the internal Fe_RF6318 peptides 1246.673 (SEQ ID NO:2) and 3341.633 (SEQ ID NO:3) (Table 1). Also the C-terminal part of the N-terminal peptide #3792 (SEQ ID NO:1) not included in the primer was found from the deduced amino acid sequence (Table 1). This confirms that the DNA fragment obtained from the PCR reaction

TABLE 2

Oligonucleotides (SEQ ID NOs: 5-8) used as PCR primers in probe amplification. Oligos, SEQ ID NOs, oligo lengths and degeneracies, oligonucleotides and the amino acids of the peptide used in planning of the oligonucleotide sequence.

| Oligo | SEQ ID NO: | Length (nts) | Degeneracy | Sequence[a] | Peptide[b] |
|---|---|---|---|---|---|
| PRO87 | 5 | 20 | 256 | CARTCNAAYGCNCCNTGGGG (s) | #3792 |
| PRO88 | 6 | 20 | 128 | CARAGYAAYGCNCCNTGGGG (s) | #3792 |
| PRO89 | 7 | 20 | 2048 | GCRTCNGCNGANGTNGTNGC (as) | 1503.799 |
| PRO90 | 8 | 20 | 1024 | GCRTCNGCRCTNGTNGTNGC (as) | 1503.799 |

[a]N = A, T, C or G; R = A or G, Y = T or C; "s" in the parenthesis = sense strand, "as" in the parenthesis = antisense strand.
[b]The peptide sequences are included in Table 1.

(c) PCR Reactions and Selection of Probes for Cloning

*F. equiseti* RF6318 genomic DNA was used as a template for probe synthesis. The PCR reaction mixtures contained 10 mM Tris-HCl, pH 8.8, 50 mM KCl, 0.1% Triton X-100, 1.5 mM MgCl$_2$, 0.2 mM dNTPs, 1 μM each primer and 4 units of Dynazyme II DNA polymerase (Finnzymes, Finland) and approximately 3 μg of genomic DNA per 100 μl reaction volume. The conditions for the PCR reactions were the following: 5 min initial denaturation at 96° C., followed by 32 cycles of 1 min at 96° C., 30 sek annealing at 55.5° C., 1 min was part of the gene encoding the Fe_RF6318 protein and was thus used as a probe for screening the full length gene from *F. equiseti* genomic DNA.

(d) Cloning of the *F. Equiseti* RF6318 Gene Encoding Fe_RF6318 Protease

*F. equiseti* genomic DNA was digested with several restriction enzymes for Southern blot analysis. The hybridization was performed with the 884 kb EcoRI fragment including SEQ ID NO:9, cut from the plasmid pALK2521 as a probe (Example 3c). The above probe was labeled by using digoxigenin according to supplier's instructions (Roche, Germany).

Hybridisation was performed over night at 65° C. After hybridization the filters were washed 2×5 min at RT using 2×SSC-0.1% SDS followed by 2×15 min at 65° C. using 0.1×SSC-0.1% SDS.

Several hybridizing fragments in the *F. equiseti* genomic DNA digests could be detected. Genomic MunI and BglII digests contained hybridizing fragment with approximate sizes of 4.2 kb and 3.2 kb, respectively. The single hybridizing fragment sizes were large enough to contain the full length gene encoding the Fe_RF6318 protein according to calculations basing on published fungal protease sequences. Genomic DNA fragments were isolated from the RF6318 genomic MunI and BglII digests from the size range of the hybridizing fragment (approximately 4 kb for MunI digestion and approximately 3 kb for the BglII digestion). The genomic fragments were isolated from agarose gel and were cloned to pBluescript II KS+(Stratagene, USA) vectors cleaved with EcoRI and BamHI. Ligation mixtures were transformed to *Escherichia coli* XL10-Gold cells (Stratagene) and plated on LB (Luria-Bertani) plates containing 50-100 μg/ml ampicillin. The *E. coli* colonies were screened for positive clones using colonial hybridization with the pALK2521 insert as a probe. Hybridisation was performed as described for the RF6318 genomic DNA digests. Four positive BglII and eight positive MunI clones were collected from the plates. They were shown by restriction digestion to contain inserts of expected sizes. The insert from the MunI fragment ligated to the BamHI vector was cut with PstI-SalI double digestion. The insert from the BglII fragment ligated to the EcoRI vector was cut with PstI-NotI double digestion. A Southern blot was performed on inserts of the collected clones (Southern blot hybridization at 68° C. and washed 2×5 min at RT using 2×SSC-0.1% SDS followed by 2×15 min at 68° C. using 0.1×SSC-0.1% SDS). Three of the collected BglII clones and six of the collected MunI clones contained the hybridizing fragment in Southern blot. The full-length gene encoding the Fe_RF6318 protease (SEQ ID NO:10) was sequenced from the 3.2 kb BglII insert and the plasmid containing this insert was named pALK2529. The *E. coli* strain RF7800 including the plasmid pALK2529 was deposited to the DSM collection under the accession number DSM 22172. The gene encoding the Fe_RF6318 protein was named as Fe prtS8A.

(e) Characterisation of the Gene Encoding Fe_RF6318 Protease and the Deduced Amino Acid Sequence The Fe prtS8A sequence (SEQ ID NO:10) and the deduced amino acid sequence (SEQ ID NO:11) are shown in FIG. 1A-B. The length of the gene is 1303 bp (including the stop codon). One putative intron was found having the length of 64 bps (5' and 3' border sequences according to those of fungal introns, according to Gurr et al. (1987). The deduced protein sequence (SEQ ID NO:11) consists of 412 amino acids including a predicted signal sequence of 20 amino acids (SignalP V3.0; Nielsen et al., 1997 and Nielsen and Krogh, 1998). The whole N-terminal peptide #3792 (also the N-terminal part not included in the probe sequence) was included in the deduced amino acid sequence. The predicted molecular mass was 29141.09 Da for the mature polypeptide and the predicted pI was 9.30. These predictions were made using the Compute pI/MW tool at ExPASy server (Gasteiger et al., 2003). The deduced amino acid sequence contained two possible N-glycosylation sites at amino acid positions Asn77 and Asn255 (FIG. 1), but according to CBS Server NetNGlyc V1.0 only the site at position Asn77 (located in the pro sequence) is probable.

(f) Homology, Identity and Alignment Studies

The homologies to the published protease sequences were searched using the BLASTX program version 2.2.9 at NCBI (National Center for Biotechnology Information) with default settings (Altschul et al., 1990). The highest homologies were to a hypothetical protein from *Gibberella zeae* (*Fusarium graminearum*) (EMBL accession number XP_383491) and *Trichoderma harzianum* (*Hypocrea lixii*) serine endopeptidase (EMBL Accession number CAL25580). Also homology was found to a sequence included in the patent application U.S. 60/818,910 (Catalyst Bioscience Inc.) as SEQ ID NO:313. The Fe_RF6318 sequence was aligned with the above homologous sequences. The identity values obtained by using ClustalW alignment (ebi.ac.uk/Tools/clustalw; Matrix: BLOSUM, Gap open: 10, Gap extension: 0.5) are shown in Table 3.

TABLE 3

The identity values (%) obtained from ClustalW alignment of the deduced protease amino acid sequences. The mature amino acid sequences excluding the signal peptides and propeptides were aligned. Matrix: BLOSUM, Gap open: 10, Gap extension: 0.5, EMBL_EBI. *G. zeae*, XP_383491; *T. harzianum* CAL25508; U.S. Pat. No. 60/818,910, SEQ ID NO: 313 in the application.

|  | Fe_RF6318 | G. zeae | T. harz. | U.S. Pat. No. 60/818,910 |
|---|---|---|---|---|
| Fe_RF6318 | 100 | 85 | 75 | 74 |
| G. zeae |  | 100 | 78 | 76 |
| T. harz. |  |  | 100 | 94 |
| U.S. Pat. No. 60/818,910 |  |  |  | 100 |

Example 4

Production of the Recombinant Fe_RF6318 Protease in *Trichoderma reesei*

(a) Preparing the Production (Host) Vector

The expression plasmid pALK2533 was constructed for production of recombinant Fe_RF6318 protease in *Trichoderma reesei*. The Fe prtS8A gene with its own signal sequence was exactly fused to the *T. reesei* cbh1 (cel7A) promoter by PCR. The Fe prtS8A gene fragment was excised from its 3'-end by BamHI (a site created after stop codon in PCR). This leaves no original Fe prtS8A terminator in the construct prior to the cbh1 terminator sequence. An amdS marker gene was added to the construction including the cbh1 promoter and cbh1 terminator. The construction is analogous to that described in Paloheimo et al. (2003) and the 8.7 kb linear expression cassette is presented in FIG. 2. The expression cassette was isolated from the vector backbone after EcoRI digestion and was used for transforming *T. reesei* protoplasts. The host strain used does not produce any of the four major *T. reesei* cellulases (CBHI, CBHII, EGI, EGII). The transformations were performed as in Pennilä et al. (1987) with the modifications described in Karhunen et al. (1993). The transformants were purified on selection plates through single conidia prior to sporulating them on PD.

(b) Protease Production in Shake Flasks and Laboratory Scale Bioreactor

The transformants were inoculated from the PD slants to shake flasks containing 50 ml of complex lactose-based cellulase inducing medium (Joutsjoki et al., 1993) buffered with 5% KH$_2$PO$_4$ at pH 6.0. The protease production of the transformants was analyzed from the culture supernatants after growing them for 7 days at 30° C., 250 rpm. In SDS-PAGE gels, a major protein band of about 29 kDa corresponding to recombinant Fe_RF6318 protease was detected from the spent culture supernatants. The protease activity was assayed using casein as a substrate as described in Example 1c. Clearly increased activities compared to host were measured from the culture supernatants The integration of the expression cassette into the fungal genomes was confirmed from chosen transformants by using Southern blot analysis in which several genomic digests were included and the expression cassette was used as a probe.

The *T. reesei* transformants producing the best protease activities in the shake flask cultivations were chosen to be cultivation in laboratory scale bioreactors. Cellulase inducing complex medium was used in the cultivations. The spent culture medium obtained from the cultivations was used in application tests (Examples 6-11) and as starting material for purification and further characterization of the recombinant Fe_RF6318 protease.

Example 5

Purification and Characterization of the Recombinant Fe_RF6318 Protease

Figure 3:
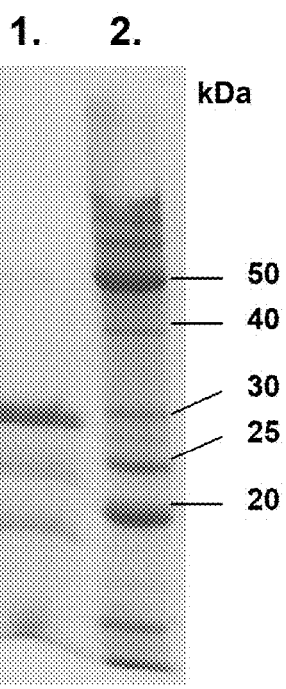
FIG. 3 shows the partially purified recombinant Fe_RF6318 protein analysed on 12% SDS PAGE gel. Lane 1. Sample of the partially purified Fe_RF6318, Lane 2. MW marker (Bench Mark Protein Ladder, Invitrogen).

Cells and solids were removed from the spent culture medium obtained from the fermentation (Example 4) by centrifugation for 30 min, 50000 g at +4° C. (Sorvall RC6 plus). 15 ml of the supernatant was used for purification of protease. All purification steps were performed at cold room. After centrifugation, sample was filtered through 0.44 µm filter (MILLEX HV Millipore) before applying to HiPrep 26/10 Desalting column (from GE Healthcare) equilibrated in 20 mM Tris pH 8.8. Gel filtered sample was applied to a 20 mL Q Sepharose FF column (from GE Healthcare) equilibrated in 20 mM Tris pH 8.8. The flow through fraction was collected and analysed on 12% SDS PAGE gel (FIG. 3). This enzyme sample was used for characterization of pH and temperature profiles.

Temperature Profile

Figure 4A:
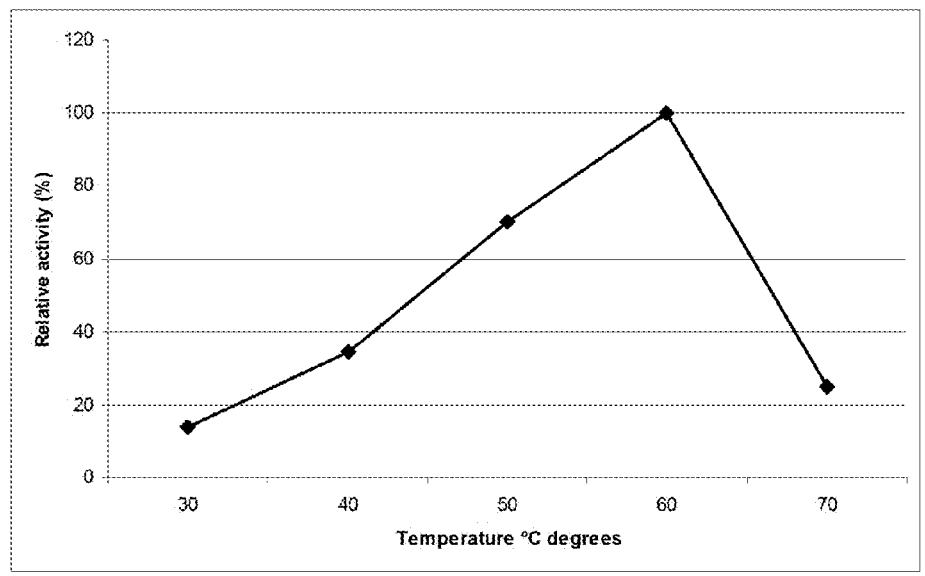
FIG. 4A describes the temperature profile of recombinant protein Fe_RF6318 assayed at pH 9 using 15 min reaction time and casein as a substrate. The data points are averages of three separate measurements.

Temperature profile was obtained for Fe_RF6318 protease by using the assay described in Example 1c, except using 15 min reaction time and pH 9.0. The result is shown in FIG. 4A. The protease has an optimal temperature around 60° C.

pH-profile

Figure 4B:
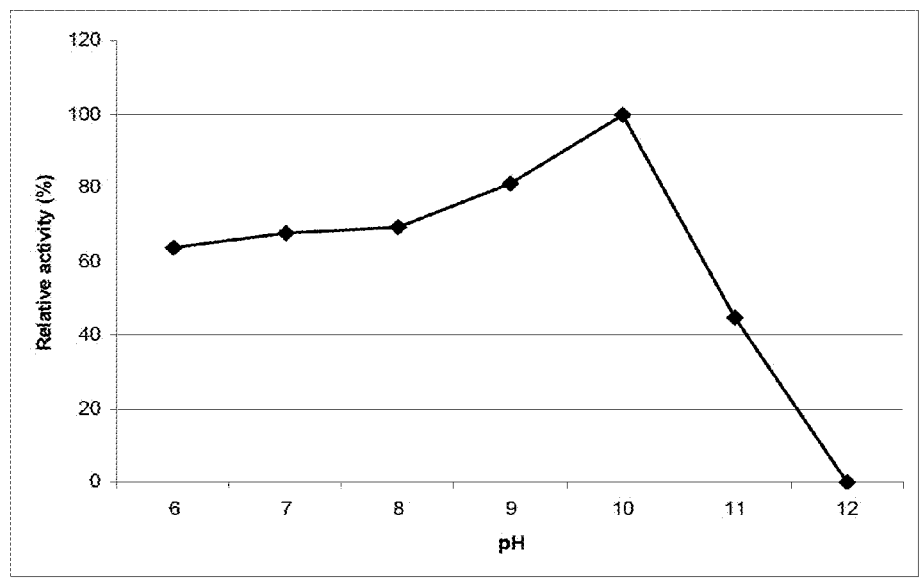
FIG. 4B describes the effect of pH on the activity of recombinant Fe_RF6318 protein. The buffer used was 40 mM Britton-Robinson buffer, casein was used as a substrate, reaction time was 15 min and reaction temperature was 50° C. The data points are averages of three separate measurements.

The pH profile of the protease was determined at 50° C. using casein as a substrate as described in Example 1c, except that casein was dissolved in 40 mM Britton-Robinson buffer, the pH of the reaction was adjusted to pH 6-12, the reaction time was 15 min and the enzyme reactions were stopped using a 0.11 M TCA solution which contained 0.22 M sodium acetate and 0.33 M acetic acid. The results are shown in FIG. 4B. The recombinant Fe_RF6318 protease exhibits relative activity over 60% from pH 6 to pH 10 with optimal activity around pH 10. The pH profile of the purified recombinant Fe_RF6318 protease corresponded to the pH profile of the wild type Fe_RF6318 protease purified as described in Example 1a.

Example 6

Performance of Recombinant Fe_RF6318 Protease at pH 9 Buffer at Different Temperatures Recombinant protein Fe_RF6318 preparation produced in *Trichoderma* (as described in Example 4), was tested for its ability to remove blood/milk/ink standard stain (Art.116, 100% cotton, EMPA Testmaterialen AG, Switzerland) at temperatures 30° C. and 50° C. Commercial protease preparations Savinase® Ultra 16 L (Novozymes) and Purafect® 4000L (Genencor International) and treatment without enzyme (control) were used for comparison. The stain fabric was first cut in to 1.5 cm×1.5 cm swatches and the pieces were made rounder by cutting the corners. Pieces were placed in wells of microtiter plates (Nunc 150200). Into each well having a diameter of 2 cm, 1.5 ml enzyme dilution in Glysine-NaOH buffer pH 9 was added on top of the fabric. Each enzyme was dosed 0, 0.2, 0.4, 0.8, 1.6, 4, and 8 activity units (µmol tyrosine/min) per 1.5 ml buffer. Activity was measured using 30 min reaction time as described in Example 1(c) using 10 min time for color development after addition of diluted Folin reagent. Microtiter plates with samples were incubated in a horizontal shaker at 30° C. and 50° C. for 60 min with 125 rpm. After that the swatches were carefully rinsed under running water (appr. 45° C.) and dried overnight at indoor air, on a grid, protected against daylight.

The stain removal effect was evaluated by measuring the colour as reflectance values Minolta CM 2500 spectrophotometer using L*a*b* colour space coordinates (illuminant) D65/2°. The colour from both sides of the swatches was measured after the treatment. Each value was the average of at least 2 parallel fabric samples measured from both side of the fabric. Fading of blood/milk/ink stain indicating of the protease performance (stain removal efficiency) was calculated as ΔL*, which means lightness value L* of enzyme treated fabric minus lightness value L* of fabric treated with washing liquor (buffer) without enzyme (enzyme blank, control).

The results are shown in FIGS. 5 and 6. Fe_RF6318 protease preparation showed considerably higher stain removal capacity at 50° C. and especially at 30° C. in pH 9 buffer compared to commercial protease preparations Savinase® Ultra 16L and Purafect® 4000L.

Example 7

Performance of Recombinant Protein Fe_RF6318 with Detergent Powder at 40° C./50° C. And pH 10

Recombinant protein Fe_RF6318 preparation produced in *Trichoderma* (as described in Example 4) was tested for its ability to remove blood/milk/ink standard stain in the presence of phosphate containing reference detergent with and without bleaching agent at 40° C. and 50° C. (pH ca. 10). Standard stain Art.117 (blood/milk/ink, polyester+cotton, EMPA) was used as test material. Commercial protease Purafect® 4000L and treatment without enzyme (control) were used for comparison. Each enzyme was dosed 0, 0.2, 0.4, 0.8, 1.6, 4, and 8 activity units (µmol tyrosine/min) per ml wash liquor. Activity was measured as described in Example 6.

An amount of 3.3 g of phosphate containing ECE reference detergent 77 without optical brightener (Art. 601, EMPA) was dissolved in 1 liter of tap water (water, dH≤4), mixed well with magnetic stirrer and tempered to 40° C./50° C. Stain fabric was cut into pieces like described in Example 6. Swatches were placed in well's of microtiter plates (Nunc 150200) and 1.5 ml wash liquor containing detergent and enzyme dilution in water (below 60 µl) was added on top of the fabric. The plates with samples were in incubated in horizontal shaker at 40° C./50° C. for 60 min with 125 rpm. After that the swatches were carefully/thoroughly rinsed under running water (appr. 45° C.) and dried overnight at indoor air, on a grid, protected from daylight. Another test series was made in a same way except 0.81 g sodium perborate tetrahydrate (Art. 604, EMPA) and 0.16 g bleaching activator TAED tetraacetylethylendiamine (Art. 606, EMPA) was added in addition to detergent.

The colour of the swatches after treatment was measured with Minolta CM 2500 spectrophotometer using L*a*b* color space coordinates and stain removal effect calculated as ΔL* as described in example 6.

The results shown in FIGS. 7A, 7B, 8A and 8B, showed that protease Fe_RF6318 is also suitable with for powder detergents at very alkaline conditions and its resistance for bleaching agents was slightly higher than with commercial protease Purafect® 4000L.

Example 8

Performance of Recombinant Protein Fe_RF6318 with Liquid Detergent at 40° C.

Recombinant protein Fe_RF6318 preparation produced in *Trichoderma* (as described in Example 4) was tested for its ability to remove blood/milk/ink standard stain in the presence of liquid detergent Ariel Sensitive (Procter & Gamble, England), not containing enzyme, at 40° C. and pH ca. 7.9. Standard stain, artificially soiled test cloth Art.117 (blood/milk/ink, polyester+cotton, EMPA) was used as test material. Commercial protease preparations Purafect® 4000L, Savinase® Ultra 16 L and treatment without enzyme (control) were used for comparison. Each enzyme was dosed 0, 0.2, 0.4, 0.8, 1.6, 4, and 8 activity units (μmol tyrosine/min) per ml wash liquor. Activity was measured as described in Example 6.

An amount of 3.3 g of Ariel Sensitive was dissolved in 1 liter of tap water (dH≤4), mixed well with magnetic stirrer and tempered to 40° C. Stain fabric was cut into pieces like described in Example 6. Swatches were placed in wells of microtiter plates (Nunc 150200) and 1.5 ml wash liquor containing detergent and enzyme dilution in water (below 60 nl) was added on top of the fabric. The plates with samples were in incubated in a horizontal shaker at 40° C. for 60 min with 125 rpm. After that the swatches were carefully rinsed under running water (appr. 45° C.) and dried overnight at indoor air, on a grid, protected against daylight.

The colour of the swatches after treatment was measured with Minolta CM 2500 spectrophotometer using L*a*b* color space coordinates and stain removal effect calculated as ΔL* as described in example 6.

Figure 9:
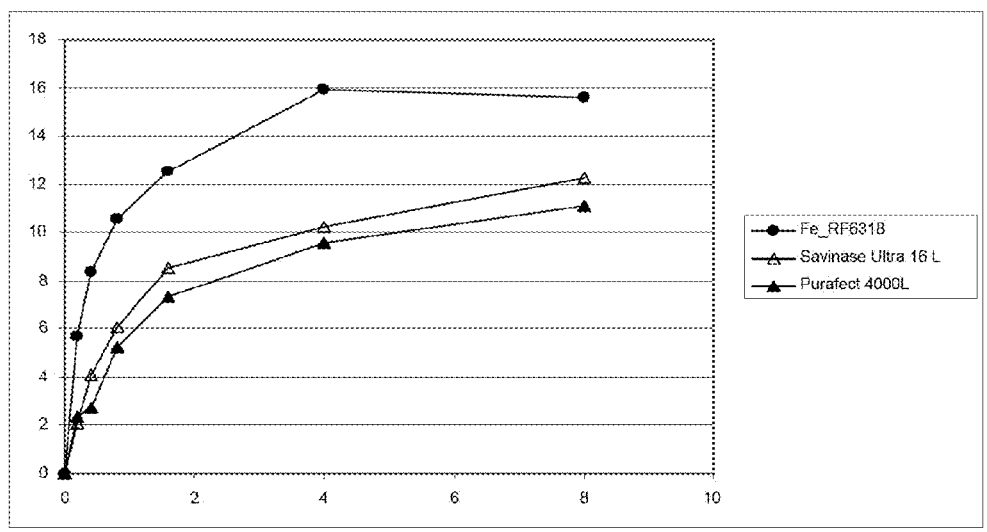
FIG. 9 shows the performance of recombinant Fe_RF6318 protein with blood/milk/ink stain (Art 117, EMPA) and liquid detergent Ariel Sensitive at 40° C., approx. at pH 7.9, 60 min. Commercial preparations Savinase® Ultra 16L and Purafect® 4000L were used for comparison. Shown at x-axis enzyme dosage (activity units/ml), at y-axis ΔL* (deltaL*)=lightness value L* of enzyme treated fabric–lightness value L* of fabric treated with buffer only (enzyme blank).

Based on the results shown in FIG. 9 Fe_RF6318 protease has excellent performance with liquid detergent at 40° C. The efficiency of Fe_RF6318 on blood/milk/ink stain (polyester+cotton) was considerably higher compared to commercial preparations Purafect® 4000L and Savinase® Ultra 14 L, when same amount of protease activity was dosed. The dosage of 4-8 units of commercial enzymes per ml of wash liquor was equal to dosage of about 0.2-0.5% of enzyme preparation per weight of detergent, which is a typical use level for detergent enzymes.

Example 9

Performance of Recombinant Protein Fe_RF6318 with Different Liquid Detergent Concentrations at 30° C.

Recombinant protein Fe_RF6318 preparation produced in *Trichoderma* (as described in Example 4) was tested for its ability to remove blood/milk/ink standard stain with liquid detergent at concentrations 1-5 g/l at 30° C. Ariel Sensitive (Procter & Gamble, England) containing no enzymes and liquid base detergent for coloured fabric containing 25% washing active substances, polyol and polymers (Table 4) were used as detergents and standard stain Art.117 (blood/milk/ink, cotton+polyester, EMPA) was used as test material. Commercial protease preparations Purafect® 4000L, Savinase® Ultra 16 L and treatment without enzyme (control) were used for comparison. Each enzyme was dosed 0, 0.2, 0.4, 0.8, 1.6, 4, and 8 activity units (μmol tyrosine/min) per ml wash liquor. Activity was measured as described in Example 6.

TABLE 4

Composition of Liquid Base detergent for colored fabric

| Ingredients | % |
| --- | --- |
| NaLES (sodium lauryl ether sulphate) | 4.9 |
| Nonionic C12-15 7EO (ethylene oxide) | 15 |
| Na-Soap (Palm Kernel FA) | 4.4 |
| Coco Glucoside | 1 |
| <Total Surfactant> | <25.30> |

TABLE 4-continued

Composition of Liquid Base detergent for colored fabric

| Ingredients | % |
| --- | --- |
| Polyol (Glycerin) | 5 |
| Phosphonate (32%) (ThermPhos) | 2 |
| PVP-Sokalan HP 53 (BASF) | 1 |
| Sokalan PA 15 (BASF) | 1.56 |
| Sorez-100 (ISP) | 0.4 |
| Water upto 100% | |

Amounts of 1, 3.3 and 5 g of liquid detergent was dissolved in 1 liter of tap water (dH 4), mixed well with magnetic stirrer and tempered to 30° C. The pH in the wash liquors was ca. 7.3-7.5 with Base detergent or ca. 7.6-8.0 with Ariel, depending on detergent concentration. Stain fabric was cut into pieces like described in Example 6. Swatches were placed in wells of microtiter plates (Nunc 150200) and 1.5 ml wash liquor containing detergent and enzyme dilution in water (below 60 μl) was added on top of the fabric. The plates with samples were in incubated in a horizontal shaker at 30° C. for 60 min with 125 rpm. After that the swatches were carefully/thoroughly rinsed under warm running water and dried overnight at indoor air, on a grid, protected against daylight.

The colour of the swatches after treatment was measured with Minolta CM 2500 spectrophotometer using L*a*b* colour space coordinates and stain removal effect calculated as ΔL* as described in example 6.

Results obtained with base detergent for coloured fabrics are shown in FIGS. 10 A-D and results obtained with Ariel Sensitive are shown in FIGS. 11A-D. The efficiency of Fe_RF6318 on blood/milk/ink stains was considerably higher compared to commercial preparations Purafect® 4000L and Savinase® Ultra 14 L with both detergents and at all detergent concentrations, when same amount of activity was dosed. Also if dosing is calculated as amount of added protein (FIGS. 10B and 11B), the stain removal efficiency is highest with Fe_RF6318. The amount of protein from the enzyme preparations was determined by Bio-Rad protein assay (Bio-Rad Laboratories, Hercules, Calif.) using bovine gammaglobulin (Bio-Rad) as standard. Results of these tests indicate that Fe_RF6318 protease has excellent performance with liquid detergents at low temperatures, like 30° C.

Example 10

Efficiency of Recombinant Protein Fe_RF6318 on Different Stains with Liquid Detergents at 30° C. (Launder Ometer)

Recombinant protein Fe_RF6318 preparation produced in *Trichoderma* (as described in Example 4) was tested for its ability to remove different stains with liquid detergent at 30° C. and compared to commercial protease preparations Purafect® 4000L and/or Savinase Ultra® 16 L. The following artificially soiled test cloths from EMPA were used: blood/milk/ink (Art.117, polyester+cotton), blood/milk/ink (Art.116, cotton), grass (Art. 164, cotton) and cocoa (Art.112, cotton). The fabric was cut in 9 cm×12 cm swatches and the edges were neated by zig-zag stitches. Two test series were performed: first with Ariel Sensitive without enzymes and second later on with a liquid base detergent for coloured fabric (Example 8). Different batches of stains were used in the above two experiments.

Stain removal treatments were performed in LP-2 Launder Ometer as follows. Launder Ometer was first preheated to 30° C. 450 ml of tempered wash liquor containing 5 g detergent per liter tap water (dH≤4) and enzyme dilution was added in containers containing stains Art. 116 and Art. 117 or stains Art. 164 and Art. 112. Each enzyme was dosed 0, 2, 5, 10, and in some tests 20 or 30 activity units (µmol tyrosine/min) per ml wash liquor. Activity was measured as described in Example 6. The Launder Ometer was run at 30° C. for 60 min and pH about 7.5 (base detergent) or 8 (Ariel). After that the swatches were carefully rinsed under running water (ca. 20° C.) and dried overnight at indoor air, on a grid, protected against daylight.

The colour of the swatches after treatment was measured with Minolta CM 2500 spectrophotometer using L*a*b* color space coordinates and stain removal effect calculated as ΔL* as described in Example 6. The colour from both sides of the swatches was measured after the treatment. Each value was the average of at least 20 measurements per swatch. The measurements were avoided from areas with crease marks formed during the treatment because of the folding of the fabric (in cotton stains Art. 116 and Art. 112).

Results obtained with Ariel® Sensitive (FIG. 12 A-C) show that efficiency on blood/milk/ink and grass stains was considerably higher with Fe_RF6318 compared to commercial preparation Savinase® Ultra 16L at 30° C. when same amount of protease activity was dosed. Also results obtained with cocoa stain were better with Fe_RF6318 (data not shown).

Also results obtained with base detergent (5 g/l) for coloured fabrics (FIG. 13 A-D) showed that efficiency on blood/milk/ink, grass and cocoa stains was considerably higher with Fe_RF6318 compared to commercial preparations Savinase® Ultra 16L and Purafect® 4000L at 30° C., when same amount of protease activity was dosed. The dosage of 10 units of commercial enzymes per ml of liquor was equal to dosage approximately 0.4% of enzyme preparation per weight of detergent, which is in typical use level for detergent enzymes. Results of these tests indicate that Fe_RF6318 protease is efficient on several stains at low temperatures like 30° C.

Example 11

Evaluation of the Performance of the Recombinant Protein Fe_RF6318 in liquid laundry detergent in full scale trials at 30° C.

The performance of recombinant protein Fe_RF6318 preparation produced in *Trichoderma* (Example 4) was tested in liquid detergent in full scale in a washing machine at 30° C. and compared to commercial protease preparations Purafect® 4000L and Savinase® Ultra 16L and treatment with detergent without enzyme. Liquid base detergent for coloured fabrics, as described in Example 9, and 8 different protease sensitive tracers (Table 5) were used. In addition two pieces of ballast soil (CFT-SBL) per wash were placed in wash net to avoid contamination by contact with the other swatches. Tracers were from CFT (Center For Testmaterials BV, The Netherlands). Stain swatches 10 cm×10 cm were stitched to kitchen towels. The process parameters and conditions are described in Table 6. Enzyme dosages used in the trials were calculated both as enzyme activities (ca. 0-14 activity units per ml wash liquor) and as amount of protein (ca. 0-2.2 mg per liter wash liquor). Protease activities and protein contents of the preparations were measured as described in Examples 6 and 9.

TABLE 5

Protease sensitive tracers used in test.

| Nr. | Monitor/Swatch | Substrate |
| --- | --- | --- |
| 1 | CFT/CS-01-106 | Blood (aged)/Cotton |
| 2 | CFT/C-03-030 | Chocolate milk/pigment/Cotton |

TABLE 5-continued

Protease sensitive tracers used in test.

| Nr. | Monitor/Swatch | Substrate |
| --- | --- | --- |
| 3 | CFT/C-05-059b | Bood/milk/ink/Cotton |
| 4 | CFT/PC-05-014 | Blood/Milk/Ink/PE-Cotton |
| 5 | CFT/CS-08-069 | Grass/Cotton |
| 6 | CFT/C-10-186b | Groundnut oil/milk/Cotton |
| 7 | CFT/CS-25-016 | Spinach/Cotton |
| 8 | CFT/CS-38-010 | Egg Yolk/Pigment/Cotton |

TABLE 6

Process parameters and conditions

| | |
| --- | --- |
| Machine | Miele N-Tronic Frontstar |
| Program | 30° C., short program |
| Hardness of water | about 11.2° dH with 13 liter intake |
| Ballast Load | 2.5 kg bed sheets/bath towels, and kitchen towels |
| Detergent dosage | 80 g/machine load |
| Amount of each tracers | 2 stain trips 10 cm × 10 cm per machine |
| Number of washes | 2 |

Evaluation of stain removal effect was based on measurement of reflectance (R 457 nm) with Datacolor-spectrophotometer with an UV-filter and calculated as percentual stain removal effect (% SR):

$$\% \ SR = \frac{\text{Reflectance after washing} - \text{Reflectance before washing} \times 100\%}{\text{Reflectance of unsoiled fabric} - \text{Reflectance before washing}}$$

Results were calculated as Δ% SR (delta % SR), which means % SR of enzyme treated fabric minus % SR of treatment without enzyme (detergent only).

Two washes containing two swatches of each stain were performed with each dosage of enzyme and three measurements were measured of each stain swatch, so the values are based upon the 12 measurements per stain per product.

The results of total soil removal efficiencies (delta % SR) are shown in FIGS. 14A-B and FIGS. 15 A-E. The total stain removal effect based on the sum of the results obtained with the eight different protease sensitive stains (Stains 1-8, table was higher with Fe_RF6318 compared to commercial protease preparations Purafect® 4000L and Savinase® Ultra 16L, when proteases were dosed as amount of activity and as protein per volume of wash liquor (FIGS. 14A-B). Fe_RF6318 was efficient especially on blood/milk/ink, chocolate/milk, groundnut oil/milk and egg yolk (FIGS. 15A-E).

A general detergency tracer (pigment/oil) was used as a control in repeats in different machines. No differences between the various tests were observed.

Example 12

Performance of Recombinant Protein Fe_RF6318 in pH 9 Buffer at Temperatures from 10° C. to 60° C.

Recombinant protein FeRF6318 produced in *Trichoderma* (as described in Example 4) was tested for its ability to remove blood/milk/ink standard stain (Art.117, polyester+ cotton, EMPA Testmaterialen AG, Swizerland) at temperatures from 10 to 60° C. Commercial protease preparations Savinase® Ultra 16 L, Purafect® 4000 L and Properase® 4000 E and treatment without enzyme (control) were used for comparison. The tests were performed at pH 9 buffer as described in Example 6, except the incubation temperature range was broader, stain material was different and the temperature of the rinsing water of the swatches was similar to washing temperature. The colour of the swatches after treatment was measured with Minolta CM 2500 spectrophotometer using L*a*b* colour space coordinates and stain removal effect calculated as ΔL* as described in Example 6.

The results are shown in FIGS. 16A-F. Fe_RF6318 protease preparation showed higher stain removal capacity at whole temperature range from 10° C. to 60° C. in pH 9 buffer, compared to commercial protease preparations Savinase® Ultra 16L and Purafect® 4000L. It also showed higher stain removal capacity at range from 30° C. to 60° C. compared to Properase® 4000E.

Example 13

Performance of Recombinant Protein Fe_RF6318 with Liquid Detergent at Cold Washing Temperatures 10° C. And 20° C.

Recombinant protein FeRF6318 produced in *Trichoderma* (as described in Example 2) was tested for its ability to remove blood/milk/ink standard stain (Art.117, cotton+polyester, EMPA) with Liquid Base detergent at low temperatures. The testing method was similar to Example 9, except only detergent concentration of 3.3 g/l and lower incubation temperatures, 10° C. and 20° C., were used. The temperature of the rinsing water of the swatches was similar to washing temperature.

The colour of the swatches after treatment was measured with Minolta CM 2500 spectrophotometer using L*a*b* color space coordinates and stain removal effect calculated as ΔL* as described in Example 6. For treatment without enzyme (enzyme blank), detergent solution was used as washing liquor.

Results obtained with Liquid Base detergent concentration of 3.3 g/l at 10° C. and 20° C. are shown in FIGS. 17 A and B. The efficiency of Fe_RF6318 on blood/milk/ink stain was considerably higher both at 10° C. and 20° C. compared to commercial preparations Savinase® Ultra 16L, Purafect® 4000L and Properase® 4000E, when same amount of activity was dosed. Results of these tests indicate that Fe_RF6318 protease has excellent performance with liquid detergents at very low washing temperatures.

REFERENCES

Altschul S F, W Gish, W Miller, E W Myers and D J Lipman. 1990. Basic local alignment search tool. J. Mol. Biol. 215: 403-410.
AMFEP, 2007. Association of Manufacturers and Formulators of Enzyme products, List of commercial enzymes at amfep.org/list.html (updated 30 Nov. 2007).
Anwar, A and M Saleemuddin. 1998. Alkaline proteases: A review. Bioresource Technology 64:175-183.
Bolton, E T and B J McCarthy. 1962. A general method for the isolation of RNA complementary to DNA. Proc. Nat. Acad. Sci. USA 48:1390-1397.
Chen, Y-J, and M Inouye, 2008. The intramolecular chaperone-mediated protein folding. Curr. Opin. Struct. Biol. 18: 765-770.
Chemy, J. R., and Fidantsef, A. L. 2003. Directed evolution of industrial enzymes: an update. Curr. Opin. Biotechnol. 14: 438-443.
Edman P and G Begg. 1967. A protein sequenator. Eur. J. Biochem. 1:80-91. Gasteiger, E, A Gattiker, C Hoogland, I Ivanyi, R D Appel and A Bairoch. 2003.
ExPASy: the proteomics server for in-depth protein knowledge and analysis. Nucleic Acids Res. 31:3784-3788.
Geremia R A, Goldman G H, Ardiles W, Vila S B, Van Montagu M, Herrera-Estrella A. 1993) Molecular characterization of the proteinase-encoding gene, prb1, related to mycoparasitism by *Trichoderma harzianum*. Mol. Microbiol. 8 (3):603-613.
Gupta, R, Q K Beg, S Khan and B Chauhan. 2002. An overview on fermentation, downstream processing and properties of microbial alkaline protease. Appl. Microbiol. Biotechnol. 60: 381-395.
Gurr, S J, Uncles, S E, and Kinghorn J R. 1987. The structure and organization of nuclear genes in filamentous fungi. pp 93-139. In (J R Kinghorn, ed.) Gene Structure in Eukaryotic Microbes. IRL Press, Oxford.
Joutsjoki, V V, T K Torkkeli, and K M H Nevalainen. 1993. Transformation of *Trichoderma reesei* with the Hormoconis resinae glucoamylase P (gamP) gene: production of a heterologous glucoamylase by *Trichoderma reesei*. Curr. Genet. 24:223-228.
Kalisz, H M. 1988. Microbial proteinases. Adv. Biochem. Eng. Biotechnol. 36:1-65. Karhunen T, A Mantyla, K M H Nevalainen, and P L Suominen 1993. High frequency one-step gene replacement in *Trichoderma reesei*. I. Endoglucanase I overproduction. Mol. Gen. Genet. 241:515-522.
Laemmli, U K. 1970. Cleavage of structural proteins during the assembly of the head of bacteriophage T4. Nature 227: 680-685.
Malardier L, M J Daboussi, J Julien, F Roussel, C Scazzocchio and Y Brygoo. 1989. Cloning of the nitrate reductase gene (niaD) of *Aspergillus nidulans* and its use for transformation of *Fusarium oxysporum*. Gene 78:147-156.
Maurer, K-H. 2004. Detergent proteases. Curr. Opin. Biotechnol. 15: 330-334. Nielsen H, J Engelbrecht, S Brunak and G von Heijne. 1997. Identification of prokaryotic and eukaryotic signal peptides and prediction of their cleavage sites. Protein Engineering 10:1-6.
Nielsen H and A Krogh. 1998. Prediction of signal peptides and signal anchors by a hidden Markov model. In: Proceedings of the Sixth International Conference on Intelligent Systems for Molecular Biology (ISMB 6), AAAI Press, Menlo Park, Calif., pp. 122-130.
Paloheimo M, A Mantyla, J Kallio, and P Suominen 2003. High-yield production of a bacterial xylanase in the filamentous fungus *Trichoderma reesei* requires a carrier polypeptide with an intact domain structure. Appl. Env. Microbiol. 69:7073-7082.
Penttilä M, H Nevalainen, M Rättö, E Salminen, and J. Knowles. 1987. A versatile transformation system for the cellulolytic filamentous fungus *Trichoderma reesei*. Gene 61:155-164.
Poutanen, M, L Salusjärvi, L Ruohonen, M Penttilä and N Kalkkinen. 2001. Use of matrix-assisted laser desorption/ionization time-of-flight mass mapping and nanospray liquidchromatography/electrospray ionization tandem mass spectrometry sequence tag analysis for high sensitivity identification of yeast proteins separated by two-dimensional gel electrophoresis. Rapid Commun. Mass Spectrom. 15: 1685-1692
Raeder U and P Broda. 1985. Rapid preparation of DNA from filamentous fungi. Lett. Appl. Microbiol. 1:17-20.
Rao, M B, A M Tanksale, M S Ghatge and V V Deshpande. 1998. Molecular and biotechnological aspects of microbial proteases. Microbiol. Mol. Biol. Rev. 62:597-635.
Sambrook J and D W Russell. 2001. Molecular cloning, a laboratory manual. Cold Spring Harbor Laboratory, New York, US.
Shevchenko, A, M. Wilm, O. Vorm, M Mann. 1996. Mass spectrometric sequencing of proteins from silver-stained polyacrylamide gels. Anal Chem. 68: 850-858).

Shimogaki, H, K Takenchi, T. Nishino, M. Ohdera, T. Kudo, K. Ohba, M V Iwama and M Irie. 1991. Purification and properties of a novel surface active agent and alkaline-resistant protease from *Bacillus* sp. Y. Agric. Biol. Chem. 55:2251-2258.

Suarez M B, Vizcaino J A, Lobell A, and Monte E. 2007. Characterization of genes encoding novel peptidases in the biocontrol *Trichoderma harzianum* CECT 2413 using the TrichoEST functional genomics approach. Curr. Genet. 51 (5):331-342.

The invention claimed is:

1. An expression vector, comprising a nucleic acid sequence selected from the group consisting of:
   (a) a nucleic acid sequence encoding a polypeptide exhibiting serine protease activity and comprising the amino acid sequence set forth in SEQ ID NO:15;
   (b) a nucleic acid sequence encoding a polypeptide that comprises an amino acid sequence that exhibits serine protease activity and is at least 92% identical to the amino acid sequence set forth in SEQ ID NO:15, wherein sequence identity is determined using ClustalW alignment using matrix: BLOSUM, Gap Open: 10, and Gap Extension: 0.5, and wherein the amino acid sequence has the serine protease specificity of SEQ ID NO:15;
   (c) a cDNA sequence comprising the coding sequence of the nucleotide sequence set forth in SEQ ID NO:10, wherein the polypeptide encoded by the nucleotide sequence, in its mature form, exhibits serine protease activity;
   (d) a cDNA sequence comprising the coding sequence of the nucleotide sequence set forth in SEQ ID NO:12, wherein the polypeptide encoded by the nucleotide sequence, in its mature form, exhibits serine protease activity;
   (e) a cDNA sequence comprising the coding sequence of the nucleotide sequence set forth in SEQ ID NO:14, wherein the polypeptide encoded by the nucleotide sequence exhibits serine protease activity;
   (f) a cDNA sequence comprising the coding sequence of the nucleotide sequence in plasmid pALK2529 contained in the *E. coli* strain DSM 22172, wherein the nucleotide sequence encodes a polypeptide, which in its mature form, exhibits serine protease activity;
   (g) a nucleic acid sequence the coding sequence of which differs from the coding sequence of the nucleotide sequence of any one of (c) to (f) due to the degeneracy of the genetic code;
   (h) a nucleic acid sequence comprising the nucleotide sequence set forth in SEQ ID NO:12 fused at its 5' end to the nucleotide sequence of a heterologous signal sequence, the nucleic acid sequence encoding a polypeptide, which in its mature form, exhibits serine protease activity; and
   (i) a nucleic acid sequence, that hybridizes under stringent conditions with the complement of the nucleic acid sequence contained in DSM 22171 and encodes a polypeptide comprising an amino acid sequence that exhibits the serine protease specificity of SEQ ID NO:15 and is at least 92% identical to the amino acid sequence set forth in SEQ ID NO:15, wherein sequence identity is determined using ClustalW alignment using matrix: BLOSUM, Gap Open: 10, and Gap Extension: 0.5, and wherein stringent conditions comprise hybridization in a solution comprising 6×SSC, 5×Denhardt's reagent, and 0.5% SDS at 65° C., and washing twice for 15 minutes at 65° C. in a solution comprising 0.1×SSC and 0.1% SDS.

2. The expression vector of claim 1, wherein the vector comprises the nucleic acid sequence encoding a polypeptide exhibiting serine protease activity and comprising the amino acid sequence set forth in SEQ ID NO:15, the nucleic acid sequence operably linked to regulatory sequences capable of directing expression of the polypeptide encoded by the nucleic acid sequence in a host cell.

3. A host cell comprising the expression vector of claim 2.

4. The expression vector of claim 1, wherein the expression vector comprises a nucleic acid sequence encoding a polypeptide that comprises an amino acid sequence that exhibits serine protease activity and is at least 92% identical to the amino acid sequence set forth in SEQ ID NO:15, wherein sequence identity is determined using ClustalW alignment using matrix: BLOSUM, Gap Open: 10, and Gap Extension: 0.5, and wherein the amino acid sequence has the serine protease specificity of SEQ ID NO:15, the nucleic acid sequence operably linked to regulatory sequences capable of directing expression of the polypeptide encoded by the nucleic acid in a host cell.

5. The expression vector of claim 1, wherein the expression vector comprises the nucleic acid sequence that hybridizes under stringent conditions with the complement of the nucleic acid sequence contained in DSM 22171 and encodes a polypeptide comprising an amino acid sequence that exhibits the serine protease specificity of SEQ ID NO:15 and is at least 92% identical to the amino acid sequence set forth in SEQ ID NO:15, wherein sequence identity is determined using ClustalW alignment using matrix: BLOSUM, Gap Open: 10, and Gap Extension: 0.5, and wherein stringent conditions comprise hybridization in a solution comprising 6×SSC, 5×Denhardt's reagent, and 0.5% SDS at 65° C., and washing twice for 15 minutes at 65° C. in a solution comprising 0.1×SSC and 0.1% SDS, the nucleic acid sequence operably linked to regulatory sequences capable of directing expression of the polypeptide encoded by the nucleic acid in a host cell.

6. A host cell comprising the expression vector of claim 5.

7. The host cell of claim 6, wherein the host cell is a microbial host cell.

8. The host cell of claim 6, wherein the host cell is a cell from a filamentous fungus.

9. The host cell of claim 8, wherein the filamentous fungus is of the genus *Trichoderma*, *Aspergillus*, *Fusarium*, *Humicola*, *Chrysosporium*, *Neurospora*, *Rhizopus*, *Penicillium*, or *Mortierella*.

10. The host cell of claim 9, wherein the filamentous fungus is of the genus *Trichoderma*.

11. The host cell of claim 9, wherein the filamentous fungus is of the genus *Aspergillus*.

12. A host cell comprising the expression vector of claim 4.

13. The expression vector of claim 4, wherein the nucleic acid sequence encodes a polypeptide that comprises an amino acid sequence that exhibits serine protease activity and is at least 94% identical to the amino acid sequence set forth in SEQ ID NO:15.

14. The expression vector of claim 4, wherein the nucleic acid sequence encodes a polypeptide that comprises an amino acid sequence that exhibits serine protease activity and is at least 96% identical to the amino acid sequence set forth in SEQ ID NO:15.

15. The expression vector of claim 4, wherein the nucleic acid sequence encodes a polypeptide that comprises an amino acid sequence that exhibits serine protease activity and is at least 98% identical to the amino acid sequence set forth in SEQ ID NO:15.

16. The expression vector of claim 4, wherein the nucleic acid sequence encodes a polypeptide that comprises an amino acid sequence that exhibits serine protease activity and is at least 99% identical to the amino acid sequence set forth in SEQ ID NO:15.

17. The host cell of claim 12, wherein the host cell is a cell from a filamentous fungus of the genus *Trichoderma, Aspergillus, Fusarium, Humicola, Chrysosporium, Neurospora, Rhizopus, Penicillium*, or *Mortierella*.

18. The host cell of claim 3, wherein the host cell is a microbial host cell.

19. The host cell of claim 3, wherein the host cell is a cell from a filamentous fungus.

20. The host cell of claim 19, wherein the filamentous fungus is of the genus *Trichoderma, Aspergillus, Fusarium, Humicola, Chrysosporium, Neurospora, Rhizopus, Penicillium*, or *Mortierella*.

21. The host cell of claim 20, wherein the filamentous fungus is of the genus *Trichoderma*.

22. The host cell of claim 20, wherein the filamentous fungus is of the genus *Aspergillus*.

23. An isolated nucleic acid molecule, comprising a nucleic acid sequence selected from the group consisting of:
    (a) a cDNA sequence comprising the coding sequence of the nucleotide sequence set forth in SEQ ID NO:10, wherein the polypeptide encoded by the nucleotide sequence, in its mature form, exhibits serine protease activity;
    (b) a cDNA sequence comprising the coding sequence of the nucleotide sequence set forth in SEQ ID NO:12, wherein the polypeptide encoded by the nucleotide sequence, in its mature form, exhibits serine protease activity;
    (c) a cDNA sequence comprising the coding sequence of the nucleotide sequence set forth in SEQ ID NO:14, wherein the polypeptide encoded by the nucleotide sequence exhibits serine protease activity;
    (d) a cDNA sequence comprising the coding sequence of the nucleotide sequence in plasmid pALK2529 contained in the *E. coli* strain DSM 22172, wherein the nucleotide sequence encodes a polypeptide, which in its mature form, exhibits serine protease activity;
    (e) a cDNA sequence, the coding sequence of which differs from the coding sequence of the nucleotide sequence of any one of (a) to (d) due to the degeneracy of the genetic code; and
    (f) a cDNA sequence comprising the coding sequence of the nucleotide sequence set forth in SEQ ID NO:12 fused at its 5' end to the nucleotide sequence of a heterologous signal sequence, the cDNA sequence encoding a polypeptide, which in its mature form, exhibits serine protease activity.

24. The nucleic acid molecule of claim 23, wherein the nucleic acid sequence is a cDNA sequence comprising the coding sequence of the nucleotide sequence set forth in SEQ ID NO:10, wherein the polypeptide encoded by the nucleotide sequence, in its mature form, exhibits serine protease activity.

25. The nucleic acid molecule of claim 23, wherein the nucleic acid sequence is a cDNA sequence comprising the coding sequence of the nucleotide sequence set forth in SEQ ID NO:12, wherein the polypeptide encoded by the nucleotide sequence, in its mature form, exhibits serine protease activity.

26. The nucleic acid molecule of claim 23, wherein the nucleic acid sequence is a cDNA sequence comprising the coding sequence of the nucleotide sequence set forth in SEQ ID NO:14, wherein the polypeptide encoded by the nucleotide sequence exhibits serine protease activity.

27. The nucleic acid molecule of claim 23, wherein the nucleic acid sequence is a cDNA sequence comprising the coding sequence of the nucleotide sequence in plasmid pALK2529 contained in *E. coli* strain DSM 22172, wherein the nucleic acid sequence encodes a polypeptide, which in its mature form, exhibits serine protease activity.

28. The nucleic acid molecule of claim 23, wherein the nucleic acid sequence is a cDNA sequence comprising the coding sequence of the nucleotide sequence set forth in SEQ ID NO:12 fused at its 5' end to the nucleotide sequence of a heterologous signal sequence, the cDNA sequence encoding a polypeptide, which in its mature form, exhibits serine protease activity.

29. An expression vector comprising the nucleic acid molecule of claim 24 operably linked to regulatory sequences capable of directing expression of the polypeptide encoded by the nucleic acid molecule in a host cell.

30. An expression vector comprising the nucleic acid molecule of claim 25 operably linked to regulatory sequences capable of directing expression of the polypeptide encoded by the nucleic acid molecule in a host cell.

31. An expression vector comprising the nucleic acid molecule of claim 26 operably linked to regulatory sequences capable of directing expression of the polypeptide encoded by the nucleic acid molecule in a host cell.

32. An expression vector comprising the nucleic acid molecule of claim 27 operably linked to regulatory sequences capable of directing expression of the polypeptide encoded by the nucleic acid molecule in a host cell.

33. An expression vector comprising the nucleic acid molecule of claim 28 operably linked to regulatory sequences capable of directing expression of the polypeptide encoded by the nucleic acid molecule in a host cell.

34. A host cell comprising the expression vector of claim 29.

35. A host cell comprising the expression vector of claim 30.

36. A host cell comprising the expression vector of claim 31.

37. A host cell comprising the expression vector of claim 32.

38. A host cell comprising the expression vector of claim 33.

39. The host cell of claim 36, wherein the host cell is a microbial host cell.

40. The host cell of claim 36, wherein the host cell is a cell from a filamentous fungus.

41. The host cell of claim 40, wherein the filamentous fungus is of the genus *Trichoderma, Aspergillus, Fusarium, Humicola, Chrysosporium, Neurospora, Rhizopus, Penicillium*, or *Mortierella*.

42. The host cell of claim 40, wherein the filamentous fungus is of the genus *Trichoderma*.

43. The host cell of claim 40, wherein the filamentous fungus is of the genus *Aspergillus*.

44. The host cell of claim 42, wherein the host cell is from *Trichoderma reesei*.

45. The host cell of claim 36, wherein the host cell is a heterologous host cell.

46. The host cell of claim 34, wherein the host cell is a microbial host cell.

* * * * *

UNITED STATES PATENT AND TRADEMARK OFFICE
CERTIFICATE OF CORRECTION

PATENT NO. : 8,937,170 B2
APPLICATION NO. : 14/066110
DATED : January 20, 2015
INVENTOR(S) : Kari Juntunen et al.

Page 1 of 3

It is certified that error appears in the above-identified patent and that said Letters Patent is hereby corrected as shown below:

Title Page, item (56),

On page 2, column 1 (Other Publications), line 54, delete "*Hypoxrea lixii* proteinn," and insert -- *Hypocrea lixii* protein, --;

On page 2, column 2 (Other Publications), line 6, delete "medicators of lacasse"," and insert -- mediators of laccase", --;

On page 2, column 2 (Other Publications), line 71, delete "*zease*" and insert -- *zeae* --;

On page 3, column 1 (Other Publications), line 1, delete "procaryotic and eucaryotic" and insert -- prokaryotic and eukaryotic --;

On page 3, column 2 (Other Publications), line 29, delete "preoteinase-" and insert -- proteinase- --;

In the Specification,

In column 1, line 34, delete "(Chemy" and insert -- (Cherry --;

In column 4, line 3, delete "*Mortiriella*." and insert -- *Mortierella*. --;

In column 4, line 38, delete "*Mortiriella*." and insert -- *Mortierella*. --;

In column 4, line 46, delete "*Mortiriella*." and insert -- *Mortierella*. --;

In column 6, line 65, delete "3.3 g/1" and insert -- 3.3 g/l --;

In column 7, line 13, delete "3.3 g/1" and insert -- 3.3 g/l --;

Signed and Sealed this
Twenty-eighth Day of July, 2015

Michelle K. Lee
*Director of the United States Patent and Trademark Office*

CERTIFICATE OF CORRECTION (continued)
U.S. Pat. No. 8,937,170 B2

In column 7, line 13, after "7.9" insert -- . --;

In column 7, line 26, after "EMPA)" insert -- . --;

In column 8, line 64, delete "Ala 412" and insert -- Ala412 --;

In column 9, line 46, delete "wusthedu" and insert -- wustl.edu --;

In column 9, line 64-65, delete "*B. amyloliquifaciens*," and insert -- *B. amyloliquefaciens*, --;

In column 10, line 34, delete "determined" and insert -- determined. --;

In column 10, line 52, delete "determined" and insert -- determined. --;

In column 11, line 47, delete "pl" and insert -- pI --;

In column 15, line 39, delete "FeRF6318" and insert -- Fe_RF6318 --;

In column 15, line 57, delete "*Mortiriella*," and insert -- *Mortierella*, --;

In column 16, line 63, delete "CBS119568." and insert -- CBS 119568. --;

In column 16, line 63, delete "kpa" and insert -- kDa --;

In column 18, line 44 (approx.), delete "*B. sublitis*" and insert -- *B. subtilis* --;

In column 19, line 9, delete "untrasformed" and insert -- untransformed --;

In column 19, line 17, delete "*Mortiriella*," and insert -- *Mortierella*, --;

In column 19, line 28 (approx.), delete "*Mortiriella alpinis*," and insert -- *Mortierella alpine*, --;

In column 22, line 38 (approx.), delete "3.3. g/1" and insert -- 3.3 g/l --;

In column 23, line 12 (approx.), delete "Centralbureau" and insert -- Centraalbureau --;

In column 24, lines 2-3, delete "Folin-Ciocalteau" and insert -- Folin-Ciocalteu --;

In column 24, lines 55-56, delete "polyvinylidine difluororide" and insert -- polyvinylidene difluoride --;

In column 27, line 43, delete "FIG." and insert -- FIGS. --;

In column 28, line 49, delete "Pennila" and insert -- Penttilä --;

In column 28, line 65, delete "supernatants" and insert -- supernatants. --;

In column 29, line 64, delete "Glysine-" and insert -- Glycine- --;

In column 30, lines 9-10, delete "(illuminant) D65/2°." and insert -- (illuminant D65/2°). --;

CERTIFICATE OF CORRECTION (continued)
U.S. Pat. No. 8,937,170 B2

In column 30, line 25, delete "And" and insert -- and --;

In column 31, line 17, delete "60 nl" and insert -- 60 µl --;

In column 32, line 13, delete "(dH 4)," and insert -- (dH≤4), --;

In column 32, line 30, delete "10 A-D" and insert -- 10A-D --;

In column 33, line 17, delete "12 A-C)" and insert -- 12A-C) --;

In column 33, line 25, delete "13 A-D)" and insert -- 13A-D) --;

In column 34, line 4 (approx.), delete "Bood/" and insert -- Blood/ --;

In column 34, line 43, delete "FIGS. 15 A-E." and insert -- FIGS. 15A-E. --;

In column 34, line 61 (approx.), delete "FeRF6318" and insert -- Fe_RF6318 --;

In column 35, line 21, delete "And" and insert -- and --;

In column 35, line 23, delete "FeRF6318" and insert -- Fe_RF6318 --;

In column 35, line 39, delete "17 A" and insert -- 17A --;

In column 36, line 57, after "1685-1692" insert -- . --;

SEQUENCE LISTING

```
<160> NUMBER OF SEQ ID NOS: 15

<210> SEQ ID NO 1
<211> LENGTH: 20
<212> TYPE: PRT
<213> ORGANISM: Fusarium equiseti
<220> FEATURE:
<223> OTHER INFORMATION: Sequence of an aminoterminal peptide #3792
      from Fusarium equiseti RF6318 protease.
<220> FEATURE:
<221> NAME/KEY: MOD_RES
<222> LOCATION: (18)..(18)
<223> OTHER INFORMATION: Cys, Ser, Thr or Arg

<400> SEQUENCE: 1

Ala Leu Thr Thr Gln Ser Asn Ala Pro Trp Gly Leu Ala Ala Ile Ser
1               5                   10                  15

Arg Xaa Thr Pro
            20

<210> SEQ ID NO 2
<211> LENGTH: 10
<212> TYPE: PRT
<213> ORGANISM: Fusarium equiseti
<220> FEATURE:
<223> OTHER INFORMATION: Sequence of a tryptic peptide 1246.673 from
      Fusarium equiseti RF6318  protease.

<400> SEQUENCE: 2

Thr Val Ala Ala Ala Asp Ser Ser Trp Arg
1               5                   10

<210> SEQ ID NO 3
<211> LENGTH: 7
<212> TYPE: PRT
<213> ORGANISM: Fusarium equiseti
<220> FEATURE:
<223> OTHER INFORMATION: Sequence of a tryptic peptide 3341.633 from
      Fusarium equiseti RF6318 protease.
<220> FEATURE:
<221> NAME/KEY: MOD_RES
<222> LOCATION: (1)..(1)
<223> OTHER INFORMATION: Any amino acid

<400> SEQUENCE: 3

Xaa Thr Tyr Gly Val Ala Lys
1               5

<210> SEQ ID NO 4
<211> LENGTH: 14
<212> TYPE: PRT
<213> ORGANISM: Fusarium equiseti
<220> FEATURE:
<223> OTHER INFORMATION: Sequence of a tryptic peptide 1503.799 from
      Fusarium equiseti RF6318 protease
<220> FEATURE:
<221> NAME/KEY: MOD_RES
<222> LOCATION: (3)..(3)
<223> OTHER INFORMATION: Leu or Ile

<400> SEQUENCE: 4

Glu Ala Xaa Thr Val Gly Ala Thr Thr Ser Ala Asp Ala Lys
1               5                   10
```

-continued

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: The sequence of the oligonucleotide primer
      PRO87 derived from the aminoterminal peptide SEQ ID NO:1.
<220> FEATURE:
<221> NAME/KEY: modified_base
<222> LOCATION: (6)..(6)
<223> OTHER INFORMATION: a, c, g or t
<220> FEATURE:
<221> NAME/KEY: modified_base
<222> LOCATION: (12)..(12)
<223> OTHER INFORMATION: a, c, g or t
<220> FEATURE:
<221> NAME/KEY: modified_base
<222> LOCATION: (15)..(15)
<223> OTHER INFORMATION: a, c, g or t

<400> SEQUENCE: 5
cartcnaayg cnccntgggg                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: The sequence of the oligonucleotide primer
      PRO88 derived from the aminoterminal peptide SEQ ID NO:1.
<220> FEATURE:
<221> NAME/KEY: modified_base
<222> LOCATION: (12)..(12)
<223> OTHER INFORMATION: a, c, g or t
<220> FEATURE:
<221> NAME/KEY: modified_base
<222> LOCATION: (15)..(15)
<223> OTHER INFORMATION: a, c, g or t

<400> SEQUENCE: 6
caragyaayg cnccntgggg                                                   20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: The sequence of the oligonucleotide primer
      PRO89 derived from peptide SEQ ID NO:4.
<220> FEATURE:
<221> NAME/KEY: modified_base
<222> LOCATION: (6)..(6)
<223> OTHER INFORMATION: a, c, g or t
<220> FEATURE:
<221> NAME/KEY: modified_base
<222> LOCATION: (9)..(9)
<223> OTHER INFORMATION: a, c, g or t
<220> FEATURE:
<221> NAME/KEY: modified_base
<222> LOCATION: (12)..(12)
<223> OTHER INFORMATION: a, c, g or t
<220> FEATURE:
<221> NAME/KEY: modified_base
<222> LOCATION: (15)..(15)
```

<223> OTHER INFORMATION: a, c, g or t
<220> FEATURE:
<221> NAME/KEY: modified_base
<222> LOCATION: (18)..(18)
<223> OTHER INFORMATION: a, c, g or t

<400> SEQUENCE: 7
gcrtcngcng angtngtngc                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: The sequence of the oligonucleotide primer
      PRO90 derived from peptide SEQ ID NO:4.
<220> FEATURE:
<221> NAME/KEY: modified_base
<222> LOCATION: (6)..(6)
<223> OTHER INFORMATION: a, c, g or t
<220> FEATURE:
<221> NAME/KEY: modified_base
<222> LOCATION: (12)..(12)
<223> OTHER INFORMATION: a, c, g or t
<220> FEATURE:
<221> NAME/KEY: modified_base
<222> LOCATION: (15)..(15)
<223> OTHER INFORMATION: a, c, g or t
<220> FEATURE:
<221> NAME/KEY: modified_base
<222> LOCATION: (18)..(18)
<223> OTHER INFORMATION: a, c, g or t

<400> SEQUENCE: 8
gcrtcngcrc tngtngtngc                                              20

<210> SEQ ID NO 9
<211> LENGTH: 866
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: The sequence of the PCR fragment obtained using
      the primers PRO88 (SEQ ID NO:6) and PRO89 (SEQ ID NO:7) and
      Fusarium equiseti RF6318 genomic DNA as a template.

<400> SEQUENCE: 9
aaagcaacgc accgtggggt cttgctgcca tctcccgccg aaccccggt  ggcagcacct    60 acacctacga caccactgcc ggtgccggta cttacggtta cgtcgttgac tctggtatca   120
acaccgccca cactgacttt ggcggccgtg cttctctcgg ttacaacgct gctggtggcg   180
cccacactga tacccttggc cacggtaccc acgttgctgg taccattgcc tccaacacct   240
acggtgttgc caagcgtgta agtacaatca taccccacat gagctacaac atgatctgaa   300
ctttatactt actattatta ggccaacgtc atctctgtca aggttttcgt cggtaaccaa   360
gcttctacct ctgttatcct tgctggtttc aactgggctg tcaacgacat cacctccaga   420
accgtgctag cccgctctgt catcaacatg tctctcggtg gtccctcttc tcagacctgg   480
gctactgcca tcaacgctgc ctacagccaa ggtgtcctct ccgttgttgc tgccggtaac   540
ggtgattcca acggtcgtcc tctccccgcc tctggccagt ctcctgccaa cgttcccaac   600
gctatcaccg ttgctgccgc cgactccagc tggcgaactg cctctttcac caactacggt   660

```
cctgaggtcg atgtcttcgg tcctggtgtc aacatccagt ccacctggta cacctccaac      720
agcgctacca acaccatcag cggtacctcc atggcttgcc ctcacgttgc tggtcttgct      780
ctctacctcc aggctctcga gaacctcaat acccctgctg ccgtcaccaa ccgcatcaag      840
tctcttgcaa ctacctccgc tgacgc                                          866

<210> SEQ ID NO 10
<211> LENGTH: 1303
<212> TYPE: DNA
<213> ORGANISM: Fusarium equiseti
<220> FEATURE:
<223> OTHER INFORMATION: The nucleotide sequence of the full-length
      Fusarium equiseti RF6318 protease gene (Fe prtS8A).
<220> FEATURE:
<221> NAME/KEY: CDS
<222> LOCATION: (1)..(639)
<220> FEATURE:
<221> NAME/KEY: CDS
<222> LOCATION: (704)..(1300)

<400> SEQUENCE: 10 atg act agc ttc cgc gtt atc gct ctt ggc ctt gca gct ctg ctg ccc        48
Met Thr Ser Phe Arg Val Ile Ala Leu Gly Leu Ala Ala Leu Leu Pro
1               5                   10                  15 gca gtc ctc gcc gct ccc acc gag aag cga cag gag ctc act gcc gcg        96
Ala Val Leu Ala Ala Pro Thr Glu Lys Arg Gln Glu Leu Thr Ala Ala
            20                  25                  30 cct gac aag tac atc atc acc ctc aag ccc gag gct gct gag gcc aag       144
Pro Asp Lys Tyr Ile Ile Thr Leu Lys Pro Glu Ala Ala Glu Ala Lys
        35                  40                  45 gtc gag gct cac atg gcc tgg gtt acc gac gtc cac cgc cgc agc ctc       192
Val Glu Ala His Met Ala Trp Val Thr Asp Val His Arg Arg Ser Leu
    50                  55                  60 ggc aag cgt gac act tcc ggt gtt gag aag aag ttc aac atc agc agc       240
Gly Lys Arg Asp Thr Ser Gly Val Glu Lys Lys Phe Asn Ile Ser Ser
65                  70                  75                  80 tgg aac gcc tac tct ggc gag ttc gac gat gct acc att gct gag atc       288
Trp Asn Ala Tyr Ser Gly Glu Phe Asp Asp Ala Thr Ile Ala Glu Ile
                85                  90                  95 aag aag agc ccc gag gtt gcc ttc gtc gag ccc gac tac att gtc acc       336
Lys Lys Ser Pro Glu Val Ala Phe Val Glu Pro Asp Tyr Ile Val Thr
            100                 105                 110 ctc gac tac aag gtt gag cct ctc tct gac cgt gct ctg acc act cag       384
Leu Asp Tyr Lys Val Glu Pro Leu Ser Asp Arg Ala Leu Thr Thr Gln
        115                 120                 125 agc aac gct cct tgg ggt ctt gct gcc atc tcc cgc cga acc ccc ggt       432
Ser Asn Ala Pro Trp Gly Leu Ala Ala Ile Ser Arg Arg Thr Pro Gly
    130                 135                 140 ggc agc acc tac acc tac gac acc act gcc ggt gcc ggt act tac ggt       480
Gly Ser Thr Tyr Thr Tyr Asp Thr Thr Ala Gly Ala Gly Thr Tyr Gly
145                 150                 155                 160 tac gtc gtt gac tct ggt atc aac acc gcc cac act gac ttt ggc ggc       528
Tyr Val Val Asp Ser Gly Ile Asn Thr Ala His Thr Asp Phe Gly Gly
                165                 170                 175 cgt gct tct ctc ggt tac aac gct gct ggt ggc gcc cac act gat acc       576
Arg Ala Ser Leu Gly Tyr Asn Ala Ala Gly Gly Ala His Thr Asp Thr
            180                 185                 190 ctt ggc cac ggt acc cac gtt gct ggt acc att gcc tcc aac acc tac       624
Leu Gly His Gly Thr His Val Ala Gly Thr Ile Ala Ser Asn Thr Tyr
        195                 200                 205 ggt gtt gcc aag cgt gtaagtacaa tcatacccca catgagctac aacatgatct       679
Gly Val Ala Lys Arg
```

```
                                                                               -continued
         210
gaactttata cttactatta ttag gcc aac gtc atc tct gtc aag gtt ttc       730
                         Ala Asn Val Ile Ser Val Lys Val Phe
                         215                 220 gtc ggt aac caa gct tct acc tct gtt atc ctt gct ggt ttc aac tgg      778
Val Gly Asn Gln Ala Ser Thr Ser Val Ile Leu Ala Gly Phe Asn Trp
        225                 230                 235 gct gtc aac gac atc acc tcc aag aac cgt gct agc cgc tct gtc atc      826
Ala Val Asn Asp Ile Thr Ser Lys Asn Arg Ala Ser Arg Ser Val Ile
240                 245                 250 aac atg tct ctc ggt ggt ccc tct tct cag acc tgg gct act gcc atc      874
Asn Met Ser Leu Gly Gly Pro Ser Ser Gln Thr Trp Ala Thr Ala Ile
255                 260                 265                 270 aac gct gcc tac agc caa ggt gtc ctc tcc gtt gtt gct gcc ggt aac      922
Asn Ala Ala Tyr Ser Gln Gly Val Leu Ser Val Val Ala Ala Gly Asn
            275                 280                 285 ggt gat tcc aac ggt cgt cct ctc ccc gcc tct ggc cag tct cct gcc      970
Gly Asp Ser Asn Gly Arg Pro Leu Pro Ala Ser Gly Gln Ser Pro Ala
        290                 295                 300 aac gtt ccc aac gct atc acc gtt gct gcc gcc gac tcc agc tgg cga     1018
Asn Val Pro Asn Ala Ile Thr Val Ala Ala Ala Asp Ser Ser Trp Arg
305                 310                 315 act gcc tct ttc acc aac tac ggt cct gag gtc gat gtc ttc ggt cct     1066
Thr Ala Ser Phe Thr Asn Tyr Gly Pro Glu Val Asp Val Phe Gly Pro
320                 325                 330 ggt gtc aac atc cag tcc acc tgg tac acc tcc aac agc gct acc aac     1114
Gly Val Asn Ile Gln Ser Thr Trp Tyr Thr Ser Asn Ser Ala Thr Asn
335                 340                 345                 350 acc atc agc ggt acc tcc atg gct tgc cct cac gtt gct ggt ctt gct     1162
Thr Ile Ser Gly Thr Ser Met Ala Cys Pro His Val Ala Gly Leu Ala
            355                 360                 365 ctc tac ctc cag gct ctc gag aac ctc aat acc cct gct gcc gtc acc     1210
Leu Tyr Leu Gln Ala Leu Glu Asn Leu Asn Thr Pro Ala Ala Val Thr
        370                 375                 380 aac cgc atc aag tct ctt gcc act acc ggc cgc atc act ggc agc ctc     1258
Asn Arg Ile Lys Ser Leu Ala Thr Thr Gly Arg Ile Thr Gly Ser Leu
385                 390                 395 agc ggc agc ccc aac gcc atg gct ttc aac ggc gct act gct taa         1303
Ser Gly Ser Pro Asn Ala Met Ala Phe Asn Gly Ala Thr Ala
400                 405                 410

<210> SEQ ID NO 11
<211> LENGTH: 412
<212> TYPE: PRT
<213> ORGANISM: Fusarium equiseti
<220> FEATURE:
<223> OTHER INFORMATION: The deduced amino acid sequence of the
      full-length Fusarium equiseti RF6318 protease (Fe_RF6318)
      including amino acids from Met1 to Ala412.

<400> SEQUENCE: 11

Met Thr Ser Phe Arg Arg Ile Ala Leu Gly Leu Ala Ala Leu Leu Pro
1               5                   10                  15

Ala Val Leu Ala Ala Pro Thr Glu Lys Arg Gln Glu Leu Thr Ala Ala
            20                  25                  30

Pro Asp Lys Tyr Ile Ile Thr Leu Lys Pro Glu Ala Ala Glu Ala Lys
        35                  40                  45

Val Glu Ala His Met Ala Trp Val Thr Asp Val His Arg Arg Ser Leu
    50                  55                  60

Gly Lys Arg Asp Thr Ser Gly Val Glu Lys Lys Phe Asn Ile Ser Ser
```

```
                65                  70                  75                  80
Trp Asn Ala Tyr Ser Gly Glu Phe Asp Asp Ala Thr Ile Ala Glu Ile
                    85                  90                  95

Lys Lys Ser Pro Glu Val Ala Phe Val Glu Pro Asp Tyr Ile Val Thr
                100                 105                 110

Leu Asp Tyr Lys Val Glu Pro Leu Ser Asp Arg Ala Leu Thr Thr Gln
                115                 120                 125

Ser Asn Ala Pro Trp Gly Leu Ala Ala Ile Ser Arg Arg Thr Pro Gly
130                 135                 140

Gly Ser Thr Tyr Thr Tyr Asp Thr Thr Ala Gly Ala Thr Tyr Gly
145                 150                 155                 160

Tyr Val Val Asp Ser Gly Ile Asn Thr Ala His Thr Asp Phe Gly Gly
                165                 170                 175

Arg Ala Ser Leu Gly Tyr Asn Ala Ala Gly Gly Ala His Thr Asp Thr
                180                 185                 190

Leu Gly His Gly Thr His Val Ala Gly Thr Ile Ala Ser Asn Thr Tyr
                195                 200                 205

Gly Val Ala Lys Arg Ala Asn Val Ile Ser Val Lys Val Phe Val Gly
210                 215                 220

Asn Gln Ala Ser Thr Ser Val Ile Leu Ala Gly Phe Asn Trp Ala Val
225                 230                 235                 240

Asn Asp Ile Thr Ser Lys Asn Arg Ala Ser Arg Ser Val Ile Asn Met
                245                 250                 255

Ser Leu Gly Gly Pro Ser Ser Gln Thr Trp Ala Thr Ala Ile Asn Ala
                260                 265                 270

Ala Tyr Ser Gln Gly Val Leu Ser Val Val Ala Ala Gly Asn Gly Asp
                275                 280                 285

Ser Asn Gly Arg Pro Leu Pro Ala Ser Gly Gln Ser Pro Ala Asn Val
                290                 295                 300

Pro Asn Ala Ile Thr Val Ala Ala Ala Asp Ser Ser Trp Arg Thr Ala
305                 310                 315                 320

Ser Phe Thr Asn Tyr Gly Pro Glu Val Asp Val Phe Gly Pro Gly Val
                325                 330                 335

Asn Ile Gln Ser Thr Trp Tyr Thr Ser Asn Ser Ala Thr Asn Thr Ile
                340                 345                 350

Ser Gly Thr Ser Met Ala Cys Pro His Val Ala Gly Leu Ala Leu Tyr
                355                 360                 365

Leu Gln Ala Leu Glu Asn Leu Asn Thr Pro Ala Ala Val Thr Asn Arg
                370                 375                 380

Ile Lys Ser Leu Ala Thr Thr Gly Arg Ile Thr Gly Ser Leu Ser Gly
385                 390                 395                 400

Ser Pro Asn Ala Met Ala Phe Asn Gly Ala Thr Ala
                405                 410

<210> SEQ ID NO 12
<211> LENGTH: 1243
<212> TYPE: DNA
<213> ORGANISM: Fusarium equiseti
<220> FEATURE:
<223> OTHER INFORMATION: The nucleotide sequence encoding the amino acid
      sequence of the proenzyme form of Fusarium equiseti RF6318
      protease.

<400> SEQUENCE: 12
gctcccaccg agaagcgaca ggagctcact gccgcgcctg acaagtacat catcaccctc      60
```

-continued

```
aagcccgagg ctgctgaggc caaggtcgag gctcacatgg cctgggttac cgacgtccac    120
cgccgcagcc tcggcaagcg tgacacttcc ggtgttgaga agaagttcaa catcagcagc    180
tggaacgcct actctggcga gttcgacgat gctaccattg ctgagatcaa gaagagcccc    240
gaggttgcct tcgtcgagcc cgactacatt gtcaccctcg actacaaggt tgagcctctc    300
tctgaccgtg ctctgaccac tcagagcaac gctccttggg gtcttgctgc catctcccgc    360 cgaaccccg gtggcagcac ctacacctac gacaccactg ccggtgccgg tacttacggt    420
tacgtcgttg actctggtat caacaccgcc cacactgact ttggcggccg tgcttctctc    480
ggttacaacg ctgctggtgg cgcccacact gatacccttg ccacggtac ccacgttgct    540 ggtaccattg cctccaacac ctacggtgtt gccaagcgtg taagtacaat catccccac    600 atgagctaca acatgatctg aactttatac ttactattat taggccaacg tcatctctgt    660
caaggttttc gtcggtaacc aagcttctac ctctgttatc cttgctggtt tcaactgggc    720
tgtcaacgac atcacctcca gaaccgtgc tagccgctct gtcatcaaca tgtctctcgg    780
tggtccctct tctcagacct gggctactgc catcaacgct gcctacagcc aaggtgtcct    840
ctccgttgtt gctgccggta acggtgattc caacggtcgt cctctccccg cctctggcca    900
gtctcctgcc aacgttccca acgctatcac cgttgctgcc gccgactcca gctggcgaac    960
tgcctctttc accaactacg gtcctgaggt cgatgtcttc ggtcctggtg tcaacatcca   1020
gtccacctgg tacacctcca cagcgctac caacaccatc agcggtacct ccatggcttg   1080
ccctcacgtt gctggtcttg ctctctacct ccaggctctc gagaacctca ataccctgc   1140 tgccgtcacc aaccgcatca gtctcttgc cactaccggc cgcatcactg gcagcctcag   1200
cggcagcccc aacgccatgg ctttcaacgg cgctactgct taa                     1243
```

<210> SEQ ID NO 13
<211> LENGTH: 392
<212> TYPE: PRT
<213> ORGANISM: Fusarium equiseti
<220> FEATURE:
<223> OTHER INFORMATION: The amino acid sequence of the proenzyme form of Fusarium equiseti RF6318 protease including amino acids Ala21 to Ala 412 of the full length protease.

<400> SEQUENCE: 13

```
Ala Pro Thr Glu Lys Arg Gln Glu Leu Thr Ala Ala Pro Asp Lys Tyr
1               5                   10                  15

Ile Ile Thr Leu Lys Pro Glu Ala Ala Glu Ala Lys Val Glu Ala His
                20                  25                  30

Met Ala Trp Val Thr Asp Val His Arg Arg Ser Leu Gly Lys Arg Asp
            35                  40                  45

Thr Ser Gly Val Glu Lys Lys Phe Asn Ile Ser Trp Asn Ala Tyr
    50                  55                  60

Ser Gly Glu Phe Asp Asp Ala Thr Ile Ala Glu Ile Lys Lys Ser Pro
65                  70                  75                  80

Glu Val Ala Phe Val Glu Pro Asp Tyr Ile Val Thr Leu Asp Tyr Lys
                85                  90                  95

Val Glu Pro Leu Ser Asp Arg Ala Leu Thr Thr Gln Ser Asn Ala Pro
            100                 105                 110

Trp Gly Leu Ala Ala Ile Ser Arg Arg Thr Pro Gly Gly Ser Thr Tyr
        115                 120                 125

Thr Tyr Asp Thr Thr Ala Gly Ala Gly Thr Tyr Gly Tyr Val Val Asp
    130                 135                 140
```

Ser Gly Ile Asn Thr Ala His Thr Asp Phe Gly Gly Arg Ala Ser Leu
145                 150                 155                 160

Gly Tyr Asn Ala Ala Gly Gly Ala His Thr Asp Thr Leu Gly His Gly
            165                 170                 175

Thr His Val Ala Gly Thr Ile Ala Ser Asn Thr Tyr Gly Val Ala Lys
            180                 185                 190

Arg Ala Asn Val Ile Ser Val Lys Val Phe Val Gly Asn Gln Ala Ser
            195                 200                 205

Thr Ser Val Ile Leu Ala Gly Phe Asn Trp Ala Val Asn Asp Ile Thr
210                 215                 220

Ser Lys Asn Arg Ala Ser Arg Ser Val Ile Asn Met Ser Leu Gly Gly
225                 230                 235                 240

Pro Ser Ser Gln Thr Trp Ala Thr Ala Ile Asn Ala Ala Tyr Ser Gln
            245                 250                 255

Gly Val Leu Ser Val Val Ala Ala Gly Asn Gly Asp Ser Asn Gly Arg
            260                 265                 270

Pro Leu Pro Ala Ser Gly Gln Ser Pro Ala Asn Val Pro Asn Ala Ile
            275                 280                 285

Thr Val Ala Ala Ala Asp Ser Ser Trp Arg Thr Ala Ser Phe Thr Asn
            290                 295                 300

Tyr Gly Pro Glu Val Asp Val Phe Gly Pro Gly Val Asn Ile Gln Ser
305                 310                 315                 320

Thr Trp Tyr Thr Ser Asn Ser Ala Thr Asn Thr Ile Ser Gly Thr Ser
            325                 330                 335

Met Ala Cys Pro His Val Ala Gly Leu Ala Leu Tyr Leu Gln Ala Leu
            340                 345                 350

Glu Asn Leu Asn Thr Pro Ala Ala Val Thr Asn Arg Ile Lys Ser Leu
            355                 360                 365

Ala Thr Thr Gly Arg Ile Thr Gly Ser Leu Ser Gly Ser Pro Asn Ala
            370                 375                 380

Met Ala Phe Asn Gly Ala Thr Ala
385                 390

<210> SEQ ID NO 14
<211> LENGTH: 934
<212> TYPE: DNA
<213> ORGANISM: Fusarium equiseti
<220> FEATURE:
<223> OTHER INFORMATION: The nucleotide sequence encoding the amino acid
      sequence of the mature form of Fusarium equiseti RF6318 protease.

<400> SEQUENCE: 14
gctctgacca ctcagagcaa cgctccttgg ggtcttgctg ccatctcccg ccgaaccccc        60
ggtggcagca cctacaccta cgacaccact gccggtgccg gtacttacgg ttacgtcgtt       120
gactctggta tcaacaccgc ccacactgac tttggcggcc gtgcttctct cggttacaac       180
gctgctggtg cgcccacac tgatacccctt ggccacggta cccacgttgc tggtaccatt       240
gcctccaaca cctacggtgt tgccaagcgt gtaagtacaa tcataccca catgagctac        300 aacatgatct gaactttata cttactatta ttaggccaac gtcatctctg tcaaggtttt       360
cgtcggtaac caagcttcta cctctgttat ccttgctggt ttcaactggg ctgtcaacga       420
catcacctcc aagaaccgtg ctagccgctc tgtcatcaac atgtctctcg gtggtccctc       480
ttctcagacc tgggctactg ccatcaacgc tgcctacagc caaggtgtcc tctccgttgt       540
tgctgccggt aacggtgatt ccaacggtcg tcctctcccc gcctctggcc agtctcctgc       600

```
caacgttccc aacgctatca ccgttgctgc cgccgactcc agctggcgaa ctgcctctttt    660 caccaactac ggtcctgagg tcgatgtctt cggtcctggt gtcaacatcc agtccacctg    720
gtacacctcc aacagcgcta ccaacaccat cagcggtacc tccatggctt gccctcacgt    780
tgctggtctt gctctctacc tccaggctct cgagaacctc aatacccctg ctgccgtcac    840
caaccgcatc aagtctcttg ccactaccgg ccgcatcact ggcagcctca gcggcagccc    900
caacgccatg gctttcaacg cgctactgc ttaa                                 934
```

<210> SEQ ID NO 15
<211> LENGTH: 289
<212> TYPE: PRT
<213> ORGANISM: Fusarium equiseti
<220> FEATURE:
<223> OTHER INFORMATION: The amino acid sequence of the mature form of
      Fusarium equiseti RF6318 protease including amino acids Ala124 to
      Ala412 of the full length enzyme.

<400> SEQUENCE: 15

```
Ala Leu Thr Thr Gln Ser Asn Ala Pro Trp Gly Leu Ala Ala Ile Ser
1               5                   10                  15

Arg Arg Thr Pro Gly Gly Ser Thr Tyr Thr Tyr Asp Thr Thr Ala Gly
            20                  25                  30

Ala Gly Thr Tyr Gly Tyr Val Val Asp Ser Gly Ile Asn Thr Ala His
        35                  40                  45

Thr Asp Phe Gly Gly Arg Ala Ser Leu Gly Tyr Asn Ala Ala Gly Gly
    50                  55                  60

Ala His Thr Asp Thr Leu Gly His Gly Thr His Val Ala Gly Thr Ile
65                  70                  75                  80

Ala Ser Asn Thr Tyr Gly Val Ala Lys Arg Ala Asn Val Ile Ser Val
                85                  90                  95

Lys Val Phe Val Gly Asn Gln Ala Ser Thr Ser Val Ile Leu Ala Gly
            100                 105                 110

Phe Asn Trp Ala Val Asn Asp Ile Thr Ser Lys Asn Arg Ala Ser Arg
        115                 120                 125

Ser Val Ile Asn Met Ser Leu Gly Gly Pro Ser Gln Thr Trp Ala
    130                 135                 140

Thr Ala Ile Asn Ala Ala Tyr Ser Gln Gly Val Leu Ser Val Val Ala
145                 150                 155                 160

Ala Gly Asn Gly Asp Ser Asn Gly Arg Pro Leu Pro Ala Ser Gly Gln
                165                 170                 175

Ser Pro Ala Asn Val Pro Asn Ala Ile Thr Val Ala Ala Ala Asp Ser
            180                 185                 190

Ser Trp Arg Thr Ala Ser Phe Thr Asn Tyr Gly Pro Glu Val Asp Val
        195                 200                 205

Phe Gly Pro Gly Val Asn Ile Gln Ser Thr Trp Tyr Thr Ser Asn Ser
    210                 215                 220

Ala Thr Asn Thr Ile Ser Gly Thr Ser Met Ala Cys Pro His Val Ala
225                 230                 235                 240

Gly Leu Ala Leu Tyr Leu Gln Ala Leu Glu Asn Leu Asn Thr Pro Ala
                245                 250                 255
```

```
Ala Val Thr Asn Arg Ile Lys Ser Leu Ala Thr Thr Gly Arg Ile Thr
        260                 265                 270

Gly Ser Leu Ser Gly Ser Pro Asn Ala Met Ala Phe Asn Gly Ala Thr
        275                 280                 285

Ala
```